(12) United States Patent
Lee et al.

(10) Patent No.: US 11,426,210 B2
(45) Date of Patent: Aug. 30, 2022

(54) MULTIPOINT ANGLED FIXATION IMPLANTS FOR MULTIPLE SCREWS AND RELATED METHODS

(71) Applicant: Medos International Sarl, Le Locle (CH)

(72) Inventors: Kevin Lee, Canton, MA (US); Christopher Ramsay, West Wareham, MA (US); J. Riley Hawkins, Cumberland, RI (US); Albert Montello, Duxbury, MA (US)

(73) Assignee: Medos International Sàrl, Le Locle (CH)

( * ) Notice: Subject to any disclaimer, the term of this patent is extended or adjusted under 35 U.S.C. 154(b) by 0 days.

(21) Appl. No.: 16/583,233

(22) Filed: Sep. 25, 2019

(65) Prior Publication Data

US 2021/0085375 A1 Mar. 25, 2021

(51) Int. Cl.
*A61B 17/70* (2006.01)
*A61B 17/56* (2006.01)

(52) U.S. Cl.
CPC ...... *A61B 17/7043* (2013.01); *A61B 17/7002* (2013.01); *A61B 17/7035* (2013.01);
(Continued)

(58) Field of Classification Search
CPC ... A61B 17/7043–7044; A61B 17/7032–7037; A61B 17/7041;
(Continued)

(56) References Cited

U.S. PATENT DOCUMENTS 5,039,265 A 8/1991 Rath et al.
5,133,717 A 7/1992 Chopin
(Continued)

FOREIGN PATENT DOCUMENTS

EP 2 266 483 A1 12/2010
EP 3 429 494 A2 1/2019
(Continued)

OTHER PUBLICATIONS

U.S. Appl. No. 15/073,020, filed Mar. 17, 2016, Multipoint Fixation Implants.
(Continued)

*Primary Examiner* — Julianna N Harvey
(74) *Attorney, Agent, or Firm* — Barnes & Thornburg LLP

(57) ABSTRACT

Bone anchor assemblies and related methods are disclosed herein that can provide for improved fixation of a primary bone anchor. A bone anchor assembly can include a wing with a distal portion that can define a plurality of auxiliary bone anchor openings. Each auxiliary bone anchor opening can receive an auxiliary bone anchor that can augment fixation of a primary bone anchor of the bone anchor assembly. The plurality of auxiliary bone anchor openings can be oriented such that, when the wing is coupled to a primary bone anchor assembly of a vertebral level in a first configuration, at least one auxiliary bone anchor can be driven to extend across a facet plane of the vertebral level and, when coupled in a second configuration, each auxiliary bone anchor received within the wing can be driven to conform to the vertebral level.

10 Claims, 32 Drawing Sheets

(52) U.S. Cl.
CPC ...... *A61B 17/7041* (2013.01); *A61B 17/7044* (2013.01); *A61B 17/7058* (2013.01); *A61B 17/7067* (2013.01); *A61B 2017/564* (2013.01)

(58) Field of Classification Search
CPC ...... A61B 17/80–8057; A61B 17/7059; A61B 17/7062–17/7064
See application file for complete search history.

(56) References Cited

U.S. PATENT DOCUMENTS

| | | | |
|---|---|---|---|
| 5,147,360 | A | 9/1992 | Dubousset |
| 5,470,333 | A | 11/1995 | Ray |
| 5,582,612 | A | 12/1996 | Lin |
| 5,735,852 | A * | 4/1998 | Amrein ............ A61B 17/7041 606/278 |
| 5,928,233 | A | 7/1999 | Apfelbaum et al. |
| 6,010,503 | A | 1/2000 | Richelsoph et al. |
| 6,524,315 | B1 | 2/2003 | Selvitelli et al. |
| 6,565,569 | B1 | 5/2003 | Assaker et al. |
| 6,585,738 | B1 | 7/2003 | Mangione et al. |
| 6,682,530 | B2 | 1/2004 | Dixon et al. |
| 6,736,820 | B2 | 5/2004 | Biedermann et al. |
| 6,974,460 | B2 | 12/2005 | Carbone et al. |
| 7,179,261 | B2 | 2/2007 | Sicvol et al. |
| 7,232,441 | B2 | 6/2007 | Altarac et al. |
| 7,608,096 | B2 | 10/2009 | Foley et al. |
| 7,618,443 | B2 | 11/2009 | Abdou |
| 7,637,928 | B2 | 12/2009 | Fernandez |
| 7,645,294 | B2 | 1/2010 | Kalfas et al. |
| 7,695,500 | B2 | 4/2010 | Markworth |
| 7,699,876 | B2 | 4/2010 | Barry et al. |
| 7,892,260 | B2 | 2/2011 | Mahoney et al. |
| 7,985,223 | B2 | 7/2011 | Khodadadyan-Klostermann et al. |
| 8,012,184 | B2 | 9/2011 | Schlapfer et al. |
| 8,025,681 | B2 | 9/2011 | Colleran et al. |
| 8,167,917 | B2 | 5/2012 | Chin et al. |
| 8,231,655 | B2 | 7/2012 | Stinson et al. |
| 8,298,269 | B2 | 10/2012 | Null et al. |
| 8,303,631 | B2 | 11/2012 | Duggal et al. |
| 8,343,196 | B2 | 1/2013 | Schneider |
| 8,353,937 | B2 | 1/2013 | Capote et al. |
| 8,454,658 | B2 | 6/2013 | Lindner |
| 8,496,686 | B2 | 7/2013 | Berg et al. |
| 8,506,567 | B2 | 8/2013 | Ziemek et al. |
| 8,551,144 | B2 | 10/2013 | Youssef et al. |
| 8,568,459 | B2 | 10/2013 | Uribe et al. |
| 8,574,268 | B2 | 11/2013 | Chan et al. |
| 8,591,513 | B2 | 11/2013 | Overes et al. |
| 8,758,346 | B2 | 6/2014 | Koay et al. |
| 8,845,697 | B2 | 9/2014 | Montello et al. |
| 8,845,698 | B2 | 9/2014 | Schneider |
| 8,852,245 | B2 | 10/2014 | Schneider |
| 8,876,872 | B2 | 11/2014 | Ziolo et al. |
| 8,876,873 | B2 | 11/2014 | Schneider |
| 8,894,695 | B2 | 11/2014 | Moore et al. |
| 8,979,903 | B2 | 3/2015 | Capote et al. |
| 9,060,815 | B1 | 6/2015 | Gustine et al. |
| 9,962,192 | B2 | 5/2018 | Hawkins et al. |
| 10,238,432 | B2 | 3/2019 | Carruth et al. |
| 10,568,674 | B1 * | 2/2020 | Eichenseer ........ A61B 17/7032 |
| 10,779,861 | B2 | 9/2020 | Hawkins et al. |
| 10,898,232 | B2 | 1/2021 | Lee et al. |
| 11,154,332 | B2 | 10/2021 | Hawkins et al. |
| 11,304,728 | B2 | 4/2022 | Lee |
| 2001/0020169 | A1 | 9/2001 | Metz-Stavenhagen |
| 2001/0047174 | A1 | 11/2001 | Donno et al. |
| 2002/0049446 | A1 | 4/2002 | Harkey et al. |
| 2004/0210218 | A1 | 10/2004 | Dixon et al. |
| 2005/0216004 | A1 | 9/2005 | Schwab |
| 2005/0261688 | A1 | 11/2005 | Grady et al. |
| 2006/0064091 | A1 | 3/2006 | Ludwig et al. |
| 2006/0195089 | A1 * | 8/2006 | LeHuec ............ A61B 17/7059 606/281 |
| 2008/0140130 | A1 | 6/2008 | Chan et al. |
| 2008/0161858 | A1 | 7/2008 | Mahoney et al. |
| 2008/0183217 | A1 | 7/2008 | Glaser |
| 2008/0234733 | A1 | 9/2008 | Scrantz et al. |
| 2009/0125067 | A1 | 5/2009 | Mazzuca et al. |
| 2009/0248077 | A1 | 10/2009 | Johns |
| 2010/0036420 | A1 | 2/2010 | Kalfas et al. |
| 2010/0076496 | A1 | 3/2010 | Fernandez |
| 2010/0094358 | A1 | 4/2010 | Moore et al. |
| 2010/0114174 | A1 | 5/2010 | Jones et al. |
| 2010/0292735 | A1 | 11/2010 | Schlaepfer et al. |
| 2010/0305616 | A1 | 12/2010 | Carbone |
| 2011/0184470 | A1 | 7/2011 | Gorek et al. |
| 2011/0230920 | A1 | 9/2011 | Gorek et al. |
| 2011/0288599 | A1 | 11/2011 | Michielli et al. |
| 2012/0010658 | A1 | 1/2012 | Kirschman |
| 2012/0226316 | A1 | 9/2012 | Dant et al. |
| 2013/0046352 | A1 | 2/2013 | McClintock |
| 2013/0053901 | A1 | 2/2013 | Cormier et al. |
| 2013/0060283 | A1 | 3/2013 | Suh et al. |
| 2013/0085534 | A1 * | 4/2013 | Hainard ............ A61B 17/7055 606/278 |
| 2013/0090688 | A1 | 4/2013 | Montello et al. |
| 2013/0096618 | A1 | 4/2013 | Chandanson et al. |
| 2013/0110163 | A1 | 5/2013 | Ballard et al. |
| 2013/0261679 | A1 | 10/2013 | McBride et al. |
| 2014/0018858 | A1 | 1/2014 | Laeng et al. |
| 2014/0052183 | A1 | 2/2014 | Freese |
| 2014/0081269 | A1 | 3/2014 | Biedermann |
| 2014/0107783 | A1 | 4/2014 | Abdou |
| 2014/0180345 | A1 | 6/2014 | Chan et al. |
| 2014/0188223 | A1 | 7/2014 | Jensen et al. |
| 2014/0249581 | A1 | 9/2014 | Stachniak |
| 2014/0257395 | A1 | 9/2014 | Ledet et al. |
| 2015/0012042 | A1 | 1/2015 | Black |
| 2015/0018889 | A1 | 1/2015 | Schneider |
| 2016/0000473 | A1 | 1/2016 | Ludwig et al. |
| 2016/0022341 | A1 | 1/2016 | Agarwal |
| 2016/0106477 | A1 | 4/2016 | Hynes et al. |
| 2016/0106479 | A1 | 4/2016 | Hynes et al. |
| 2016/0128732 | A1 * | 5/2016 | Strnad ............. A61B 17/7037 606/279 |
| 2017/0265901 | A1 | 9/2017 | Hawkins et al. |
| 2017/0348026 | A1 | 12/2017 | Stein et al. |
| 2018/0214185 | A1 * | 8/2018 | Hawkins ............ A61B 17/7058 |
| 2019/0038323 | A1 | 2/2019 | Minfelde et al. |
| 2019/0183541 | A1 | 6/2019 | Lee et al. |
| 2019/0254719 | A1 * | 8/2019 | Gandhi ............ A61B 17/7011 |
| 2019/0290331 | A1 | 9/2019 | Lee et al. |
| 2020/0030007 | A1 | 1/2020 | Hawkins et al. |
| 2020/0229847 | A1 | 7/2020 | Capote et al. |
| 2021/0100589 | A1 | 4/2021 | Lee et al. |
| 2021/0251662 | A1 | 8/2021 | Lee et al. |
| 2022/0015806 | A1 | 1/2022 | Hawkins et al. |

FOREIGN PATENT DOCUMENTS

| | | |
|---|---|---|
| FR | 2 951 064 A1 | 4/2011 |
| WO | 2015/142320 A1 | 9/2015 |

OTHER PUBLICATIONS

U.S. Appl. No. 15/926,069, filed Mar. 20 2018, Multipoint Fixation Implants and Related Methods.
U.S. Appl. No. 15/940,757, filed Mar. 29, 2018, Multipoint Fixation Implants.
U.S. Appl. No. 16/581,714, filed Sep. 24, 2019, Multipoint Fixation Implants.
International Search Report and Written Opinion for Application No. PCT/IB2019/052191, dated Jul. 8, 2019 (15 pages).
International Search Report and Written Opinion for Application No. PCT/IB2020/058939, dated Feb. 5, 2021 (14 pages).
International Search Report and Written Opinion for Application No. PCT/US2017/022860, dated Sep. 21, 2017 (20 pages).
U.S. Appl. No. 17/124,152, filed Dec. 16, 2020, Multipoint Fixation Implants and Related Methods.
U.S. Appl. No. 17/174,456, filed Feb. 12, 2021, Integrated Multipoint Fixation Screw.

(56) References Cited

OTHER PUBLICATIONS

U.S. Appl. No. 17/489,774, filed Sep. 29, 2021, Multipoint Fixation Implants.
U.S. Appl. No. 17/694,645, filed Mar. 14, 2022, Integrated Multipoint Fixation Screw.

* cited by examiner

MULTIPOINT ANGLED FIXATION IMPLANTS FOR MULTIPLE SCREWS AND RELATED METHODS

FIELD

Orthopedic implants and related methods are disclosed herein. For example, bone anchor assemblies with multiple bone engagement points are disclosed.

BACKGROUND

Bone anchor assemblies can be used in orthopedic surgery to fix bone during healing, fusion, or other processes. In spinal surgery, for example, bone anchor assemblies can be used to secure a spinal fixation element to one or more vertebrae to rigidly or dynamically stabilize the spine. Bone anchor assemblies can also be used as an engagement point for manipulating bone (e.g., distracting, compressing, or rotating one vertebra with respect to another vertebra, reducing fractures in a long bone, and so forth).

The integrity with which the bone anchor assembly engages the bone can affect the transfer of corrective biomechanical forces. While a great amount of care is exercised when placing bone anchor assemblies, it is common that a bone anchor assembly will be inserted in a compromised state. For example, the bone opening in which the assembly is disposed can be stripped (e.g., by driving the bone anchor assembly past its optimum holding position), the bone anchor assembly can be placed incorrectly (e.g., using an incorrect instrument maneuver such as an over-sized pilot hole), the bone anchor assembly can be placed outside of its intended trajectory (e.g., within a facet capsule or breached through a pedicle wall), or the bone anchor assembly can be inserted into compromised bone (e.g., bone that is fractured, osteoporotic, diseased, or otherwise lacking in structural integrity).

When the bone anchor assembly is in a compromised state, there can be sub-optimal purchase between the bone anchor assembly and the bone. The bone anchor assembly may feel unsecure to the surgeon, and it is possible that the bone anchor assembly could back out or become loosened over time. There are limited options for the surgeon when faced with these types of situations. In spinal surgery, for example, the surgeon can remove the bone anchor assembly and skip the vertebral level, though this can undesirably require expanding the surgical site to additional vertebral levels. The surgeon can remove and re-insert with a larger anchor, though this may not be an option when space for anchoring in the bone is limited. The surgeon can leave the compromised bone anchor assembly in place, which may be the safest alternative if the bone anchor assembly is in a safe location and attachment to the plate, rod, or other implant construct is definitive, as the additional compromised fixation may be better than removal.

Even when a bone anchor assembly is placed in a non-compromised state, the geometry of traditional bone anchor assemblies can limit the flexibility with which the bone attachment point can be located with respect to a plate, rod, or other implant construct coupled to the bone anchor assembly.

There is a continual need for improved bone anchor assemblies and related methods.

SUMMARY

Bone anchor assemblies are disclosed herein that can provide for improved fixation as compared with traditional bone anchor assemblies. An embodiment of an assembly can include a bracket or wing that extends down from the receiver member and accommodates a plurality of auxiliary bone anchors that augment the fixation of the assembly's primary bone anchor. Surgical methods using the bone anchor assemblies described herein are also disclosed.

In one aspect, a bone anchor assembly can include a bone anchor, a receiver member coupled to a proximal end of the bone anchor and defining a recess configured to receive a rod, a closure mechanism mated to the receiver member, a wing having a proximal portion disposed proximal to the receiver member, a distal portion that defines a plurality of auxiliary screw openings, with each of the auxiliary screw openings being configured to receive an auxiliary bone anchor screw, and a spanning portion that connects the proximal and distal portions. The plurality of auxiliary screw openings extend at an angled trajectory relative to a proximal-distal axis of the spanning portion such that, in a first configuration, each auxiliary screw received in each of the plurality of screw openings can conform to a vertebral level in which the bone anchor is inserted and, in a second configuration, at least one of the plurality of auxiliary bone anchor screws received in at least one of the screw openings can extend across a facet plane of the vertebral level in which the bone anchor is inserted. The bone anchor assembly further includes a nut configured to engage the closure mechanism to secure the proximal portion of the wing to the proximal end of the receiver member.

The devices and methods described herein can have a number of additional features and/or variations, all of which are within the scope of the present disclosure. In some embodiments, for example, the distal portion of the wing can extend generally perpendicular to the proximal-distal axis of the spanning portion. The distal portion of the wing can be configured such that an air gap exists between the distal portion of the wing and a proximal-facing surface of a bone into which the bone anchor is inserted when the wing is secured to the receiver member.

In some embodiments, a central axis of each of the plurality of screw openings can extend in one of a caudal direction or a cephalad direction. In some such embodiments, the central axis of each of the plurality of screw openings can extend in a medial direction. A central axis of each of the plurality of screw openings can extend at an angle between about 0 and about 60 degrees relative to the proximal-distal axis of the spanning portion.

Each of the plurality of screw openings can include at least one threaded portion such that a screw can be received at variable angles. In some such embodiments, at least one threaded portion can be a conically threaded portion. In some embodiments, each of the plurality of screw openings can define an interlocking interface.

In another aspect, a method of securing a primary bone anchor assembly to bone is provided, the method can include driving a primary bone anchor having a receiver member coupled to a proximal end of the bone anchor into a vertebral level in a spine of a patient, positioning a rod in the receiver member, attaching a closure mechanism to the receiver member to retain the rod in the receiver member, coupling a proximal portion of a wing to at least one of the closure mechanism and the receiver member. The wing can have a distal portion defining a first auxiliary bone anchor opening and a second auxiliary bone anchor opening and a spanning portion connecting the proximal portion and the distal portion, where each of the first auxiliary bone anchor opening and the second auxiliary bone anchor opening extend at an oblique angle relative to a proximal-distal axis of the spanning portion. The method can include positioning the wing in one of a first position in which a first auxiliary bone anchor and a second auxiliary bone anchor received within the wing conform to the vertebral level into which the bone anchor is driven and a second position in which at least one of a first auxiliary bone anchor and a second auxiliary bone anchor received within the wing extends across a facet plane of the vertebral level into which the bone anchor is driven, inserting a first auxiliary bone anchor through the first bone anchor opening at a first trajectory, inserting a second auxiliary bone anchor through the second bone anchor opening at a second trajectory, and driving the first auxiliary bone anchor at the first trajectory into the vertebral level and the second auxiliary bone anchor at the second trajectory into the bone such that the first auxiliary bone anchor and the second auxiliary bone anchor augment fixation of the primary bone anchor.

The method can further include positioning the wing relative to the receiver member such that the first auxiliary bone anchor opening and the second auxiliary bone anchor opening are biased in a cephalad direction, driving the first auxiliary bone anchor at the first trajectory such that the first auxiliary bone anchor extends wholly within the vertebral level into which the primary bone anchor is driven, and driving the second auxiliary bone anchor at the second trajectory such that the second auxiliary bone anchor extends wholly within the vertebral level into which the primary bone anchor is driven. In some such embodiments, driving the vertebral level into which the primary bone anchor is driven can be a vertebral level of a cervical spine.

The method can further include positioning the wing relative to the receiver member such that the first auxiliary bone anchor opening and the second auxiliary bone anchor opening are biased in a caudal direction, and driving at least one of the first auxiliary bone anchor and the second auxiliary bone anchor to violate a facet plane of the vertebral level into which the primary bone anchor is driven. In some embodiments, positioning the wing can further include positioning the wing such that there is an air gap between the distal portion of the wing and a proximal-facing surface of the vertebral level into which the primary bone anchor is driven.

Coupling the proximal portion of the wing to at least one of the closure mechanism and the proximal surface of the receiver member can include attaching the wing via an extended set screw and locking the wing in place with a nut. In some such embodiments, the method can further include rotating the wing relative to the receiver member about an axis of the extended screw to achieve a desired first auxiliary bone anchor opening trajectory and a desired second auxiliary bone anchor opening trajectory.

In some embodiments, driving the bone primary bone anchor into a vertebral level of the spine can include driving the primary bone anchor into a fused vertebral level of the spine. In some embodiments, driving the first auxiliary bone anchor at the first trajectory and driving the second auxiliary bone anchor at the second trajectory can cause at least one of the first auxiliary bone anchor and the second auxiliary bone anchor to diverge from the primary bone anchor.

In some embodiments, a central axis of the first auxiliary bone anchor opening and a central axis of the second auxiliary bone anchor opening can each be biased between about 0 and about 60 degrees from the proximal-distal axis of the spanning portion. In some embodiments, the first trajectory can extend at an oblique angle relative to a central axis of the first auxiliary bone anchor opening.

Inserting the first auxiliary bone anchor and inserting the second auxiliary bone anchor can further include engaging a threaded surface of the first auxiliary bone anchor with an interlocking interface of the first auxiliary bone anchor opening and engaging a threaded surface of the second auxiliary bone anchor with an interlocking interface of the second auxiliary bone anchor opening.

In any of the foregoing embodiment methods, the closure mechanism can include a threaded post having a radially extending shoulder portion. Coupling the proximal portion of the wing to at least one of the closure mechanism and the proximal terminal end of the receiver member can include disposing at least a portion of the threaded post through the opening formed in the proximal portion of the wing; and receiving the radially extending shoulder portion that extends at least partially above the proximal terminal end of the receiver member in a counter bore formed about the opening in the distal-facing surface of the proximal portion of the wing.

Any of the features or variations described above can be applied to any particular aspect or embodiment of the present disclosure in a number of different combinations. The absence of explicit recitation of any particular combination is due solely to the avoidance of repetition in this summary.

DETAILED DESCRIPTION

Bone anchor assemblies are disclosed herein that can provide for improved fixation as compared with traditional bone anchor assemblies. An exemplary assembly can include a bracket or wing that extends down from the receiver member and accommodates one or more auxiliary bone anchors that augment the fixation of the assembly's primary bone anchor. Another exemplary assembly can include a plate that is seated between the receiver member and the rod and accommodates one or more auxiliary bone anchors that augment the fixation of the assembly's primary bone anchor. Another exemplary assembly can include a hook that extends out from the receiver member to hook onto an anatomical structure or another implant to augment the fixation of the assembly's primary bone anchor. Surgical methods using the bone anchor assemblies described herein are also disclosed.

Certain exemplary embodiments will now be described to provide an overall understanding of the principles of the structure, function, manufacture, and use of the systems and methods disclosed herein. One or more examples of these embodiments are illustrated in the accompanying drawings. Those skilled in the art will understand that the systems and methods specifically described herein and illustrated in the accompanying drawings are non-limiting exemplary embodiments. The features illustrated or described in connection with one exemplary embodiment may be combined with the features of other embodiments.

Prior Art Bone Anchor Assembly

Figure 1A:
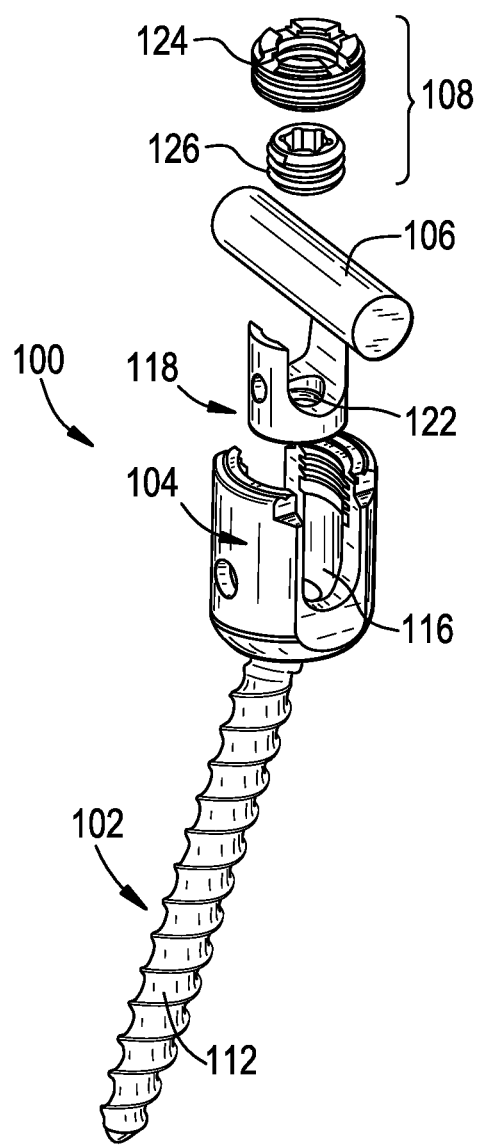
FIG. 1A is an exploded perspective view of a prior art bone anchor assembly.
Figure 1B:
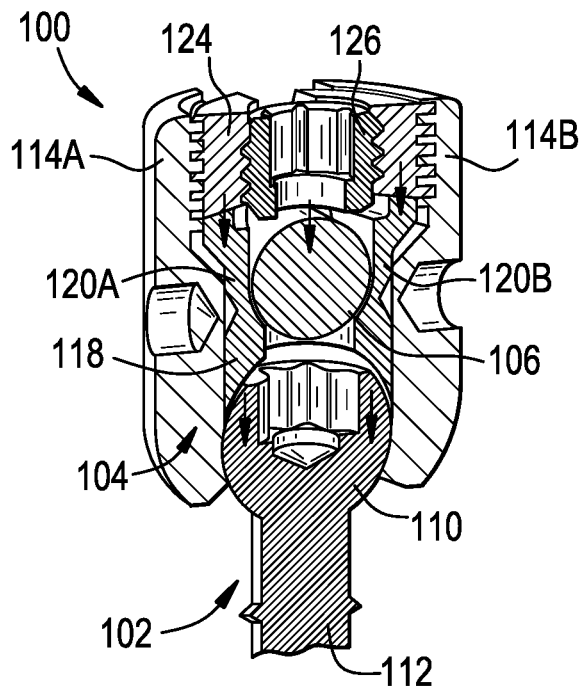
FIG. 1B is a sectional view of the bone anchor assembly of FIG. 1A.
Figure 1C:
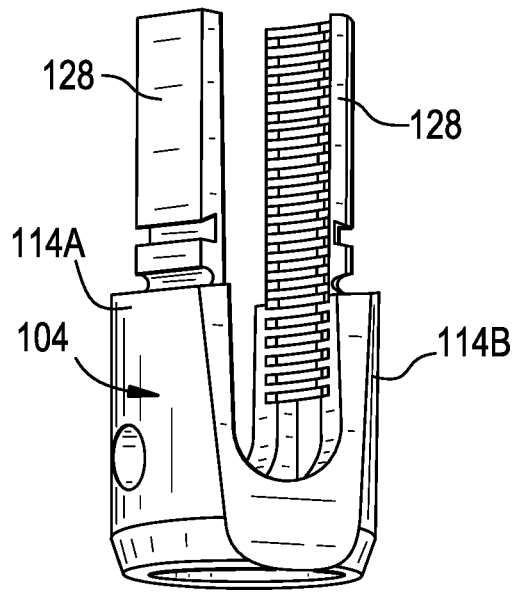
FIG. 1C is a perspective view of the bone anchor assembly of FIG. 1A shown with extension tabs.

FIGS. 1A-1C illustrate a prior art bone anchor assembly 100 with various features that can be included in the bone anchor assemblies described below. It will be appreciated that the illustrated bone anchor assembly 100 is exemplary and that the bone anchor assemblies described herein can include additional or alternative features.

The illustrated bone anchor assembly 100 includes a bone anchor 102, a receiver member 104 for receiving a spinal fixation element, such as a spinal rod 106, to be coupled to the bone anchor 102, and a closure mechanism 108 to capture a spinal fixation element within the receiver member and fix the spinal fixation element with respect to the receiver member. The bone anchor 102 includes a proximal head 110 and a distal shaft 112 configured to engage bone. The receiver member 104 has a proximal end having a pair of spaced apart arms 114A, 114B defining a recess 116 therebetween and a distal end having a distal end surface defining an opening through which at least a portion of the bone anchor 102 extends. The closure mechanism 108 can be positionable between and can engage the arms 114A, 114B to capture a spinal fixation element, e.g., a spinal rod 106, within the receiver member 104 and fix the spinal fixation element with respect to the receiver member.

The proximal head 110 of the bone anchor 102 is generally in the shape of a truncated sphere having a planar proximal surface and an approximately spherically-shaped distal surface. The illustrated bone anchor assembly 100 is a polyaxial bone screw designed for posterior implantation in the pedicle or lateral mass of a vertebra. The proximal head 110 of the bone anchor 102 engages the distal end of the receiver member 104 in a ball and socket like arrangement in which the proximal head and the distal shaft 112 can pivot relative to the receiver member. The distal surface of the proximal head 110 of the bone anchor 102 and a mating surface within the distal end of the receiver member 104 can have any shape that facilitates this arrangement, including, for example, spherical (as illustrated), toroidal, conical, frustoconical, and any combinations of these shapes.

The distal shaft 112 of the bone anchor 102 can be configured to engage bone and, in the illustrated embodiment, includes an external bone engaging thread. The thread form for the distal shaft 112, including the number of threads, the pitch, the major and minor diameters, and the thread shape, can be selected to facilitate connection with bone. Exemplary thread forms are disclosed in U.S. Patent Application Publication No. 2011/0288599, filed on May 18, 2011, and in U.S. Patent Application Publication No. 2013/0053901, filed on Aug. 22, 2012, both of which are hereby incorporated by reference herein. The distal shaft 112 can also include other structures for engaging bone, including a hook. The distal shaft 112 of the bone anchor 102 can be cannulated, having a central passage or cannula extending the length of the bone anchor to facilitate delivery of the bone anchor over a guidewire in, for example, minimally-invasive procedures. Other components of the bone anchor assembly 100, including, for example, the closure mechanism 108, the receiver member 104, and the compression member or cap 118 (discussed below) can be cannulated or otherwise have an opening to permit delivery over a guidewire. The distal shaft 112 can also include one or more sidewall openings or fenestrations that communicate with the cannula to permit bone in-growth or to permit the dispensing of bone cement or other materials through the bone anchor 102. The sidewall openings can extend radially from the cannula through the sidewall of the distal shaft 112. Exemplary systems for delivering bone cement to the bone anchor assembly 100 and alternative bone anchor configurations for facilitating cement delivery are described in U.S. Patent Application Publication No. 2010/0114174, filed on Oct. 29, 2009, which is hereby incorporated by reference herein. The distal shaft 112 of the bone anchor 102 can also be coated with materials to permit bone growth, such as, for example, hydroxyapatite, and the bone anchor assembly 100 can be coated partially or entirely with anti-infective materials, such as, for example, tryclosan.

The proximal end of the receiver member 104 includes a pair of spaced apart arms 114A, 114B defining a U-shaped recess 116 therebetween for receiving a spinal fixation element, e.g., a spinal rod 106. Each of the arms 114A, 114B can extend from the distal end of the receiver member 104 to a free end. The outer surfaces of each of the arms 114A, 114B can include a feature, such as a recess, dimple, notch, projection, or the like, to facilitate connection of the receiver member 104 to instruments. For example, the outer surface of each arm 114A, 114B can include an arcuate groove at the respective free end of the arms. Such grooves are described in more detail in U.S. Pat. No. 7,179,261, issued on Feb. 20, 2007, which is hereby incorporated by reference herein.

The distal end of the receiver member 104 includes a distal end surface which is generally annular in shape defining a circular opening through which at least a portion of the bone anchor 102 extends. For example, the distal shaft 112 of the bone anchor 102 can extend through the opening.

The bone anchor 102 can be selectively fixed relative to the receiver member 104. Prior to fixation, the bone anchor 102 is movable relative to the receiver member 104 within a cone of angulation generally defined by the geometry of the distal end of the receiver member and the proximal head 110 of the bone anchor 102. The bone anchor assembly 100 can be a favored angle screw, for example as disclosed in U.S. Pat. No. 6,974,460, issued on Dec. 13, 2005, and in U.S. Pat. No. 6,736,820, issued on May 18, 2004, both of which are hereby incorporated by reference herein. Alternatively, the bone anchor assembly 100 can be a conventional (non-biased) polyaxial screw in which the bone anchor 102 pivots in the same amount in every direction.

The spinal fixation element, e.g., the spinal rod 106, can either directly contact the proximal head 110 of the bone anchor 102 or can contact an intermediate element, e.g., a compression member 118. The compression member 118 can be positioned within the receiver member 104 and interposed between the spinal rod 106 and the proximal head 110 of the bone anchor 102 to compress the distal outer surface of the proximal head into direct, fixed engagement with the distal inner surface of the receiver member 104. The compression member 118 can include a pair of spaced apart arms 120A and 120B defining a U-shaped seat 122 for receiving the spinal rod 106 and a distal surface for engaging the proximal head 110 of the bone anchor 102.

The proximal end of the receiver member 104 can be configured to receive a closure mechanism 108 positionable between and engaging the arms 114A, 114B of the receiver member. The closure mechanism 108 can be configured to capture a spinal fixation element, e.g., a spinal rod 106, within the receiver member 104, to fix the spinal rod relative to the receiver member, and to fix the bone anchor 102 relative to the receiver member. The closure mechanism 108 can be a single set screw having an outer thread for engaging an inner thread provided on the arms 114A, 114B of the receiver member 104. In the illustrated embodiment, however, the closure mechanism 108 includes an outer set screw 124 operable to act on the compression member 118 and an inner set screw 126 operable to act on the rod 106. The receiver member 104 can include, can be formed integrally with, or can be coupled to one or more extension tabs 128 (shown in FIG. 1C) that extend proximally from the receiver member 104 to functionally extend the length of the arms 114A, 114B. The extension tabs 128 can facilitate installation and assembly of a fixation or stabilization construct and can be removed prior to completing a surgical procedure.

The bone anchor assembly 100 can be used with a spinal fixation element such as rigid spinal rod 106. Alternatively, the spinal fixation element can be a dynamic stabilization member that allows controlled mobility between the instrumented vertebrae.

In use, the bone anchor assembly 100 can be assembled such that the distal shaft 112 extends through the opening in the distal end of the receiver member 104 and the proximal head 110 of the bone anchor 102 is received in the distal end of the receiver member 104. A driver instrument can be fitted with the bone anchor 102 to drive the bone anchor into bone. The compression member 118 can be positioned within the receiver member 104 such that the arms 120A, 120B of the compression member are aligned with the arms 114A, 114B of the receiver member 104 and the lower surface of the compression member 118 is in contact with the proximal head 110 of the bone anchor 102. A spinal fixation element, e.g., the spinal rod 106, can be located in the recess 116 of the receiver member 104. The closure mechanism 108 can be engaged with the inner thread provided on the arms 114A, 114B of the receiver member 104. A torsional force can be applied to the outer set screw 124 to move it within the recess 116 so as to force the compression member 118 onto the proximal head 110 of the bone anchor 102, thereby locking the angular position of the bone anchor 102 relative to the receiver member 104. A torsional force can be applied to the inner set screw 126 to force the spinal rod 106 into engagement with the compression member 118 and thereby fix the spinal rod 106 relative to the receiver member 104.

The bone anchor assemblies described below can be configured to operate in conjunction with, or can include any of the features of, bone anchor assemblies of the type described above (i.e., bone anchor assembly 100) or other types known in the art. Exemplary bone anchor assemblies include monoaxial screws, polyaxial screws, uniplanar screws, favored-angle screws, and/or any of a variety of other bone anchor types known in the art. Further information on favored-angle screws can be found in U.S. Patent Application Publication No. 2013/0096618, filed on Oct. 9, 2012, which is hereby incorporated by reference herein.

Multipoint Fixation Implants

FIGS. 2A-2M illustrate an exemplary embodiment of a bone anchor assembly 200, shown with a spinal rod 206. As noted above, a bone anchor can sometimes be inserted in a compromised state. This can be undesirable, especially in the cervical region of the spine where there is limited bone area in which to install additional bone anchors. The illustrated bone anchor assembly 200 can allow for supplemental fixation of a primary bone anchor in a compact footprint, without necessarily requiring removal or re-insertion of the primary bone anchor. As shown, the bone anchor assembly 200 can include a bone anchor 202, a receiver member 204, a closure mechanism 208, a bracket or wing 230, a nut 232, and one or more auxiliary bone anchors 234. In use, the wing 230 can be secured to the receiver member 204, e.g., using the closure mechanism 208 and nut 232, thereby providing the ability to augment fixation of the bone anchor 202 with the one or more auxiliary bone anchors 234.

Except as described below or as will be readily appreciated by one having ordinary skill in the art, the bone anchor 202 and receiver member 204 are substantially similar to the bone anchor 102 and receiver member 104 described above. A detailed description of the structure and function thereof is thus omitted here for the sake of brevity. The bone anchor assembly 200 can include any one or more of the features of the bone anchor assembly 100 described above.

The closure mechanism 208 can be selectively secured to the receiver member 204 to capture a spinal fixation element, e.g., a spinal rod 206, within the receiver member. Tightening or locking the closure mechanism 208 can be effective to fix the spinal rod 206 relative to the receiver member 204, and to fix an angular position of the bone anchor 202 relative to the receiver member 204. The illustrated closure mechanism 208 is in the form of a threaded post with an enlarged-diameter distal portion 208d and a reduced-diameter proximal portion 208p. In other embodiments, the proximal and distal portions 208p, 208d can have the same diameter, or the proximal portion can have a diameter greater than that of the distal portion. The distal portion 208d of the closure mechanism 208 can be threaded into the receiver member 204 to engage a spinal rod 206 disposed in the receiver member. The proximal portion 208p of the closure mechanism 208 can protrude above the receiver member 204, e.g., above a proximal-facing terminal end surface of the receiver member, and through an opening 236 formed in the wing 230, as described further below.

In the illustrated embodiment, the closure mechanism 208 bears directly against the spinal rod 206, which in turn bears directly against the head of the bone anchor 202. It will be appreciated, however, that one or more intermediate elements can also be included in the bone anchor assembly 200. For example, the bone anchor assembly 200 can include a compression member of the type described above disposed between the spinal rod 206 and the head of the bone anchor 202. The closure mechanism 208 can be a single set screw as shown, or can include an outer set screw operable to act on a compression member and an inner set screw operable to act on the rod 206. The closure mechanism 208 can include a driving interface (e.g., torx, flathead, Phillips head, square, or otherwise) to facilitate rotational advancement or retraction of the closure mechanism relative to the receiver member 204 using a driver instrument.

The nut 232 can include a central opening 238 sized to receive at least a portion of the proximal end 208p of the closure mechanism 208 therethrough. The central opening 238 can include an internal thread that corresponds to the external thread of the closure mechanism 208, such that the nut 232 can be threaded onto the closure mechanism and tightened to secure the wing 230 to the closure mechanism and the receiver member 204 in which the closure mechanism is disposed. The outer surface of the nut 232 can be faceted or otherwise configured to facilitate application of torque to the nut. In some embodiments, the nut 232 can have a hexagonal or square cross-section.

As shown in FIGS. 2E-2H, the bracket or wing 230 can include a proximal portion 230p that can contact the receiver member 204, a distal portion 230d that can contact a bone surface or be disposed in close proximity to a bone surface, and a spanning portion 230s that connects the proximal and distal portions.

The proximal portion 230p of the wing 230 can include a central opening 236 sized to receive at least a portion of the closure mechanism 208 therethrough. For example, the central opening 236 can be sized to receive the proximal portion 208p of the closure mechanism 208 therethrough. The central opening 236 can include a smooth, non-threaded interior surface to allow the wing 230 and the closure mechanism 208 to be freely rotatable with respect to one another. A proximal-facing surface 240 of the proximal portion 230p of the wing 230 can be domed or rounded to provide an atraumatic surface and reduce the risk of tissue irritation post-implantation. A distal-facing surface 242 of the proximal portion 230p of the wing 230 can be configured to engage the proximal-facing surface of the receiver member 204. The distal-facing surface 242 can form a negative or a substantial negative of the proximal-facing surface of the receiver member 204. For example, the proximal-facing surfaces of the arms 214A, 214B of the receiver member 204 can be radially-convex, and the distal-facing surface 242 of the wing 230 can define a radially-concave channel that receives the convex ends of the arms. In some embodiments, the central opening 236 or another feature of the wing 230 can be sized and configured to snap onto or capture a portion of the closure mechanism 208 or a proximal surface of the receiver member 204.

The distal portion 230d of the wing 230 can include one or more openings 244 configured to receive a bone anchor 234 therethrough. While two bone anchor openings 244 are shown in the illustrated embodiment, it will be appreciated that the wing 230 can include any number of bone anchor openings (e.g., one, two, three, four, five, and so on). The bone anchor openings 244 can include any of a number of features for accepting bone anchors 234 at varying angles and/or increasing the security and stability with which bone anchors can be secured to the wing 230. Exemplary features that can be included are disclosed in U.S. Pat. No. 7,637,928, issued on Dec. 29, 2009; U.S. Pat. No. 8,343,196, issued on Jan. 1, 2013; U.S. Pat. No. 8,574,268, issued on Nov. 5, 2013; U.S. Pat. No. 8,845,697, issued on Sep. 30, 2014; and U.S. Pat. No. 8,758,346, issued on Jun. 24, 2014, which are each hereby incorporated by reference herein. For example, the bone anchor openings 244 can be at least partially threaded to receive a variable-angle locking screw having a threaded proximal head. As shown, the openings 244 can have a plurality of columns of threads spaced apart to define a plurality of non-threaded recesses. In the illustrated embodiment, each of the openings 244 has four columns of threads. The columns of threads can be arranged around the inner surface of each of the openings 244 for engaging threads on the heads of locking auxiliary bone anchors and/or variable-angle locking auxiliary bone anchors. The auxiliary bone anchors 234 can thus be locked with the wing 230 coaxially with the central axis of the opening 244 or at a selected angle within a range of selectable angles relative to the central axis of the opening. The auxiliary bone anchors 234 can include features to facilitate this variable-angle locking, such as a proximal head that is at least partially spherical having a thread with a profile that follows the arc-shaped radius of curvature of the spherical portion of the head. The variable-angle capability of the screw/opening interface can allow the user to place locking auxiliary bone anchors into the bone at any angle within defined angulation limits, thus providing improved placement flexibility and eliminating or reducing the need to conform the distal portion of the wing to the bone surface to achieve a desired insertion angle. The auxiliary bone anchors 234 can be driven into the bone with diverging or converging longitudinal axes (relative to each other and/or relative to the primary bone anchor 202) which can provide improved resistance to pullout. In some embodiments, the interior surfaces of the openings 244 can be smooth or spherical, without threads or locking features.

The central axis of each of the openings 244 can be perpendicular or substantially perpendicular to a distal-facing surface 246 of the wing 230. Alternatively, one or more of the openings can have a central axis that extends at an oblique angle with respect to the distal-facing surface 246. In the illustrated embodiment, the central axis of each opening 244 extends at an angle of about 7 degrees with respect to the distal-facing surface 246. In some embodiments, the central axis of each opening 244 can extend at an angle of between about 0 degrees and about 15 degrees with respect to the distal-facing surface 246 (e.g., embodiments used for bony attachment locations that allow direct proximal to distal screw insertion). In some embodiments, the central axis of each opening 244 can extend at an angle of between about 15 degrees and about 45 degrees with respect to the distal-facing surface 246 (e.g., embodiments used for bony attachment locations where an angled trajectory may avoid or target specific anatomy). Angled or divergent central axes can advantageously increase the pullout resistance of the construct.

The distal portion 230d of the wing 230 can have a distal-facing surface 246 configured to contact bone or to be disposed in close proximity to bone. The distal-facing surface 246 can include teeth, texturing, or other surface features to enhance grip with the adjacent bone. The distal portion 230d of the wing 230 can have a lateral surface 248 that abuts a sidewall of the receiver member 204. The lateral surface 248 can form a negative of the sidewall of the receiver member 204, such that the distal-portion 230d of the wing 230 can hug the receiver member with minimal or zero gap therebetween. For example, the lateral surface 248 can be concave with a radius of curvature equal or substantially equal to a radius of curvature of the exterior sidewall of the receiver member 204.

The spanning portion 230s of the wing 230 can extend vertically in a proximal-distal direction to join the proximal portion 230p of the wing to the distal portion 230d of the wing. The spanning portion 230s of the wing 230 can have a lateral surface 250 that engages a sidewall of the receiver member 204. The lateral surface 250 can form a negative of the sidewall of the receiver member 204, such that the spanning portion 230s of the wing 230 can hug the receiver member with minimal or zero gap therebetween. For example, the lateral surface 250 can be concave with a radius of curvature equal or substantially equal to a radius of curvature of the exterior sidewall of the receiver member 204. The lateral surface 250 can also include one or more protrusions 252 for engaging a corresponding recess 254 formed in the sidewall of the receiver member 204, or one or more recesses in which a protrusion of the receiver member is received. The interaction between the one or more protrusions 252 and the one or more recesses 254 can be effective to limit or prevent rotation of the wing 230 with respect to the receiver member 204. This interaction can also be effective to limit or prevent movement of the wing 230 with respect to the receiver member 204 along a proximal-distal axis. The spanning portion 230s can include webbing or ribs 256 to enhance the structural rigidity of the wing 230. The ribs 256 can be formed in an outer surface of the spanning portion 230s, opposite to the lateral surface 250 that engages the receiver member 204.

The proximal portion 230p, distal portion 230d, and spanning portion 230s can be formed integrally as a monolithic unit as shown, or one or more of said components can be separate and selectively attachable to the others. In some embodiments, a kit of modular components can be provided to allow selection of the components most appropriate for a given use. For example, a spanning portion 230s of appropriate height can be selected based on the distance between the proximal end of the receiver member 204 and the bone surface in a given application.

One or more portions of the wing 230 can be flexible or deformable to allow the wing to be custom-tailored for a particular situation. For example, the distal portion 230d of the wing 230 can be flexible or deformable to allow the distal portion to be contoured to the bone surface. The distal portion 230d can be contoured before implantation or in situ. The distal portion 230d can be contoured using a separate bending instrument, or by tightening the bone anchors 234 to deform the distal portion into intimate contact with the bone surface. The distal portion 230d of the wing 230 can be pre-shaped or pre-contoured, e.g., during manufacture, to match a bone surface with which the bone anchor assembly 200 is to be used.

By way of further example, the spanning portion 230s of the wing 230 can be flexible or deformable to allow the position of the bone anchor openings 244 to be adjusted relative to the receiver member 204. The spanning portion 230s can be bent or flexed inwardly or outwardly (e.g., in a medial-lateral direction) to move the bone anchor openings 244 inward towards the receiver member 204 or outward away from the receiver member. Such bending can also increase or decrease the effective height of the wing 230, to accommodate varying distances that may be encountered between the proximal end of the receiver member 204 and the bone surface. The spanning portion 230s can be bent or flexed up or down (e.g., in a superior-inferior direction) to move the bone anchor openings 244 relative to the receiver member 204. The spanning portion 230s can be contoured before implantation or in situ. The spanning portion 230s can be contoured using a separate bending instrument, or by tightening the bone anchors 234 to deform the spanning portion into the desired shape. The spanning portion 230s of the wing 230 can be pre-shaped or pre-contoured, e.g., during manufacture, for a given application.

As yet another example, the proximal portion 230p of the wing 230 can be flexible or deformable, and/or the connections or locations at which the proximal portion 230p, the distal portion 230d, and the spanning portion 230s are joined can be flexible or deformable. The proximal portion 230p, distal portion 230d, and spanning portion 230s can be joined by a living hinge or other joint to allow adjustment to their relative positions.

The spanning portion 230s can have an adjustable height. For example, as shown in FIGS. 2I-2M, the spanning portion 230s can include first and second flexible or deformable legs 258. By bending the legs 258 inward towards one another, the height of the spanning portion 230s can be increased. By bending the legs 258 outward away from one another, the height of the spanning portion 230s can be decreased. Each leg 258 can include an upper portion and a lower portion joined by a flexible joint (e.g., a living hinge, pivot pin, or the like). Rounded or semi-circular surfaces can be formed at the connections between the legs 258 and the proximal and distal portions 230p, 230d of the wing 230 to reduce material stress as the legs are bent. Similarly, a rounded or semi-circular cut-out can be formed where the upper portion of each leg 258 meets the lower portion. The cut-out can reduce stress and provide an engagement surface for gripping the legs 258 with a tool configured to apply a squeezing force thereto.

Figure 2A:
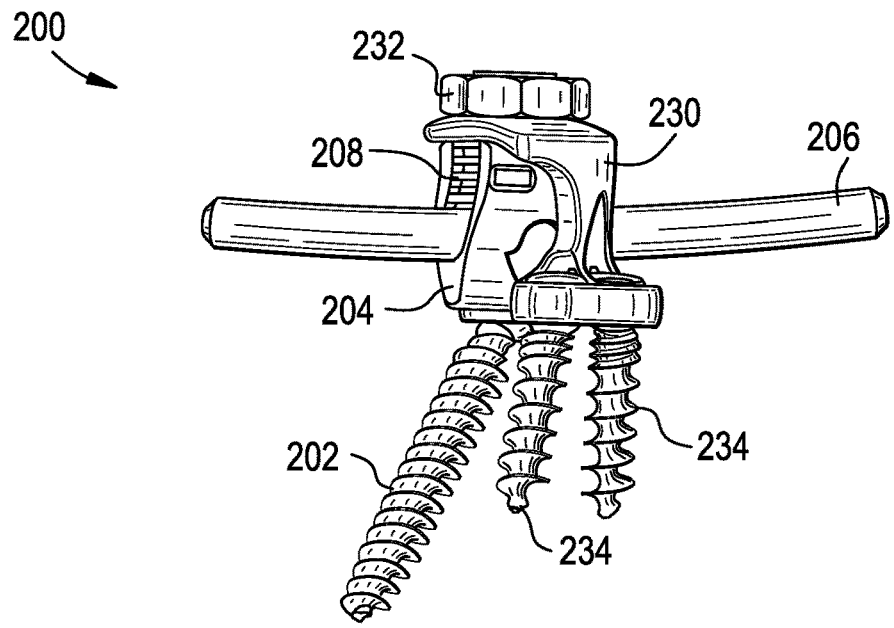
FIG. 2A is a perspective view of a bone anchor assembly and a spinal rod.
Figure 2B:
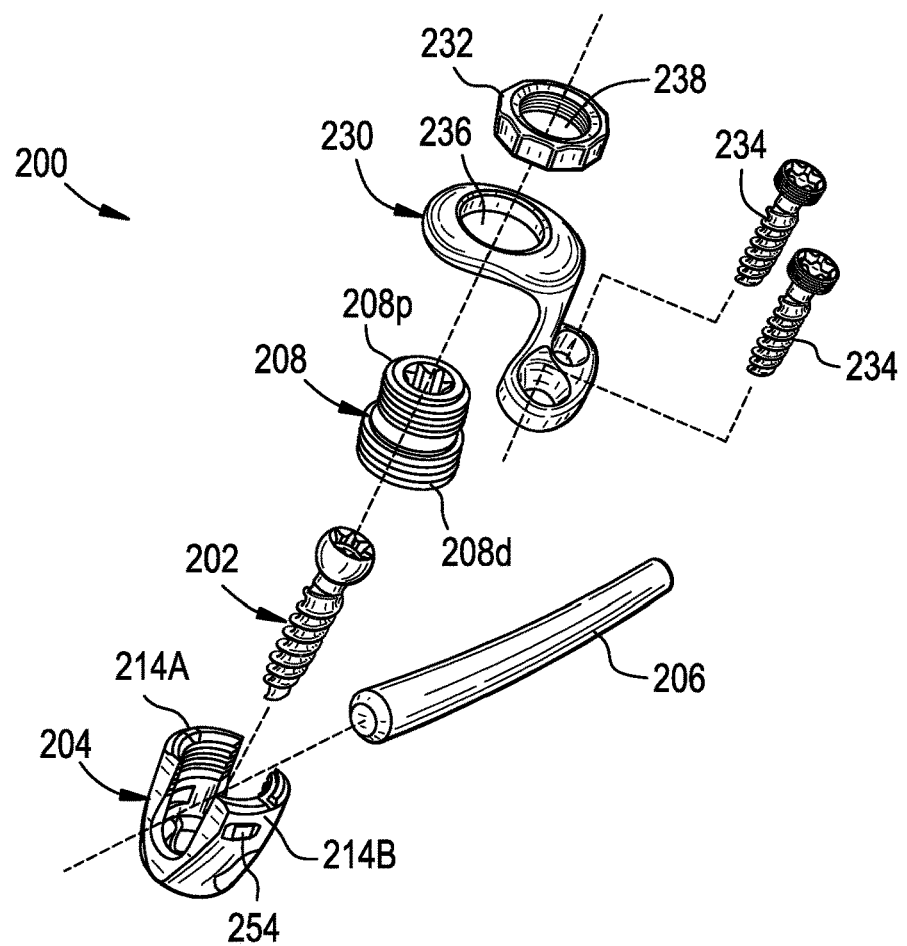
FIG. 2B is a perspective exploded view of the bone anchor assembly and spinal rod of FIG. 2A.
Figure 2C:
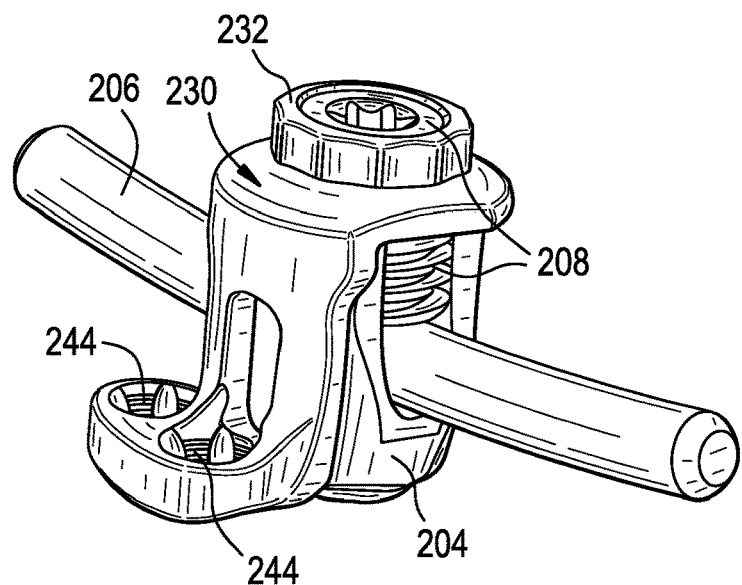
FIG. 2C is a perspective view of the bone anchor assembly and spinal rod of FIG. 2A.
Figure 2D:
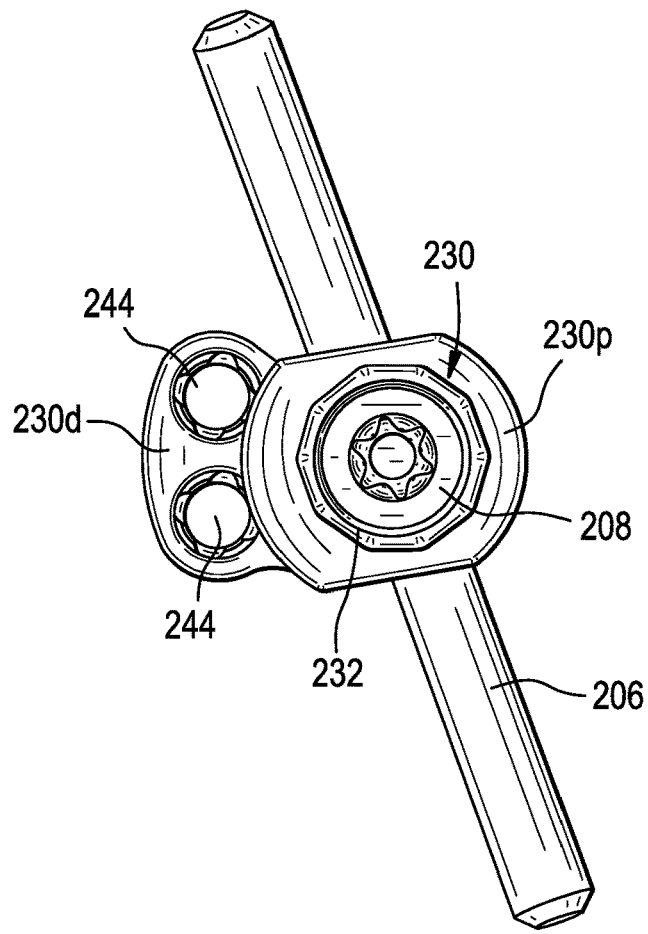
FIG. 2D is a top view of the bone anchor assembly and spinal rod of FIG. 2A.
Figure 2E:
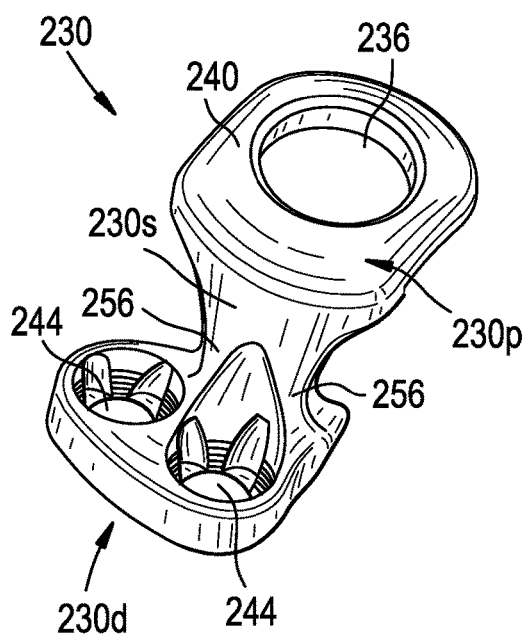
FIG. 2E is a perspective view of a wing of the bone anchor assembly of FIG. 2A.
Figure 2F:
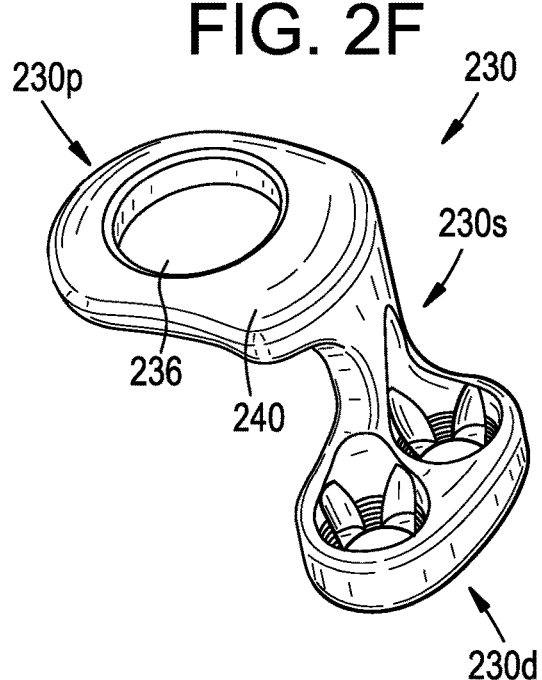
FIG. 2F is another perspective view of a wing of the bone anchor assembly of FIG. 2A.
Figure 2G:
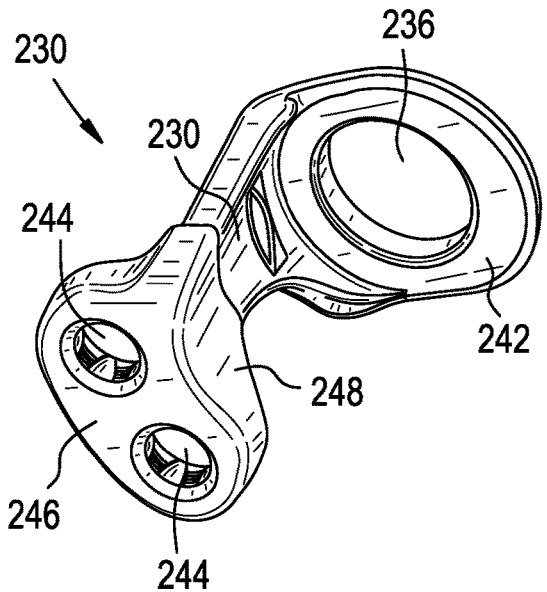
FIG. 2G is another perspective view of a wing of the bone anchor assembly of FIG. 2A.
Figure 2H:
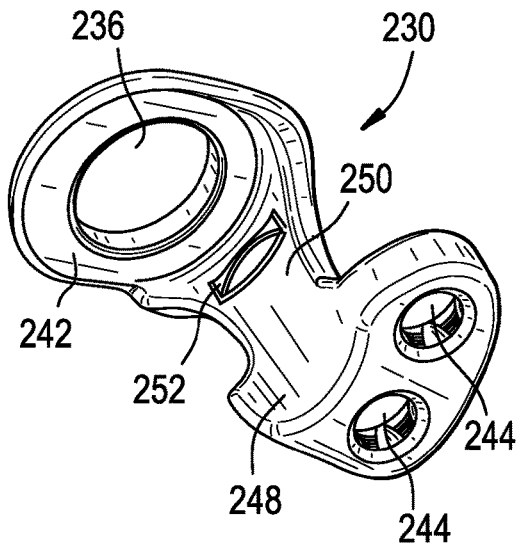
FIG. 2H is another perspective view of a wing of the bone anchor assembly of FIG. 2A.
Figure 2I:
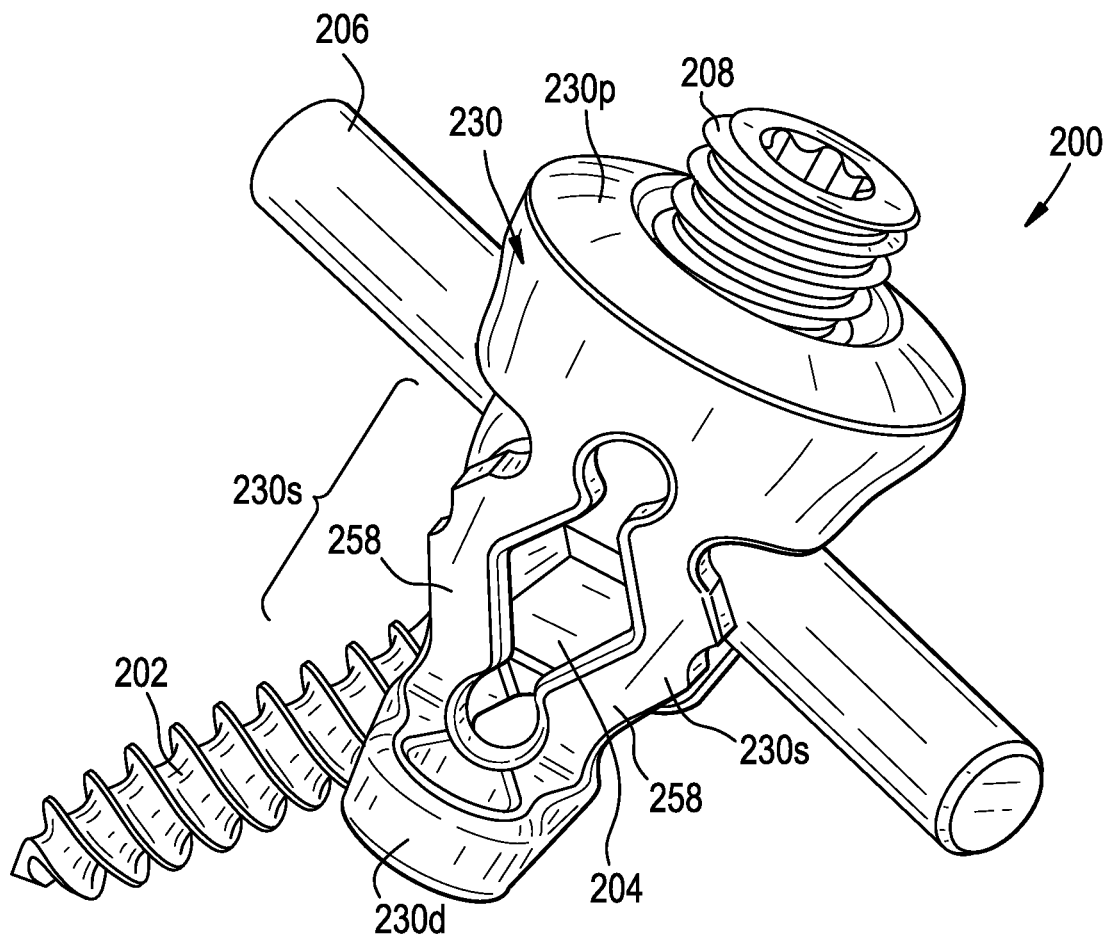
FIG. 2I is a perspective view of the bone anchor assembly and spinal rod of FIG. 2A, shown with an adjustable-height wing.
Figure 2J:
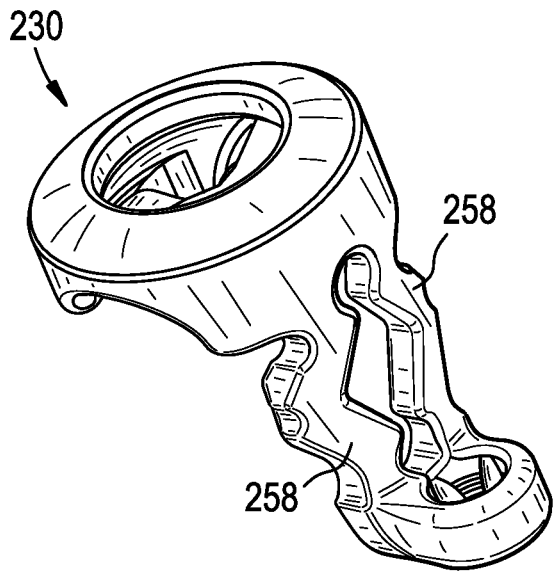
FIG. 2J is a perspective view of a wing of the bone anchor assembly of FIG. 2I.
Figure 2K:
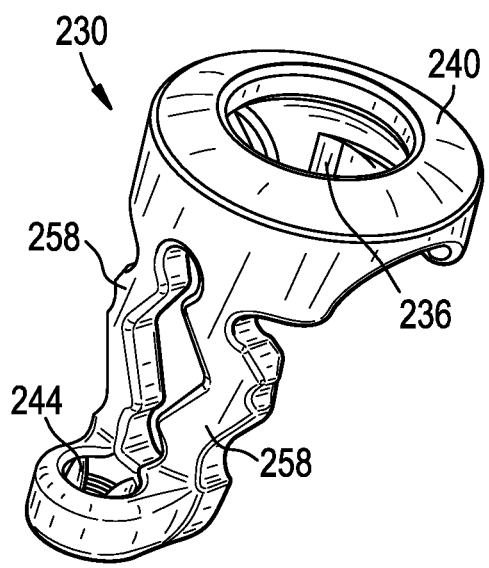
FIG. 2K is another perspective view of a wing of the bone anchor assembly of FIG. 2I.
Figure 2L:
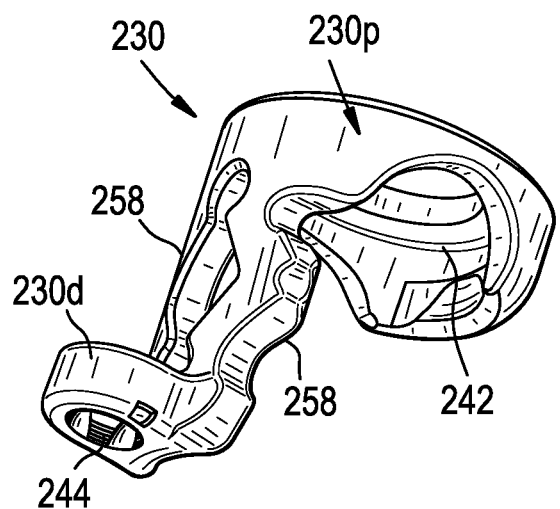
FIG. 2L is another perspective view of a wing of the bone anchor assembly of FIG. 2I.
Figure 2M:
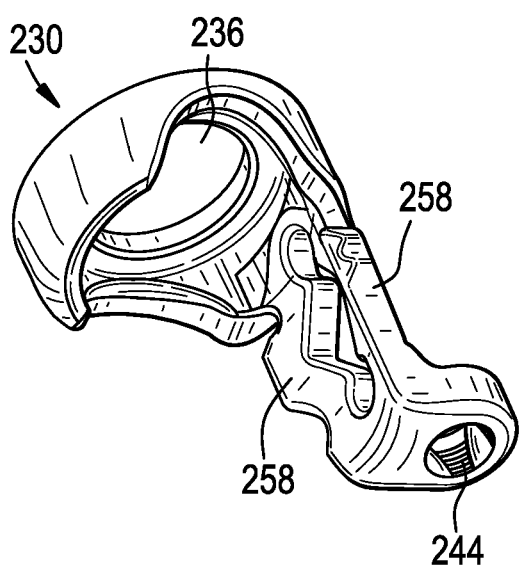
FIG. 2M is another perspective view of a wing of the bone anchor assembly of FIG. 2I.

The bone anchor assembly 200 can provide significant flexibility for the surgeon. The wing 230 can be easily flipped around to be positioned on either side of the rod 206 (e.g., on a medial side or a lateral side of the rod). The wing 230 can be freely rotated about the closure mechanism 208 prior to final locking of the wing to the receiver member 204, allowing the auxiliary bone anchor holes 244 to be positioned at various locations with respect to the spinal rod 206, as shown in FIG. 2D. As described in detail above, the wing 230 can be deformable or flexible, or can include deformable or flexible portions, to allow the wing to fit snugly with the receiver member 204, to match a contour of the bone surface, to reposition the auxiliary bone anchor holes 244 with respect to the receiver member, and/or to adjust a height of the wing to accommodate receiver members of different heights or situations where the primary bone anchor 202 is over or under inserted into the bone.

Referring again to FIG. 2A, the proximal-most extent of each auxiliary bone anchor 234 can be distal to the spinal rod 206. In other embodiments, the proximal-most extent of each auxiliary bone anchor 234 can be distal to the distal-most extent of the receiver member 204. These configurations can advantageously reduce the overall profile of the assembly 200. The wing 200 can be Z-shaped or substantially Z-shaped.

The wing 230 can extend radially outward from the receiver member 204 (e.g., by a distance equal to the width of the distal portion 230d of the wing). The degree to which the wing 230 extends outward from the receiver member 204 can vary among different embodiments. In the illustrated embodiment, the ratio of wing extension to rod diameter (or the ratio of wing extension to the width of the rod-receiving recess in the receiver member) is about 2:1. In some embodiments, this ratio can be less than about 10:1, less than about 5:1, less than about 3:1, less than about 2:1, less than about 1:1, and/or less than about 0.5:1. In some embodiments, the ratio can be about 10:1, about 5:1, about 3:1, about 2:1, about 1:1, or about 0.5:1.

The centers of the auxiliary bone anchor holes 244 (and thus at least a portion of the auxiliary bone anchors 234 disposed therein) can be spaced radially apart from the center of the opening in the receiver member 204 in which the primary bone anchor 202 is disposed. In some embodiments, this spacing can be less than about 2.5 times the diameter of the receiver member 204. In some embodiments, this spacing can be less than about 2 times the diameter of the receiver member 204. In some embodiments, this spacing can be less than the diameter of the receiver member 204. In some embodiments, this spacing can be between about 5 mm and about 10 mm. In some embodiments, this spacing can be about 7.5 mm. In some embodiments, the auxiliary bone anchors 234 can be contained within an envelope no bigger than 2.5 times the diameter of the receiver member 204. In some embodiments, the auxiliary bone anchors 234 can be contained within an envelope no bigger than 2 times the diameter of the receiver member 204.

The auxiliary bone anchors 234 can include any of the features of the bone anchor 202 described above, and any of a variety of other bone screws or other anchors can be used instead or in addition. As noted above, the auxiliary bone anchors 234 can have threaded proximal heads to facilitate variable-angle locking with the wing 230. In some embodiments, the auxiliary bone anchors 234 can have a length of about 6 mm to about 20 mm (e.g., in embodiments used for cervical applications). In some embodiments, the auxiliary bone anchors 234 can have a length of about 6 mm to about 100 mm (e.g., in embodiments used for lumbar or sacral applications). The length of the auxiliary bone anchors 234 can be selected based on various factors, including the available safe bone at any given attachment location. The auxiliary bone anchors 234 can have a length equal to that of the primary bone anchor 202. The auxiliary bone anchors 234 can have a length less than that of the primary bone anchor 202. The auxiliary bone anchors 234 can have a length that is between about 60% and about 80% of the length of the primary bone anchor 202. The auxiliary bone anchors 234 can have a length that is about 70% of the length of the primary bone anchor 202. The auxiliary bone anchors 234 can have a length of about 10 mm. The auxiliary bone anchors 234 can have a length of about 14 mm. In some embodiments, two 10 mm auxiliary bone anchors can be used with one 14 mm primary bone anchor. In some embodiments, one 14 mm auxiliary bone anchor can be used with one 14 mm primary bone anchor. The auxiliary bone anchors 234 can have a shank diameter equal to that of the primary bone anchor 202. The auxiliary bone anchors 234 can have a shank diameter less than that of the primary bone anchor 202. The auxiliary bone anchors 234 can have a shank diameter that is between about 50% and about 70% of the shank diameter of the primary bone anchor 202. The auxiliary bone anchors 234 can have a shank diameter that is about 60% of the shank diameter of the primary bone anchor 202.

As discussed above in the embodiment of FIGS. 2A-2M, supplemental fixation of a primary bone anchor in a bone anchor assembly can be accomplished using a wing or bracket having one or more bone anchor openings through which one or more auxiliary bone anchors can be driven into bone. In some instances, however, a surgeon may experience difficulty in making certain bone anchor placements having angular trajectories. Variability in the bony anatomy of the spine can make it difficult to position the distal portion of the wing in close proximity to bone to facilitate proper engagement or purchase with the anchor. A driver instrument used to drive an auxiliary anchor into bone can require more clearance to access the bone anchor opening of the wing.

To address such potential difficulties in supplemental fixation of auxiliary bone anchors, various embodiments of a bone anchor assembly are disclosed herein that include a wing or bracket having an angled distal portion. In some embodiments, the distal portion of the wing can be angled to the right or left of the spanning portion of the wing to facilitate bone anchor placements having a cephalad trajectory (i.e., towards a patient's head) and/or a caudal trajectory (i.e., towards a patient's feet). In some embodiments, the distal portion of the wing or bracket can, alternatively or additionally, be angled inward or outward to facilitate bone anchor placements having a medial trajectory (i.e., towards the middle of a patient) or a lateral trajectory (i.e., towards the side of a patient). Such angulation can facilitate improved engagement or purchase of the auxiliary anchor to bone and/or access by a driver instrument to the bone anchor opening of the wing.

FIGS. 3A through 3I illustrate an exemplary embodiment of a bone anchor assembly 500 that includes a bracket or wing 530 having an angled distal portion 530d. When viewed from the perspective of FIG. 3A, the distal portion 530d is angled towards the right side of the wing 530. The bone anchor assembly 500 can include a bone anchor 502, a receiver member 504, a closure mechanism 508, a bracket or wing 530, a nut 532 and an auxiliary bone anchor 534. The wing 530 can be secured to the receiver member 504, e.g., using the closure mechanism 508 and nut 532, thereby providing the ability to augment fixation of the bone anchor 502 with the auxiliary bone anchor 534 having an angular trajectory. The closure mechanism 508 can be secured to the receiver member 504 to capture a spinal fixation element, e.g., a spinal rod 506, within the receiver member. Tightening or locking the closure mechanism 508 can be effective to fix the spinal rod 506 relative to the receiver member 504, and to fix an angular position of the bone anchor 502 relative to the receiver member 504.

Except as described below or as will be readily appreciated by one having ordinary skill in the art, the bone anchor 502, the receiver member 504, the closure mechanism 508, the nut 532, and the auxiliary bone anchor 534 are substantially similar to the bone anchor 202, the receiver member 204, the closure mechanism 208, the nut 232, and the auxiliary bone anchors 234 described above with respect to FIGS. 2A-2M. A detailed description of the structure and function thereof is thus omitted here for the sake of brevity. The bone anchor assembly 500 can include any one or more of the features of the bone anchor assembly 200 and/or the bone anchor assembly 100 described above.

In the illustrated embodiment, the bracket or wing 530 can include a proximal portion 530p, an angled distal portion 530d, and a spanning portion 530s that connects the proximal portion to the distal portion of the wing. The proximal portion 530p of the wing 530 can extend horizontally from a proximal end of the spanning portion 530s of the wing 530. The proximal portion 530p can include a proximal-facing surface 540 and a distal-facing surface 542. The proximal-facing surface 540 of the proximal portion 530p of the wing 530 can be domed or rounded to provide an atraumatic surface and reduce the risk of tissue irritation post-implantation. The distal-facing surface 542 of the proximal portion 530p of the wing 530 can be configured to bear against a proximal terminal end or surface of the receiver member 504. The distal-facing surface 542 can form a negative or a substantial negative of the proximal terminal end or surface of the receiver member 504. For example, the proximal-facing surfaces of the arms of the receiver member 504 can be radially-convex, and the distal-facing surface 542 of the wing 530 can define a radially-concave channel (not shown) that receives the convex ends of the arms.

The proximal portion 530p of the wing 530 can define a central opening 536 that extends through the proximal-facing surface 540 and the distal-facing surface 542. The central opening 536 can be oriented such that the central axis of the opening A3 is perpendicular or substantially perpendicular to the distal-facing surface 542 of the proximal portion 530p of the wing 530. The central opening 536 can be sized so that the closure mechanism 508 can be inserted through the opening and extend at least partially above the proximal-facing surface 540 of the proximal portion 530p of the wing 530. The central opening 536 can include a smooth, non-threaded interior surface to allow the wing 530 and the closure mechanism 508 to be freely rotatable with respect to one another. The central opening 536 or another feature of the wing 530 can be sized and configured to snap onto or capture a portion of the closure mechanism 508 or a proximal surface of the receiver member 504. In the illustrated exemplary embodiment, a counter-bore 560 can be formed about the central opening 536 in the distal-facing surface 542 of the proximal portion 530p of the wing 530 to accommodate a radially extending shoulder portion of the closure mechanism 508 that may extend above the proximal terminal end of the receiver member 504. The structure and function of the counter-bore 560 is discussed in more detail with respect to FIG. 4A-4C.

The spanning portion 530s of the wing 530 can extend vertically in a proximal-distal direction to join the proximal portion 530p of the wing to the distal portion 530d of the wing. The spanning portion 530s of the wing 530 can be an elongated arm that extends distally from a side wall of the proximal portion 530p of the wing in a vertical or a substantially vertical plane. The spanning portion 530s of the wing 530 can have a lateral surface 550 that engages or faces a sidewall of the receiver member 504. The lateral surface 550 can form a negative of the sidewall of the receiver member 504, such that the spanning portion 530s of the wing 530 can hug the receiver member with minimal or zero gap there between. For example, the lateral surface 550 can be concave with a radius of curvature equal or substantially equal to a radius of curvature of the exterior sidewall of the receiver member 504. The proximal portion 530p, distal portion 530d, and spanning portion 530s can be formed integrally as a monolithic unit as shown, or one or more of said components can be separate and selectively attachable to the others. In some embodiments, a kit of modular components can be provided to allow selection of the components most appropriate for a given use. For example, a spanning portion 530s of appropriate height can be selected based on the distance between the proximal end of the receiver member 504 and the bone surface in a given application.

In some embodiments, the wing 530 can include various features of a unilateral locking interface, including but not limited to one or more grooves 570a, 570b, and surface projections 570c. The unilateral locking interface enables a surgical instrument that includes a unilateral locking mechanism (not shown) to rigidly hold onto one side of the wing 530. Exemplary unilateral locking interfaces that can be included in the wing 530 are disclosed in U.S. patent application Ser. No. 15/843,618, filed on Dec. 15, 2017 and entitled "Unilateral Implant Holders and Related Methods," the entire contents of which are hereby incorporated by reference.

The angled distal portion 530d of the wing 530 can extend outward from the distal end of the spanning portion 530s away from the receiver member 504. The degree to which the wing 530 extends outward from the receiver member 504 can vary among different embodiments. In the illustrated embodiment, the ratio of wing extension to rod diameter (or the ratio of wing extension to the width of the rod-receiving recess in the receiver member) is about 2:1. In some embodiments, this ratio can be less than about 10:1, less than about 5:1, less than about 3:1, less than about 2:1, less than about 1:1, and/or less than about 0.5:1. In some embodiments, the ratio can be about 10:1, about 5:1, about 3:1, about 2:1, about 1:1, or about 0.5:1.

Figure 3A:
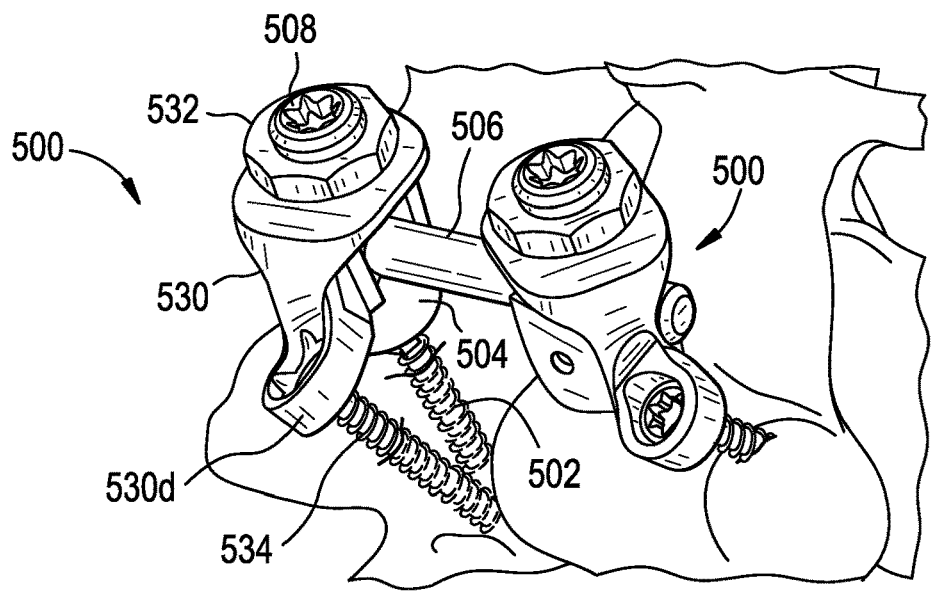
FIG. 3A is a perspective view of a bone anchor assembly and a spinal rod attached to a spine.
Figure 3B:
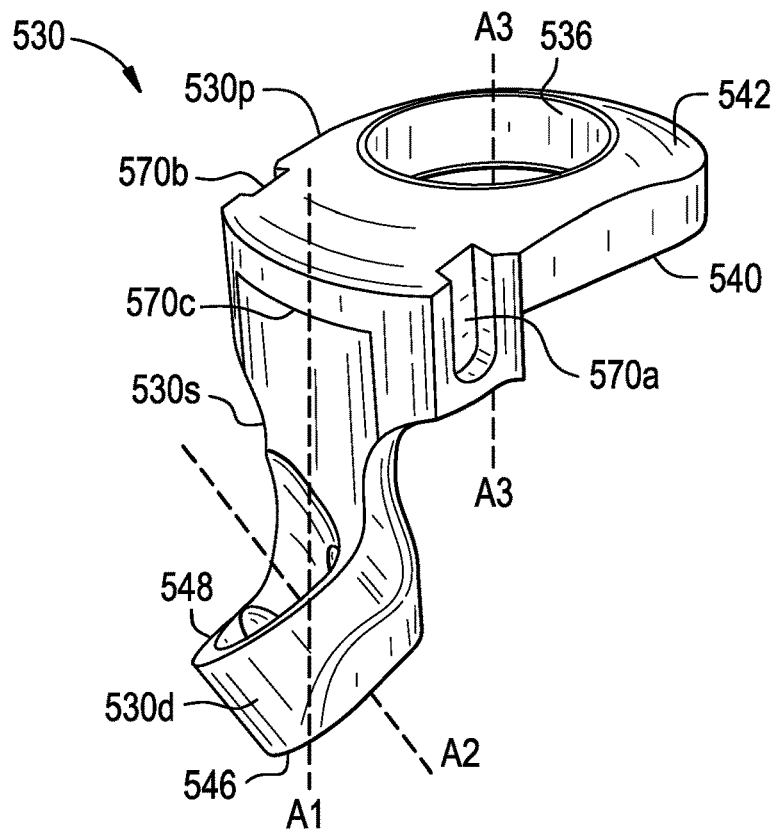
FIG. 3B is a perspective view of a wing of the bone anchor assembly of FIG. 3A.
Figure 3C:
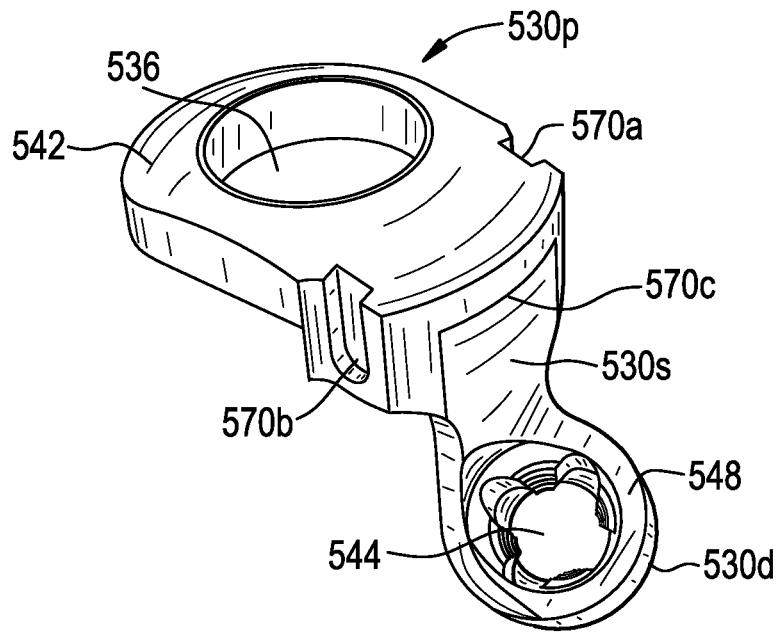
FIG. 3C is another perspective view of a wing of the bone anchor assembly of FIG. 3A.
Figure 3D:
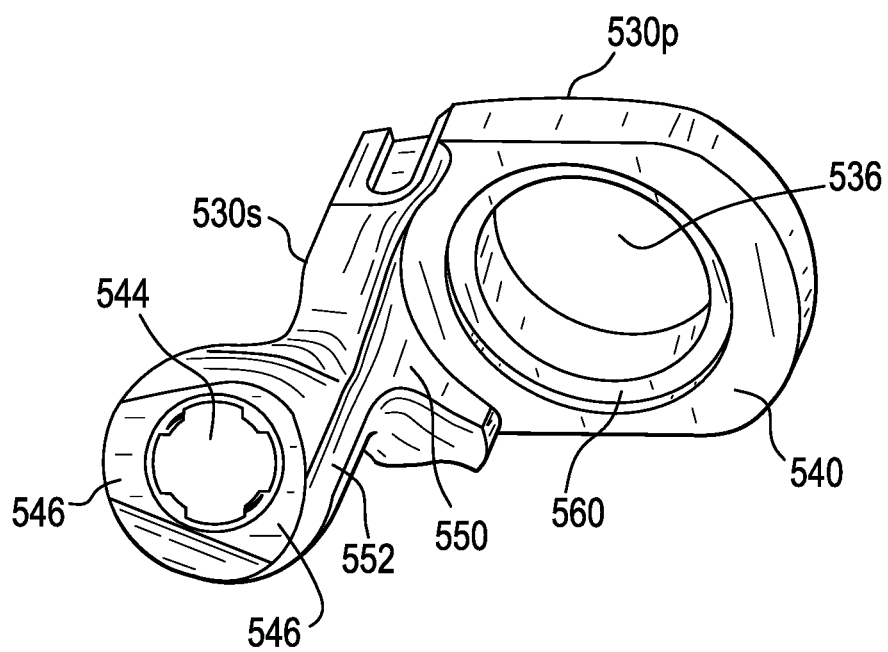
FIG. 3D is another perspective view of a wing of the bone anchor assembly of FIG. 3A.
Figure 3E:
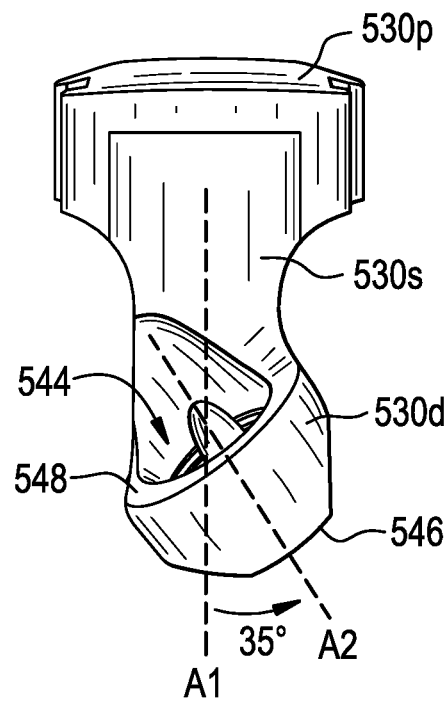
FIG. 3E is a side view of a wing of the bone anchor assembly of FIG. 3A.

When viewed from the perspective of FIG. 3E, the angled distal portion 530d is angled to the right of the vertically-disposed spanning portion 530s of the wing 530. As shown, the angled distal portion 530d includes a distal surface 546 and a proximal surface 548. The distal surface 546 and the proximal surface 548 can be oriented in parallel or substantially in parallel. The distal-facing surface 546 can include teeth, texturing, or other surface features to enhance grip with the adjacent bone. The distal portion 530d of the wing 530 can have a lateral surface 552 that abuts or faces a sidewall of the receiver member 504. The lateral surface 552 can form a negative of the sidewall of the receiver member 504, such that the distal-portion 530d of the wing 530 can hug the receiver member with minimal or zero gap there between. For example, the lateral surface 552 can be concave with a radius of curvature equal or substantially equal to a radius of curvature of the exterior sidewall of the receiver member 504.

The distal portion 530d of the wing 530 can define an opening 544 that extends through the proximal surface 548 and the distal surface 546 to receive an auxiliary bone anchor 534. The bone anchor opening 544 can be sized to insert a distal shaft of the auxiliary bone anchor 534 through the opening and to abut the proximal head of the auxiliary bone anchor when disposed therein. As shown in the illustrated embodiment, the bone anchor opening 544 can be oriented perpendicular or substantially perpendicular to the distal surface 546 of the wing 530. In other arrangements, the nominal or central axis of the bone anchor opening can be obliquely angled relative to the distal surface 546 and/or the proximal surface 548. The distal surface 546 of the wing 530 and/or the proximal surface 548 of the wing can be obliquely angled relative to a vertical or proximal-distal axis of the wing. For example, as shown, the distal surface 546 is angled to face to the right of the vertically-disposed spanning portion 530s. In such embodiments, the central axis A2 of the bone anchor opening 544 can extend at an oblique angle, down and to the right, with respect to a proximal-distal axis A1 of the spanning portion 530s of the wing. This arrangement can facilitate various bone anchor placements in which the distal end of the auxiliary bone anchor is to the right of the spanning portion 530s of the wing when viewed from the perspective of FIG. 3A.

For example, as shown in FIG. 3A, such bone anchor placements can include ones in which the wing 530 is disposed laterally to a spinal rod 506 and in which the auxiliary bone anchor 534 is driven through the bone anchor opening 544 with a cephalad trajectory (i.e., towards a patient's head). This orientation can allow the auxiliary bone anchor 534 to remain wholly within the same vertebral level as the primary bone anchor 502, for example within a lateral mass of the vertebra. It will be appreciated that the wing 530 can be flipped around to be positioned on the other side of the illustrated rod 506 (e.g., on a medial side of the rod), or to be positioned laterally to a contralateral spinal rod (not shown). In these cases, the positioning of the wing 530 can facilitate bone anchor placements in which the auxiliary bone anchor 534 can be driven through the bone anchor opening 544 with a caudal trajectory (i.e., towards a patient's feet). In some embodiments, as discussed further below with respect to FIG. 5A, a caudal trajectory can allow for fixation of the auxiliary bone screw 534 into multiple cortical bone layers, e.g., at least two, at least three, or more. The angled distal portion 530d can allow for the above described bone anchor placements while maintaining the distal surface 546 of the wing 530 in contact with or in close proximity to the bone surface (e.g., within 0 to 3 mm).

In some embodiments, depending on the requirements of the particular application, the distal surface 546 of the wing 530 can be obliquely angled to fix the central axis A2 of the bone anchor opening 544 at any oblique angle to the right of the spanning portion 530s of the wing 530. For example, as shown in FIG. 3E, the distal surface 546 of the distal portion 530d of the wing 530 can be obliquely angled, such that the central axis A2 of the bone anchor opening 544 extends at an angle of 35 degrees to the right of the proximal-distal axis A1 of the spanning portion 530s of the wing 530. Thus, an auxiliary bone anchor 534 can be readily disposed in the bone anchor opening 544 with the distal shaft of the anchor having an angular trajectory coaxial with, or within a defined cone of angulation with respect to, the central axis A2 of the bone anchor opening 544 to the right of the spanning portion 530s. In some embodiments, the distal surface 546 of the wing 530 can be obliquely angled, such that the central axis A2 of the bone anchor opening 544 can extend at an angle between 15 to 45 degrees inclusive to the right of the proximal-distal axis A1 of the spanning portion 530s.

Figure 3F:
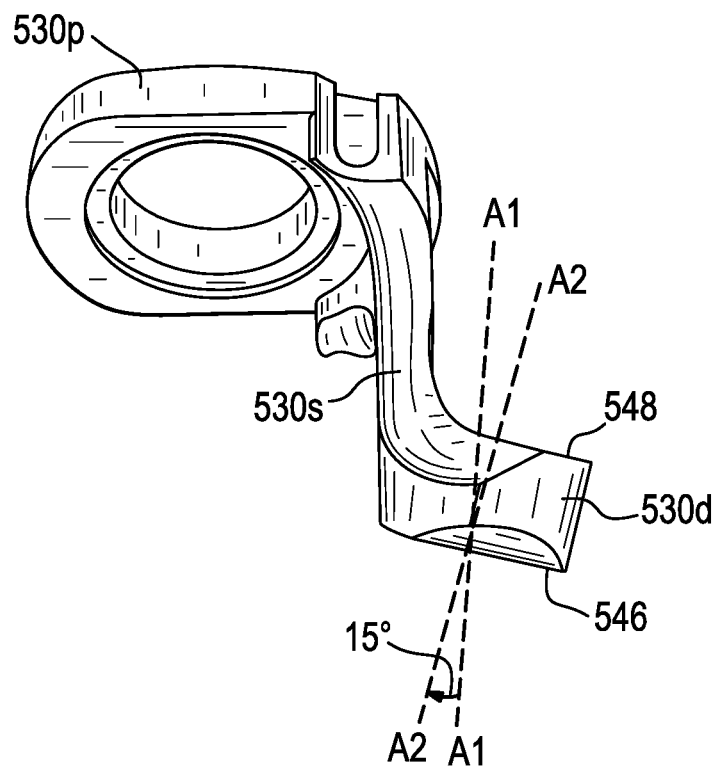
FIG. 3F is another perspective view of a wing of the bone anchor assembly of FIG. 3A.

In some embodiments, the distal surface 546 of the wing 530 can be further angled to face inward or outward with respect to the vertically-disposed spanning portion 530s of the wing 530. By angling the distal surface 546 inward or outward, the distal portion 530d can facilitate auxiliary bone anchor placements through the bone anchor opening 544 having a medial or lateral trajectory component in addition to or instead of a cephalad or caudal trajectory component. In some embodiments, angling the distal surface 546 inward or outward can facilitate bone anchor placements in which the auxiliary bone anchor 534 is secured within the lateral mass of a vertebra. In some embodiments, angling the distal surface 546 of the wing 530 inward or outward can provide clearance for a driver instrument on the proximal surface 548 side of the distal portion 530d of the wing 530 to access the bone anchor opening 544. In some embodiments, based on the requirements of the particular application, the distal surface 546 of the wing 530 can be obliquely angled inward or outward to fix the central axis A2 of the bone anchor opening 544 at any medial or lateral angle with respect to a proximal-distal axis A1 of the spanning portion 530s of the wing 530. For example, as shown in FIG. 3F, the distal surface 546 of the distal portion 530d of the wing 530 can be angled to face inward towards the spanning portion 530s of the wing 530, such that the central axis A2 of the bone anchor opening 544 extends inward at a medial angle of 15 degrees with respect to the proximal-distal axis A1 of the spanning portion 530s. Thus, an auxiliary bone anchor 534 can be readily disposed in the bone anchor opening 544 with the distal shaft of the anchor having a medial trajectory coaxial with, or within a defined cone of angulation with respect to, the central axis A2 of the bone anchor opening 544. In some embodiments, the distal surface 546 of the distal portion 530d of the wing 530 can be obliquely angled, such that the central axis A2 of the bone anchor opening 544 can extend at a medial angle between 5 to 20 degrees inclusive.

Figure 3G:
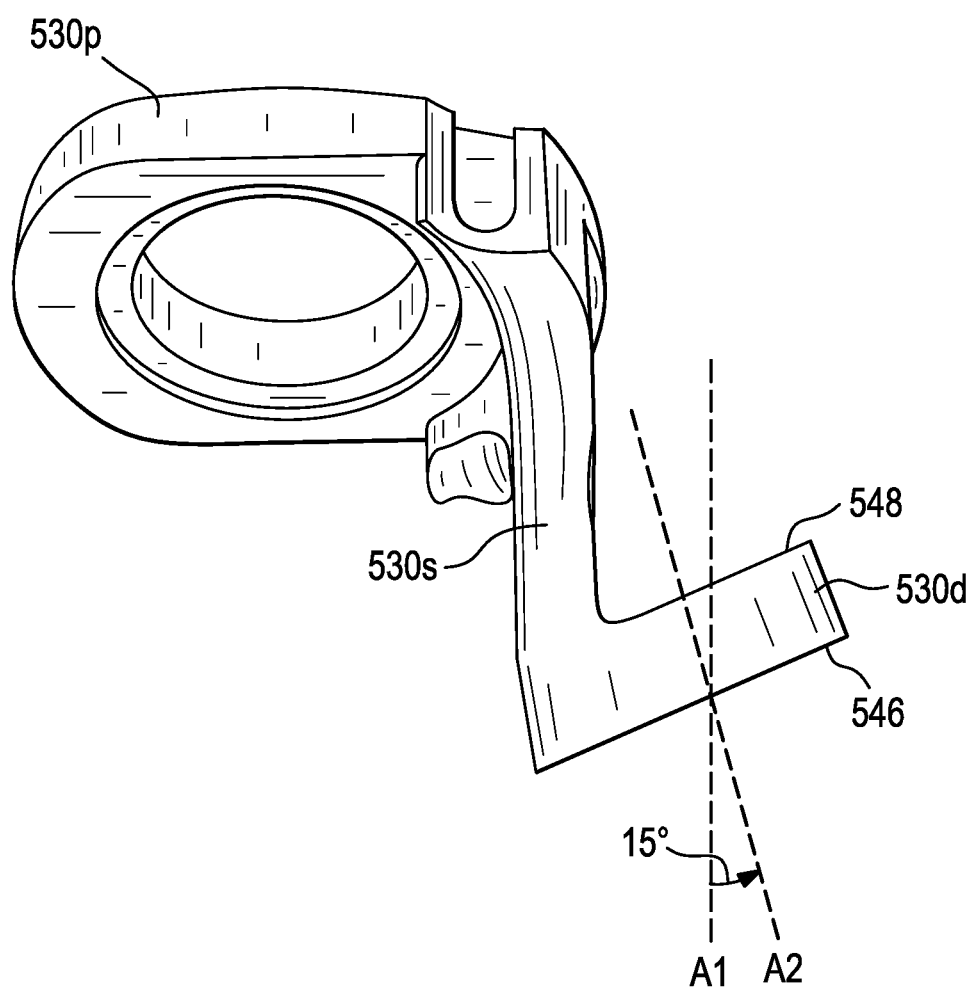
FIG. 3G is another perspective view of a wing of the bone anchor assembly of FIG. 3A.

Alternatively, as shown in FIG. 3G, the distal surface 546 of the distal portion 530d of the wing 530 can be angled to face outward away from the spanning portion 530s, such that the central axis A2 of the bone anchor opening 544 extends outward at a lateral angle of 15 degrees with respect to the proximal-distal axis A1 of the spanning portion 530s of the wing 530. Thus, an auxiliary bone anchor 534 can be readily disposed in the bone anchor opening 544 with the distal shaft of the anchor having a lateral trajectory coaxial with, or within a defined cone of angulation with respect to, the central axis A2 of the bone anchor opening 544. In some embodiments, the distal surface 546 of the distal portion 530d of the wing 530 can be obliquely angled, such that the central axis A2 of the bone anchor opening 544 can extend at a lateral angle between 5 to 20 degrees inclusive. Such embodiments can be useful to accommodate the bony anatomy of the lumbar spine.

Figure 3H:
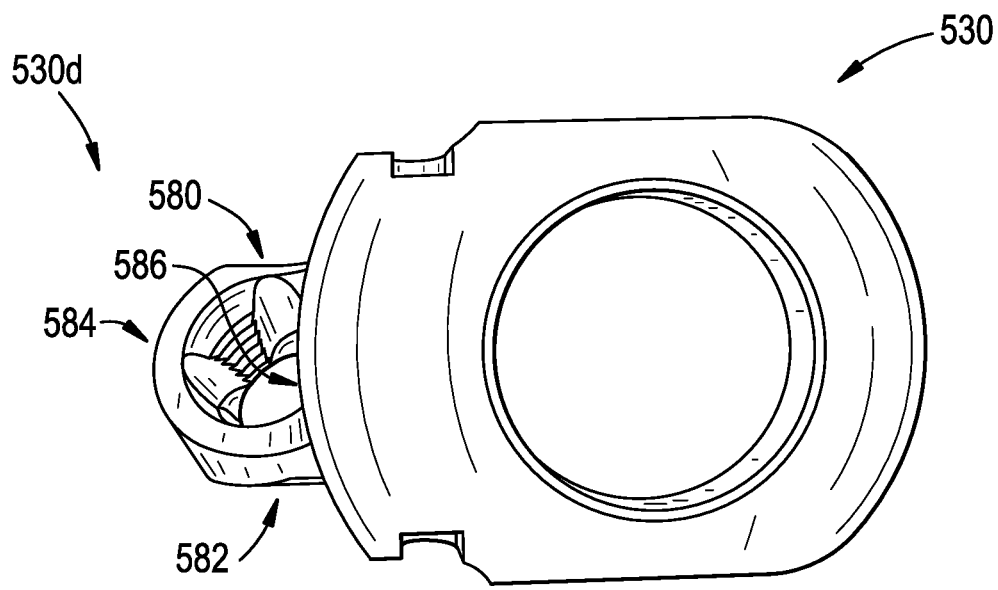
FIG. 3H is a top view of a wing of the bone anchor assembly of FIG. 3A with the angled distal portion facing in a caudal direction.

FIG. 3H is a top view of the wing 530 of the bone anchor assembly of FIG. 3A with the angled distal portion 530d facing in a caudal direction. As shown in FIG. 3H, from a posterior viewpoint, the wing 530 can be positioned with the angled distal portion 530d extending laterally relative to the left of the spinal midline and thus facing in a caudal direction. In this exemplary caudal configuration, the angled distal portion 530d of the wing 530 has a superior end 580, an inferior end 582, a free lateral end 584 extending between the superior and inferior ends, and a medial end 586 extending between the superior and inferior ends. With the angled distal portion 530d facing caudally, the superior end 580 of the distal portion 530d is more distal (or lower) than the inferior end 582, such that the distal surface 546 faces in the caudal direction. In some embodiments, when the distal portion 530d is also angled medially (e.g., as discussed above in FIG. 3F), the superior end 580 of the distal portion 530d is more distal than the inferior end 582 and the free lateral end 584 is more distal than the medial end, such that the distal surface 546 faces in both caudal and medial directions. In some embodiments, when the distal portion 530d is also angled laterally (e.g., as discussed above in FIG. 3G), the superior end 580 of the distal portion 530d is more distal than the inferior end 582 and the medial end 586 is more distal than the free lateral end 584, such that the distal surface 546 faces in both caudal and lateral directions.

Figure 3I:
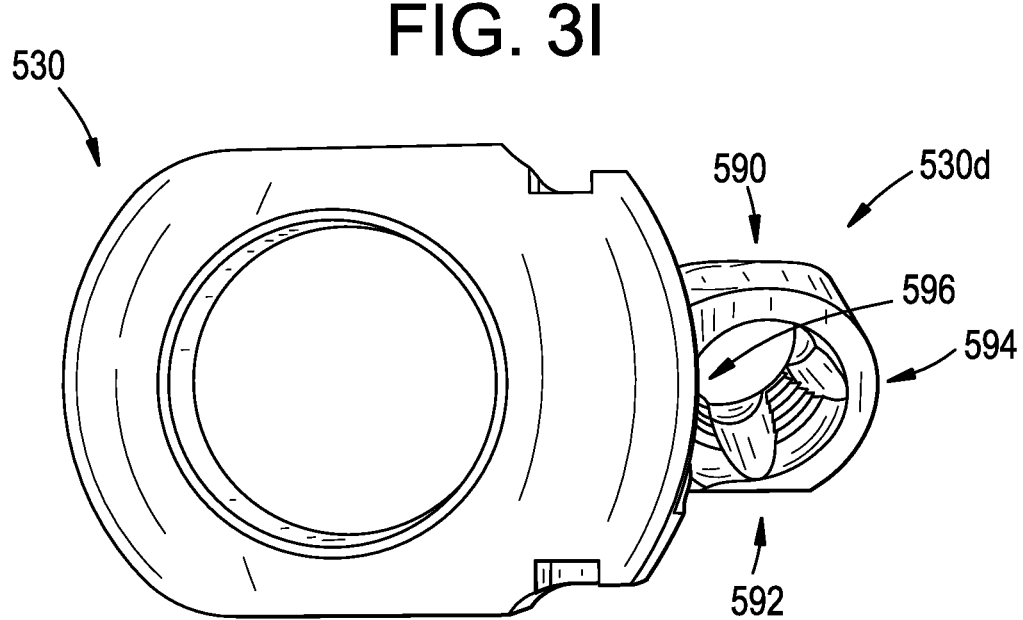
FIG. 3I is a top view of a wing of the bone anchor assembly of FIG. 3A with the angled distal portion facing in a cephalad direction.

FIG. 3I is a top view of the wing 530 of the bone anchor assembly of FIG. 3A with the angled distal portion 530d facing in a cephalad direction. As shown in FIG. 3I, from a posterior viewpoint, the wing 530 can be positioned with the angled distal portion 530d extending laterally relative to the right of the spinal midline and thus facing in a cephalad direction. In this exemplary cephalad configuration, the angled distal portion 530d of the wing 530 has a superior end 590, an inferior end 592, a free lateral end 594 extending between the superior and inferior ends, and a medial end 596 extending between the superior and inferior ends. With the distal portion 530d facing cephalically, the inferior end 592 of the distal portion 530d is more distal (or lower) than the superior end 590, such that the distal surface 546 faces in a cephalad direction. In some embodiments, when the distal portion 530d is also angled medially (e.g., as discussed above in FIG. 3F), the inferior end 592 of the distal portion 530d is more distal (or lower) than the superior end 590 and the free lateral end 594 is more distal than the medial end 596, such that the distal surface 546 faces in both cephalad and medial directions. In some embodiments, when the distal portion 530d is also angled laterally (e.g., as discussed above in FIG. 3G), the inferior end 592 of the distal portion 530d is more distal (or lower) than the superior end 590 and the medial end 596 is more distal than the free lateral end 594, such that the distal surface 546 faces in both cephalad and lateral directions.

In some embodiments, the bone anchor opening 544 can include any of a number of features for accepting bone anchors 534 at varying angles. For example, as discussed above with respect to FIG. 2A-2M, the bone anchor opening 544 can be at least partially threaded to receive a variable-angle locking screw having a threaded proximal head. As shown, the opening 544 can have a plurality of columns of threads spaced apart to define a plurality of non-threaded recesses. In the illustrated embodiment, the opening 544 has four columns of threads. The columns of threads can be arranged around the inner surface of the opening 544 for engaging threads on the head of a locking auxiliary bone anchor and/or a variable-angle locking auxiliary bone anchor. The auxiliary bone anchor 534 can thus be locked with the wing 530 coaxially with the central axis A2 of the opening 544 or at a selected angle within a range of selectable angles relative to the central axis A2 of the opening 544. The auxiliary bone anchor 534 can include features to facilitate this variable-angle locking, such as a proximal head that is at least partially spherical having a thread with a profile that follows the arc-shaped radius of curvature of the spherical portion of the head. The variable-angle capability of the screw/opening interface can allow the user to place a locking auxiliary bone anchor into the bone at any angle within defined angulation limits. In some embodiments, the interior surface of the opening 544 can be smooth or spherical, without threads or locking features.

In some embodiments, the proximal-most extent of each auxiliary bone anchor 534 can be distal to the spinal rod 506. In other embodiments, the proximal-most extent of each auxiliary bone anchor 534 can be distal to the distal-most extent of the receiver member 504. These configurations can advantageously reduce the overall profile of the assembly 500. The wing 500 can be Z-shaped or substantially Z-shaped. While one bone anchor opening 544 is shown in the illustrated embodiment, it will be appreciated that the wing 530 can include any number of bone anchor openings (e.g., one, two, three, four, five, and so on).

Figure 4A:
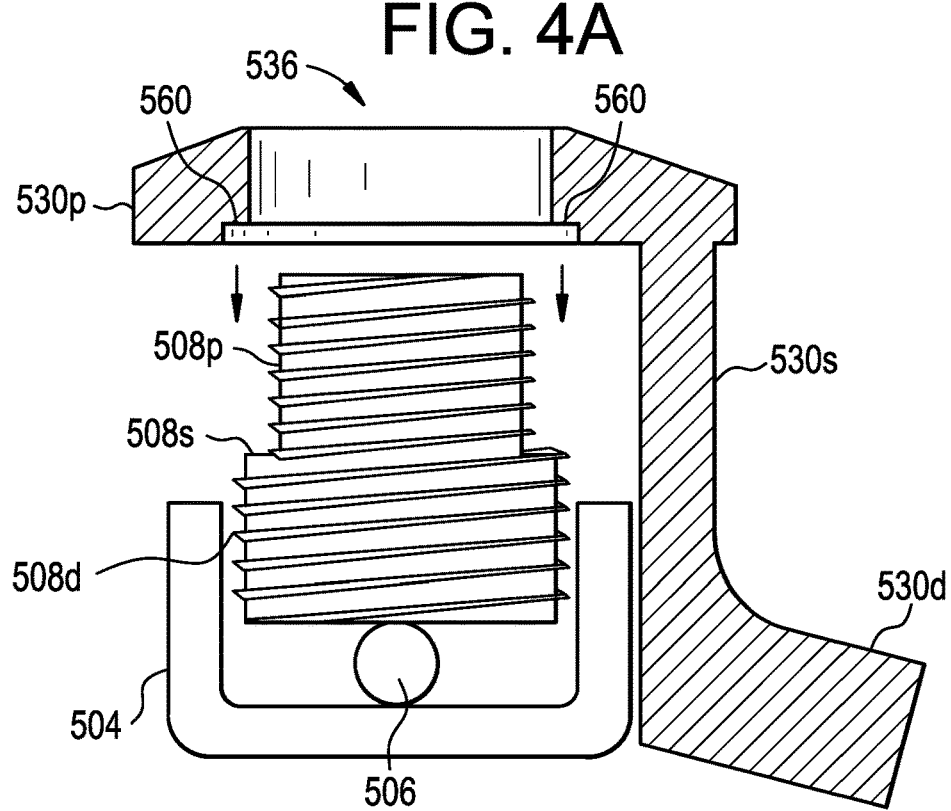
FIG. 4A is a cross sectional view of a wing of the bone anchor assembly of FIG. 3A prior to being secured to a closure mechanism.
Figure 4B:
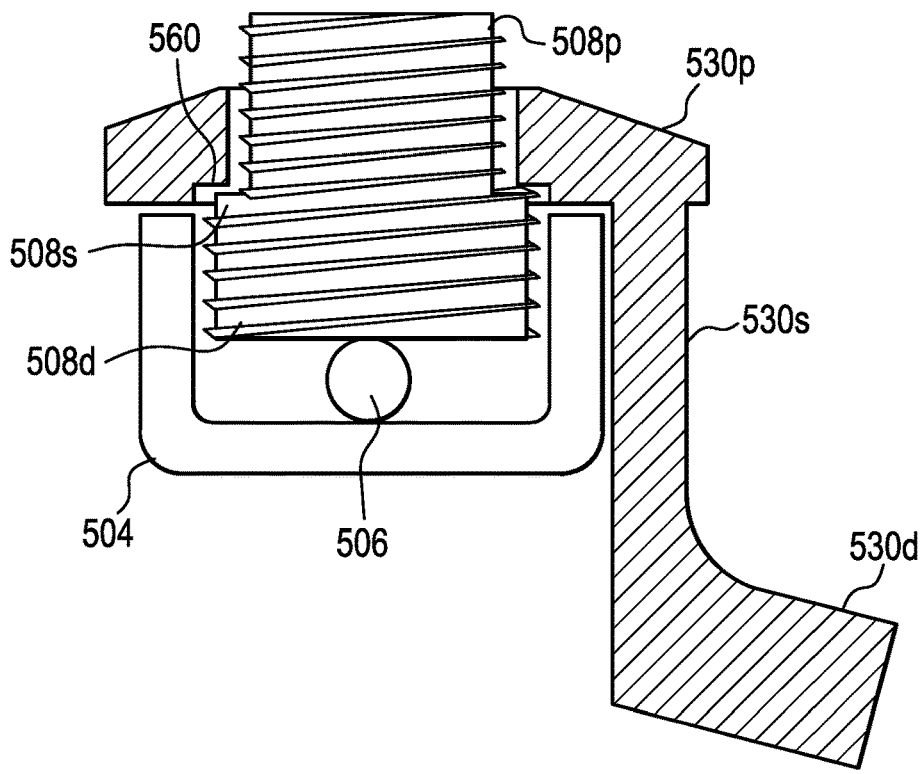
FIG. 4B is a cross sectional view of the wing of FIG. 4A secured to a closure mechanism.
Figure 4C:
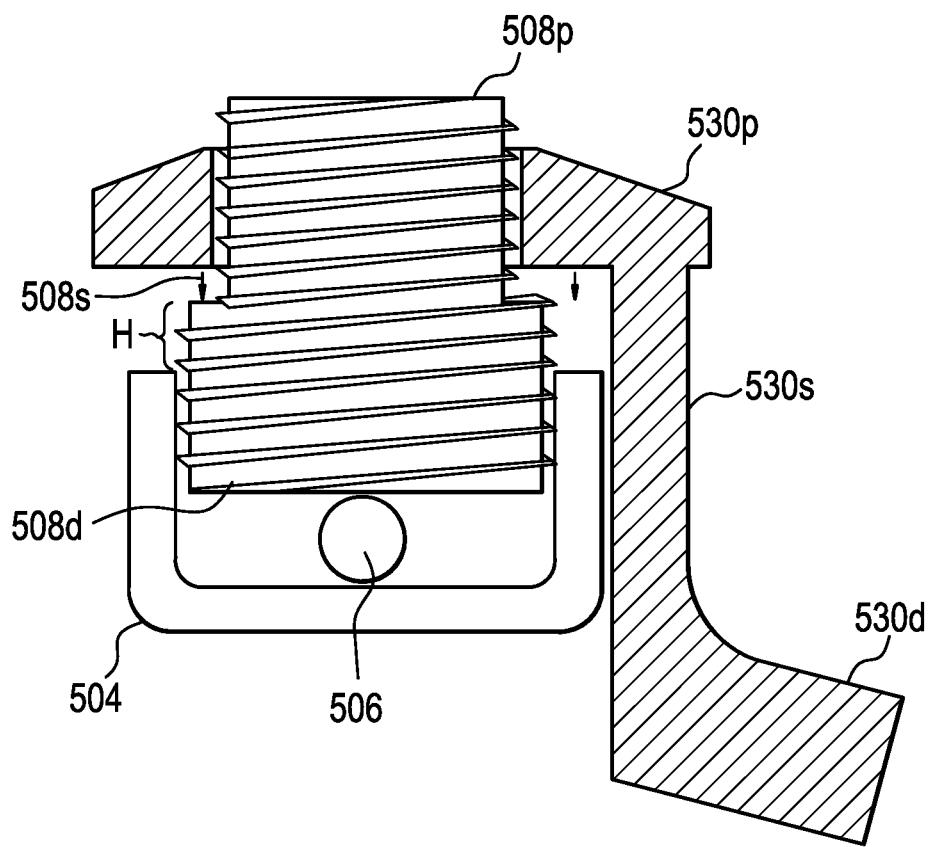
FIG. 4C is another cross-sectional view of the wing of FIG. 4A secured to a closure mechanism.

FIG. 4A-4C are cross-sectional views illustrating the wing or bracket 530 secured to the bone anchor assembly 500 of FIG. 3A-3H. As discussed above, the proximal portion 530p of the wing can include a distal-facing surface 542 configured to bear against a proximal terminal end or surface of the receiver member 504 when the wing 530 is secured to the receiver member. For example, in some embodiments, the closure mechanism 508 can be in the form of a threaded post having an enlarged-diameter distal portion 508d and a reduced-diameter proximal portion 508p. The distal portion 508d of the closure mechanism 508 can be threaded into the receiver member 504 to engage a spinal rod 506 disposed in the receiver member. The proximal portion 508p of the closure mechanism 508 can protrude above the receiver member 504, e.g., above a proximal-facing terminal end or surface of the receiver member, and through the opening 536 formed in the wing.

However, there can be instances when the distal portion 508d of the closure mechanism 508 may not be fully threaded into the receiver member 504, which can cause the radially-extending shoulder portion 508s of the closure mechanism 508 to protrude above the proximal end of the receiver member 504. In such instances, the shoulder portion 508s of the closure mechanism 508 can abut the proximal portion 530p of the wing 530 distal-facing surface 542 of the wing and thereby prevent the proximal portion 530p from bearing against the receiver member 504. This can cause less reliable and/or inconsistent tightening of the wing 530 to the bone anchor assembly 500.

As shown in the illustrated embodiment of FIGS. 4A and 4B, a counter bore 560 can be formed about the opening 536 in the distal-facing surface 542 of the proximal portion 530p to secure the wing 530 to the bone anchor assembly 500 more consistently. The counter bore 560 can be an annular ring or channel formed around the opening 536. The counter bore 560 can be sized to accommodate the width of the shoulder portion 508s. The depth or height of the counter bore 560 can be configured to at least partially receive the shoulder portion 508s that protrudes above the receiver member 504 in order to maintain contact between the proximal portion 530p of the wing 530 and the proximal-facing surface of the receiver member 504. The depth or height of the counter bore 560 can be configured not to exceed a threshold depth or height at which the closure mechanism can become disengaged from the spinal rod and thus compromise fixation of the rod 506 within the receiver member 504. Embodiments including a counter bore can provide more reliable and/or consistent tightening by ensuring that the wing is always tightened to the receiver member, regardless of the vertical position of the closure mechanism.

Alternatively, or additionally, as shown in the illustrated embodiment of FIG. 4C, the closure mechanism 508 can be sized such that the radially-extending shoulder portion 508s is configured to always extend above the receiver member 504. In such embodiments, the distal-facing surface 542 of the proximal portion 530d of the wing 530 bears against the radially-extending shoulder portion 508s of the closure mechanism 508 instead of the receiver member 504. For example, as shown in FIG. 4C, the enlarged-diameter distal portion 508d of the closure mechanism 508 can be configured with an extended height H that allows the shoulder portion 508s of the closure mechanism 508 to protrude above the receiver member 504 when in contact with the spinal rod 506. Such embodiments can provide a more reliable and/or consistent tightening of the wing 530 by ensuring that the wing is always tightened to the closure mechanism, regardless of the vertical position of the closure mechanism.

As discussed above, some embodiments of the bone anchor assembly can include a wing having a distal portion angled to the left of the vertically-disposed wing. In such embodiments, an auxiliary bone anchor can be disposed through an opening in the distal portion with caudal or cephalad trajectories similar to those facilitated by the wing 530 of the bone anchor assembly 500 when implanted on the opposite side of the patient's spine (i.e., the left hand side of the patient).

FIGS. 5A through 5F illustrate an exemplary embodiment of a bone anchor assembly 700 that includes a bracket or wing 730 having an angled distal portion 730d. As shown, the bone anchor assembly 700 includes a bone anchor 702, a receiver member 704, a closure mechanism 708, a bracket or wing 730, a nut 732 and an auxiliary bone anchor 734. Except as described below or as will be readily appreciated by one having ordinary skill in the art, the bone anchor 702, the receiver member 704, the closure mechanism 708, the nut 732, and the auxiliary bone anchor 734 are substantially similar to the bone anchor 202, the receiver member 204, the closure mechanism 208, the nut 232, and the auxiliary bone anchors 234 described above with respect to FIGS. 2A-2M. A detailed description of the structure and function thereof is thus omitted here for the sake of brevity. The bone anchor assembly 700 can include any one or more of the features of one or more of the bone anchor assemblies described above.

As shown in FIGS. 5A through 5F, the bracket or wing 730 can include a proximal portion 730p, an angled distal portion 730d, and a spanning portion 730s that connects the proximal portion to the distal portion of the wing. Except as described below or as will be readily appreciated by one having ordinary skill in the art, the proximal portion 730p and the spanning portion 730s of the wing 730 are substantially similar to the proximal portion 530p and the spanning portion 530s of the wing 530 described above with respect to FIGS. 3A-3I and FIGS. 4A-4C. A detailed description of the structure and function thereof is thus omitted here for the sake of brevity. The wing 730 can include any one or more of the features of the wing 500 described above.

Figure 5A:
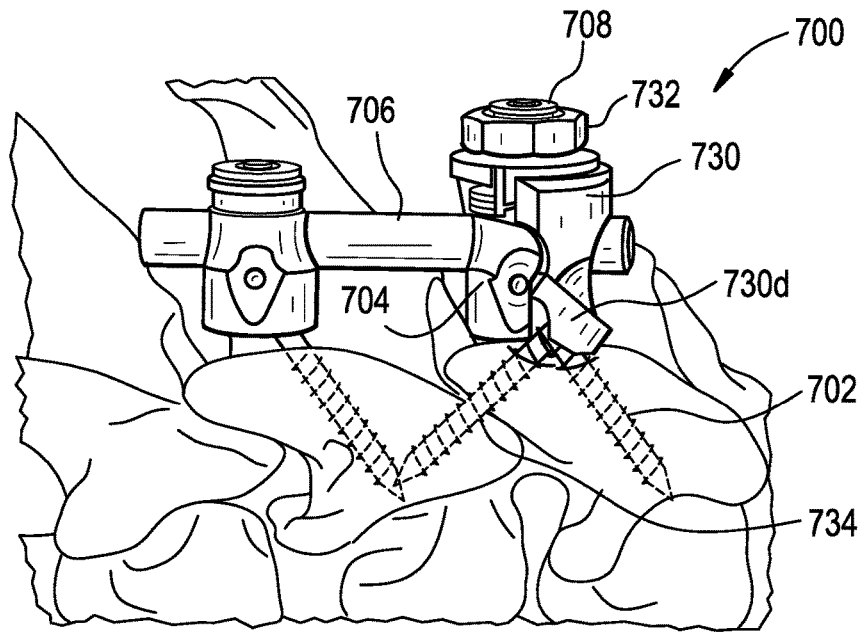
FIG. 5A is a perspective view of a bone anchor assembly and a spinal rod attached to a spine.
Figure 5B:
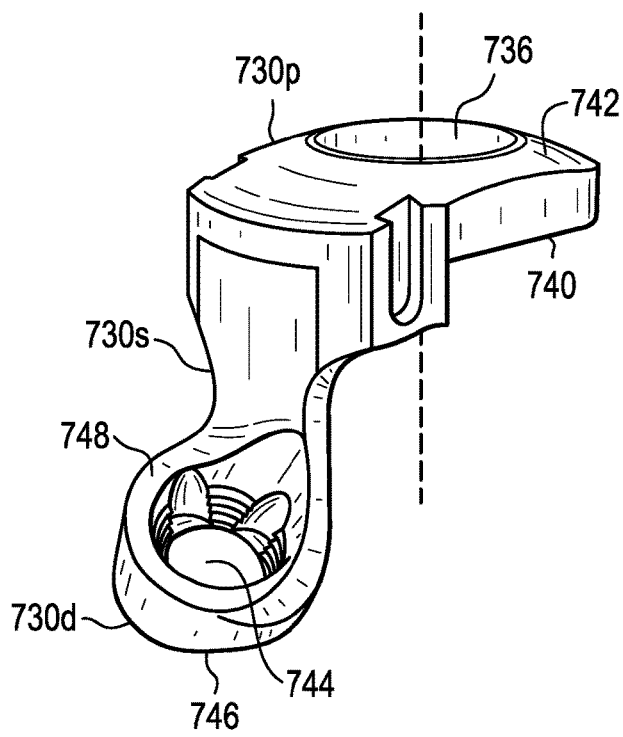
FIG. 5B is a perspective view of a wing of the bone anchor assembly of FIG. 5A.
Figure 5C:
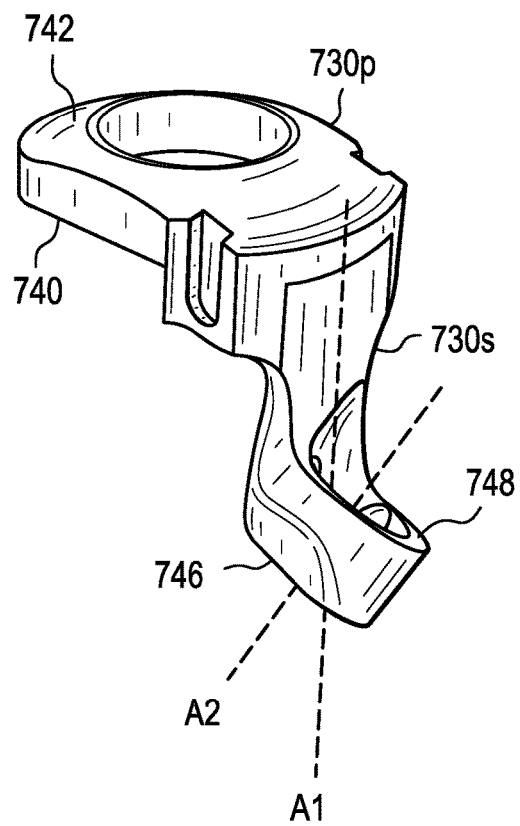
FIG. 5C is another perspective view of a wing of the bone anchor assembly of FIG. 5A.
Figure 5D:
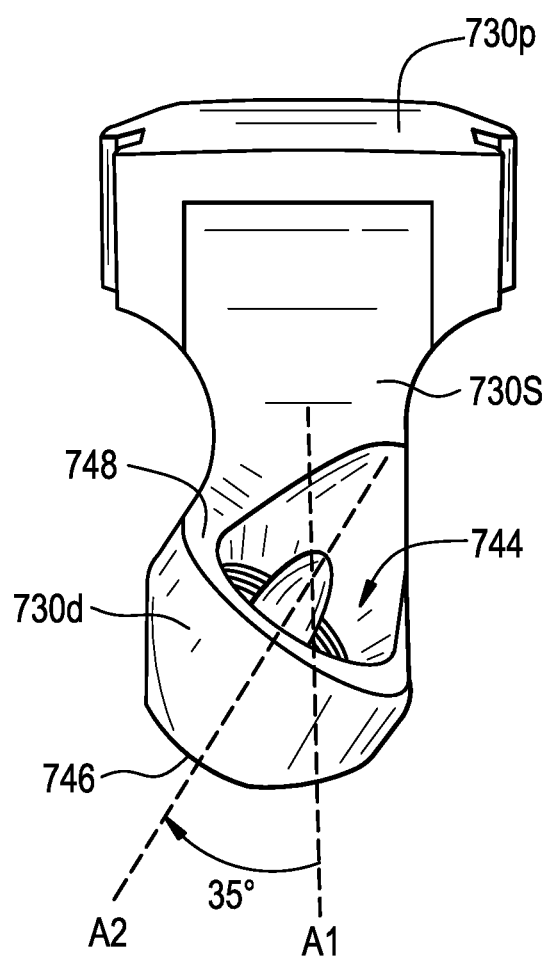
FIG. 5D is a side view of a wing of the bone anchor assembly of FIG. 5A.

In the illustrated embodiment, the distal portion 730d of the wing 730 is substantially similar to the distal portion 530d of the wing 500, except that the distal portion 730d is angled to the left of the vertically-disposed spanning portion 730s (when viewed from the perspective of FIG. 5D). As shown, the angled distal portion 730d can include a distal surface 746 and a proximal surface 748 that can be oriented in parallel or substantially in parallel. The distal portion 730d of the wing 730 can define an opening 744 that extends through the proximal surface 748 and the distal surface 746 to receive an auxiliary bone anchor 534. As shown in the illustrated embodiment, the bone anchor opening 744 can be oriented perpendicular or substantially perpendicular to the distal surface 746 of the wing 730. In other arrangements, the nominal or central axis of the bone anchor opening can be obliquely angled relative to the distal surface 746 and/or the proximal surface 748. The distal surface 746 of the wing 730 and/or the proximal surface 748 of the wing can be obliquely angled relative to a vertical or proximal-distal axis of the wing. For example, as shown, the distal surface 546 is angled to face to the left of the vertically-disposed spanning portion 730s. In such embodiments, the central axis A2 of the bone anchor opening 744 can extend at an oblique angle, down and to the left, with respect to the proximal-distal axis A1 of the spanning portion 730s of the wing. This arrangement can facilitate various bone anchor placements in which the distal end of the auxiliary bone anchor is to the left of the spanning portion 530s of the wing when viewed from the perspective of FIG. 5A.

For example, as shown in FIG. 5A, such bone anchor placements can include ones in which the wing 730 is disposed laterally to a spinal rod 506 and in which the auxiliary bone anchor 534 is driven through the bone anchor opening 744 with a caudal trajectory (i.e., towards a patient's feet). This orientation can allow the auxiliary bone anchor 534 to extend into one or more adjacent vertebral levels, e.g., across a facet joint. A caudal trajectory can allow for fixation of the auxiliary bone screw 534 into multiple cortical bone layers, e.g., at least two, at least three, or more. For example, as shown in FIG. 5A, with the primary bone anchor 502 positioned in a superior vertebral level, the bone anchor assembly 700 can effect tri-cortical fixation with the auxiliary bone anchor 534 crossing a facet joint between the superior vertebral level and an adjacent inferior vertebral level. It will be appreciated that the wing 730 can be flipped around to be positioned on the other side of the illustrated rod 506 (e.g., on a medial side of the rod), or to be positioned laterally to a contralateral spinal rod (not shown). In these cases, the positioning of the wing 530 can facilitate bone anchor placements in which the auxiliary bone anchor 534 can be driven through the bone anchor opening 744 with a cephalad trajectory (i.e., towards a patient's head). As discussed above with respect to FIG. 3A, a cephalad trajectory can allow the auxiliary bone anchor 534 to remain wholly within the same vertebral level as the primary bone anchor 502, for example within a lateral mass of the vertebra. The angled distal portion 730d can allow for the above-described bone anchor placements while maintaining the distal surface 746 of the wing 730 in contact with or in close proximity to the bone surface (e.g., within 0 to 3 mm).

In some embodiments, depending on the requirements of the particular application, the distal surface 746 of the wing 730 can be obliquely angled to fix the central axis A2 of the bone anchor opening 744 at any oblique angle to the left of the spanning portion 730s of the wing 730. For example, as shown in FIG. 5D, the distal surface 746 of the distal portion 730d of the wing 730 can be obliquely angled, such that the central axis A2 of the bone anchor opening 744 extends at an angle of 35 degrees to the left of the proximal-distal axis A1 of the spanning portion 730s of the wing 730. Thus, an auxiliary bone anchor 534 can be readily disposed in the bone anchor opening 744 with the distal shaft of the anchor having an angular trajectory coaxial with, or within a defined cone of angulation with respect to, the central axis A2 of the bone anchor opening 744 to the left of the spanning portion 730s. In some embodiments, the distal surface 746 of the wing 730 can be obliquely angled, such that the central axis A2 of the bone anchor opening 744 can extend at an angle between 15 to 45 degrees inclusive to the left of the proximal-distal axis A1 of the spanning portion 730s.

As discussed above with respect to FIGS. 3F and 3G, in some embodiments, the distal surface 746 of the wing 730 can be further angled to face inward or outward with respect to the vertically-disposed spanning portion 730s of the wing 730. In some embodiments, based on the requirements of the particular application, the distal surface 746 of the wing 730 can be obliquely angled inward or outward to fix the central axis A2 of the bone anchor opening 744 at any medial or lateral angle between 5 and 20 degrees inclusive with respect to a proximal-distal axis A1 of the spanning portion 730s of the wing 730. Thus, by angling the distal surface 746 inward or outward, the distal portion 730d can facilitate placement of the auxiliary bone anchor 534 having a medial or lateral trajectory component in addition to or instead of a cephalad or caudal trajectory component through the bone anchor opening 744. In some embodiments, angling the distal surface 746 inward or outward can facilitate bone anchor placements in which the auxiliary bone anchor 534 is secured within the lateral mass of a vertebra. In some embodiments, angling the distal surface 746 of the wing 730 inward or outward can provide clearance for a driver instrument on the proximal surface 748 side of the distal portion 730d of the wing 730 to access the bone anchor opening 744.

Figure 5E:
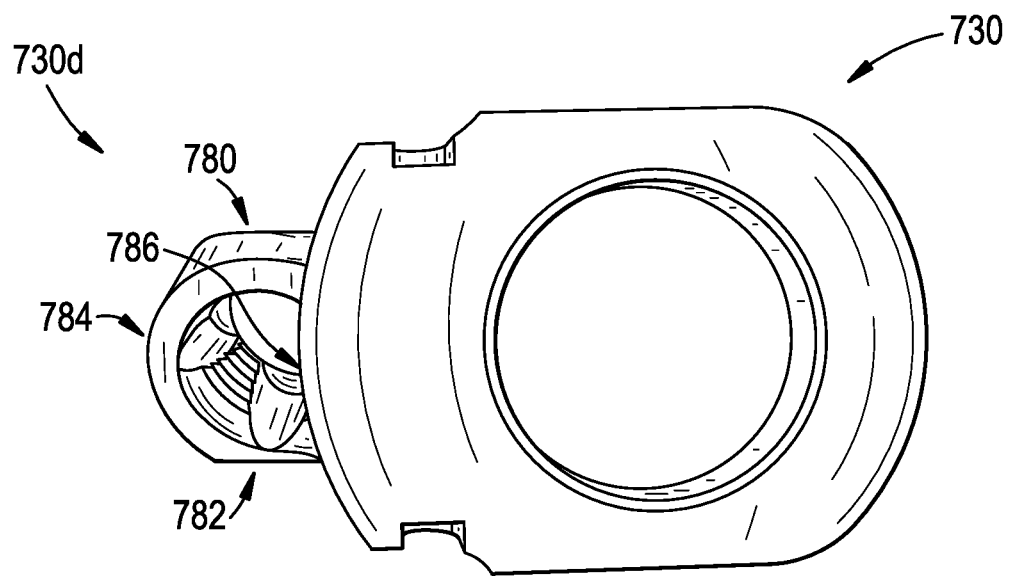
FIG. 5E is a top view of a wing of the bone anchor assembly of FIG. 5A with the angled distal portion facing in a cephalad direction.

FIG. 5E is a top view of the wing 730 of the bone anchor assembly of FIG. 5A with the angled distal portion 730d facing in a cephalad direction. As shown in FIG. 5E, from a posterior viewpoint, the wing 730 can be positioned with the distal portion 730d extending laterally relative to the left of the spinal midline and thus facing in a cephalad direction. In this exemplary cephalad configuration, the angled distal portion 730d of the wing 730 has a superior end 780, an inferior end 782, a free lateral end 784 extending between the superior and inferior ends, and a medial end 786 extending between the superior and inferior ends. With the distal portion 730d facing cephalically, the inferior end 782 of the distal portion 730d is more distal (or lower) than the superior end 780, such that the distal surface 746 faces in a cephalad direction. In some embodiments, when the distal portion 730d is also angled medially (e.g., as discussed above in FIG. 3G), the inferior end 782 of the distal portion 730d is more distal (or lower) than the superior end 780 and the free lateral end 784 is more distal than the medial end 786, such that the distal surface 746 faces in both cephalad and medial directions. In some embodiments, when the distal portion 730d is also angled laterally (e.g., as discussed above in FIG. 3H), the inferior end 782 of the distal portion 730d is more distal (or lower) than the superior end 780 and the medial end 786 is more distal than the free lateral end 784, such that the distal surface 746 faces in both cephalad and lateral directions.

Figure 5F:
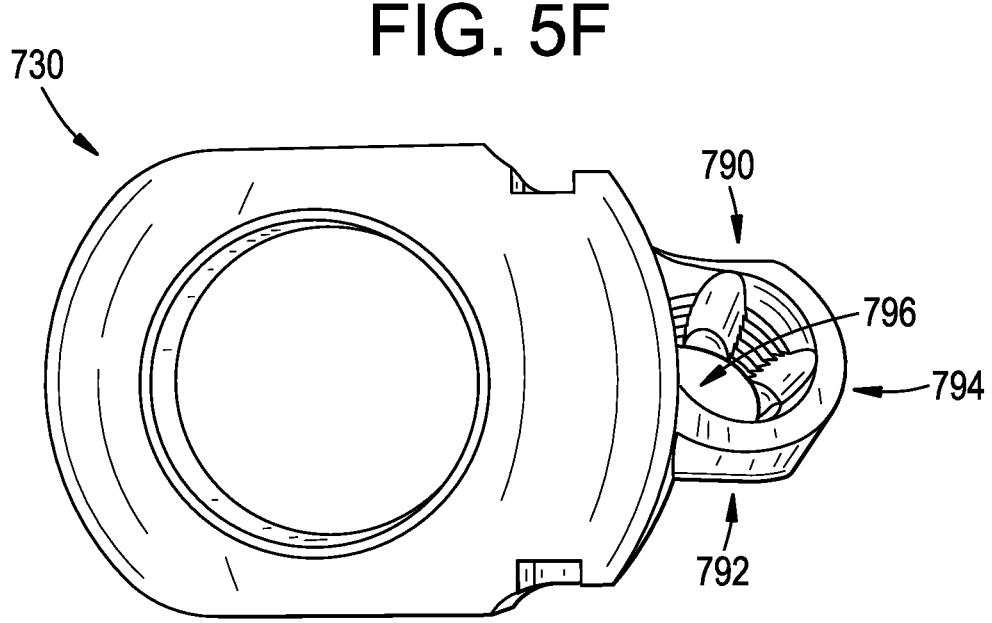
FIG. 5F is a top view of a wing of the bone anchor assembly of FIG. 5A with the angled distal portion facing in a caudal direction.

FIG. 5F is a top view of the wing 730 of the bone anchor assembly of FIG. 5A with the angled distal portion 730d facing in a caudal direction. As shown in FIG. 5F, from a posterior viewpoint, the wing 730 can be positioned with the angled distal portion 730d extending laterally relative to the right of the spinal midline and thus facing in a caudal direction. In this exemplary caudal configuration, the angled distal portion 730d of the wing 730 has a superior end 790, an inferior end 792, a free lateral end 794 extending between the superior and inferior ends, and a medial end 796 extending between the superior and inferior ends. With the angled distal portion 730d facing caudally, the superior end 790 of the distal portion 730d is more distal (or lower) than the inferior end 792, such that the distal surface 746 faces in the caudal direction. In some embodiments, when the distal portion 730d is also angled medially (e.g., as discussed above in FIG. 3G), the superior end 790 of the distal portion 730d is more distal than the inferior end 792 and the free lateral end 794 is more distal than the medial end 796, such that the distal surface 746 faces in both caudal and medial directions. In some embodiments, when the distal portion 730d is also angled laterally (e.g., as discussed above in FIG. 3H), the superior end 790 of the distal portion 730d is more distal than the inferior end 792 and the medial end 796 is more distal than the free lateral end 794, such that the distal surface 746 faces in both caudal and lateral directions.

As discussed above, some embodiments of the bone anchor assembly can include a wing having a distal portion angled inward or outward with respect to the vertically-disposed spanning portion without any right or left angulation. In such embodiments, an auxiliary bone anchor can be readily disposed through a bone anchor opening in the distal portion with a medial trajectory or a lateral trajectory.

FIGS. 6A through 6E illustrate an exemplary embodiment of a bracket or wing 830 of a bone anchor assembly having an angled distal portion 830d. As shown, the bracket or wing 830 can include a proximal portion 830p, an angled distal portion 830*d*, and a spanning portion 830*s* that connects the proximal portion to the distal portion. The angled distal portion 830*d* has a free lateral end 850 and a medial end 852. Except as described below or as will be readily appreciated by one having ordinary skill in the art, the proximal portion 830*p* and the spanning portion 830*s* of the wing 830 are substantially similar to the proximal and spanning portions of the wing 230, 530, and/or 730 described above with respect to FIGS. 2A-2M, 3A-3I, and 5A-5F. A detailed description of the structure and function thereof is thus omitted here for the sake of brevity. The wing 830 can include any one or more of the features of the wings 230, 530 and/or 730 described above.

In the illustrated embodiment, the distal portion 830*d* of the wing 830 is substantially similar to the angled distal portions 530*d*, 730*d* disclosed above with respect to FIGS. 3A-3I and 5A-5F, except that the distal portion 830*d* is angled inward towards the vertically-disposed spanning portion 830*s* without angulation to the right or left of the wing 830*s*. The angled distal portion 830*d* of the wing 830 includes a distal surface 846 and a proximal surface 848. The distal surface 846 and the proximal surface 848 can be tilted down in parallel or substantially in parallel. When the distal portion 830*d* is angled inward (or medially when viewed from the perspective of FIG. 6B), the free lateral end 850 is more distal than the medial end 852, such that the distal surface 846 faces in a medial direction.

The distal portion 830*d* of the wing 830 can define one or more openings 844 that extend through the proximal surface 848 and the distal surface 846 to receive an auxiliary bone anchor 534. As shown in the illustrated embodiment, the bone anchor openings 844 can be oriented perpendicular or substantially perpendicular to the distal surface 846 of the wing 830. The distal surface 846 of the wing 830 can be obliquely angled to face inward towards the vertically-disposed spanning portion 830*s* of the wing 830 to fix the central axis A2 of the bone anchor opening 844 at a medial angle with respect to the proximal-distal axis A1 of the spanning portion 830*s*. Thus, an auxiliary bone anchor 534 can be readily disposed in the bone anchor opening 844 with the distal shaft of the auxiliary bone anchor 534 having a medial trajectory coaxial with, or within a defined cone of angulation with respect to, central axis A2 of the bone anchor opening.

Figure 6A:
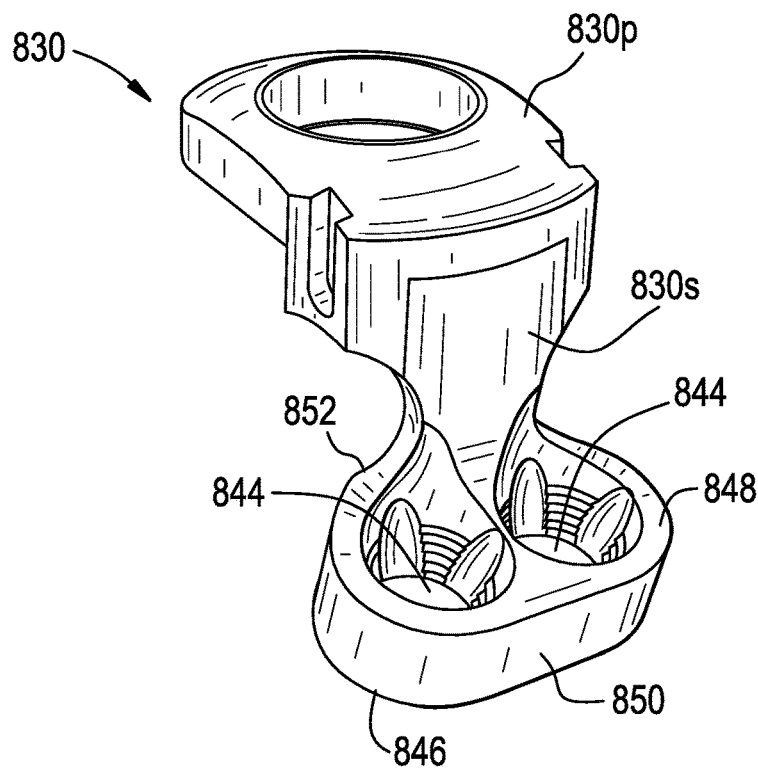
FIG. 6A is a perspective view of a wing of bone anchor assembly.
Figure 6B:
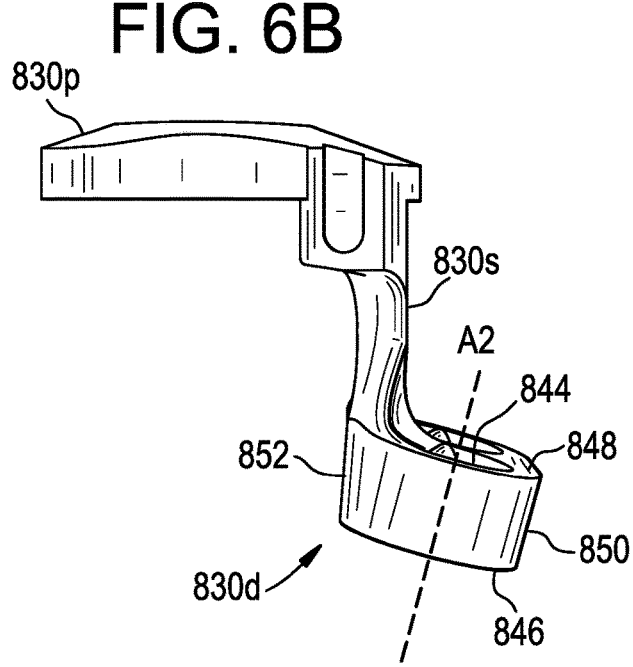
FIG. 6B is a side view of the wing of FIG. 6A.
Figure 6C:
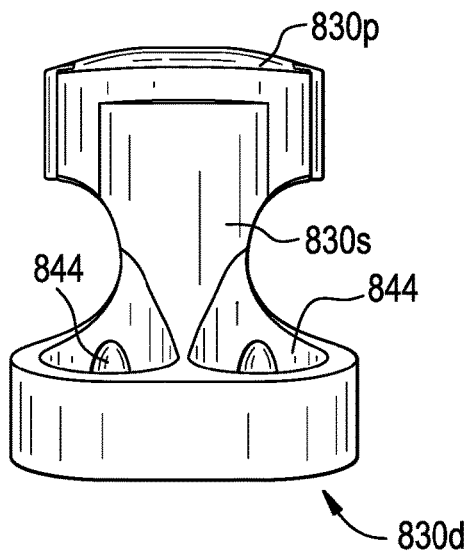
FIG. 6C is another side view of the wing of FIG. 6A.
Figure 6D:
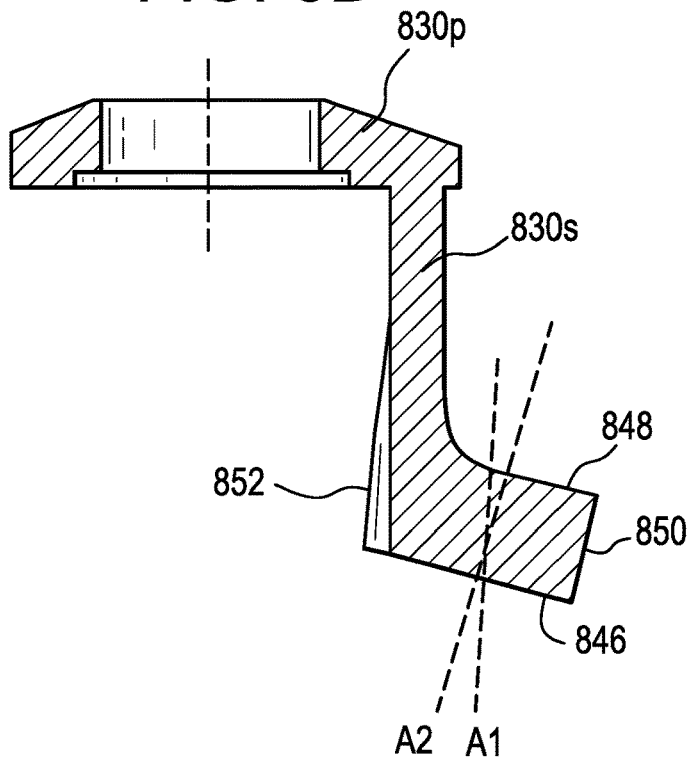
FIG. 6D is a sectional side view of the wing of FIG. 6A.

For example, in the illustrated embodiment of FIG. 6D, the distal surface 846 of the distal portion 830*d* of the wing 830 can be angled to face inward towards the spanning portion 830*s*, such that the central axis A2 of the bone anchor opening 844 extends inward at an angle of 15 degrees with respect to the proximal-distal axis A1. Thus, the auxiliary bone anchor 534 can be readily disposed in the bone anchor opening 844 with the distal shaft of the anchor having an medial trajectory of 15 degrees with respect to the proximal-distal axis A1. In some embodiments, the distal surface 846 of the distal portion 830*d* of the wing 830 can be obliquely angled to fix the central axis A2 of the bone anchor opening 844 at a medial angle between 5 to 20 degrees inclusive with respect to the proximal-distal axis A1 of the spanning portion 830*s* of the wing 830. In such embodiments, angling the distal surface 846 inward can facilitate bone anchor placements in which the auxiliary bone anchor 534 is secured within the lateral mass of a vertebra. In some embodiments, angling the distal surface 846 of the wing 830 inward can provide clearance for a driver instrument on the proximal surface 848 side of the distal portion 830*d* of the wing 830 to access the bone anchor opening 544.

Figure 6E:
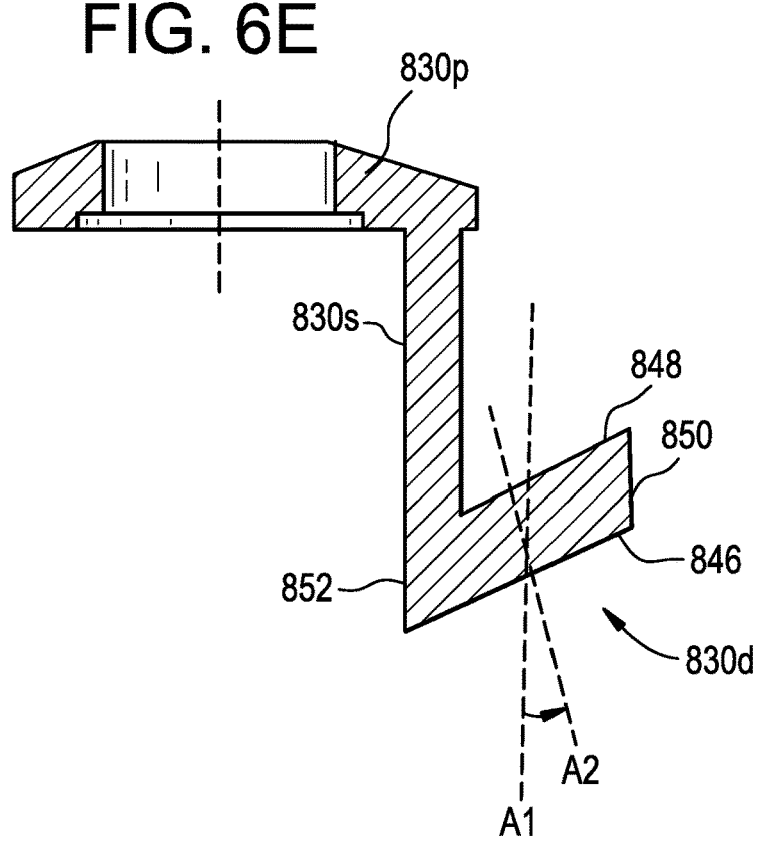
FIG. 6E is another sectional side view of the wing of FIG. 6A.

In an alternative embodiment shown in FIG. 6E, the distal portion 830*d* can be angled outward (or laterally, when viewed from the perspective of FIG. 6E), such that the medial end 852 of the distal portion is more distal than the free lateral end 850. In this lateral configuration, the distal surface 846 faces outward away from the spanning portion 830*s* in a lateral direction and the central axis A2 of the bone anchor opening 844 extends outward at a lateral angle with respect to the proximal-distal axis A1 of the spanning portion 830*s* of the wing 830. Thus, an auxiliary bone anchor 534 can be readily disposed in the bone anchor opening 844 with the distal shaft of the anchor having a lateral trajectory coaxial with, or within a defined cone of angulation with respect to, the central axis A2 of the bone anchor opening 844. In some embodiments, the distal surface 846 of the distal portion 830*d* of the wing 830 can be obliquely angled, such that the central axis A2 of the bone anchor opening 844 can extend at a lateral angle between 5 to 20 degrees inclusive (e.g., 15 degrees). In such embodiments, angling the distal surface 846 outward can facilitate bone anchor placements in which the auxiliary bone anchor 534 is secured in a lateral location. Such embodiments can be useful to accommodate the bony anatomy of the lumbar spine.

As discussed above in the embodiment of FIGS. 2A-2M, supplemental fixation of a primary bone anchor in a bone anchor assembly can be accomplished using a wing or bracket having one or more bone anchor openings through which one or more auxiliary bone anchors can be driven into bone. In some instances, however, a surgeon may experience difficulty in making certain bone anchor placements having angular trajectories. Variability in the bony anatomy of the spine can make it difficult to position the distal portion of the wing in close proximity to bone to facilitate proper engagement or purchase with the anchor. Moreover, it can be desirable to insert an auxiliary bone anchor such that the auxiliary bone anchor extends through multiple cortical layers of bone for optimal additional fixation strength. With respect to the embodiments of FIGS. 3A-6E, in some applications an angled distal portion of a wing could interfere with the bony anatomy of the spine or limit optimal placement of an auxiliary bone anchor screw. Moreover, in certain applications it may be advantageous to use a plurality of auxiliary bone anchors to further secure or augment fixation of a primary bone anchor inserted into a vertebral mass. Accordingly, it can be desirable to insert one or more auxiliary bone anchor screws at an angled trajectory to accommodate a particular spinal anatomy and/or surgical application while optimally augmenting the purchase and fixation strength of a primary bone anchor.

In some embodiments of the present disclosure, a wing can have a distal portion defining a plurality of auxiliary bone anchor openings, where each of the auxiliary bone anchor openings can be biased or angled with respect to the distal portion and with respect to a proximal-distal axis of the wing such that an auxiliary bone anchor can be driven into a bony mass at an angular trajectory. In some embodiments, each of the auxiliary bone anchor openings can be angled such that, with the wing secured to the receiver member, an auxiliary bone anchor can be driven into a bony mass at an angular trajectory in a caudal or cephalad direction. By way of non-limiting example, the auxiliary bone anchor openings can extend at an angle with respect to the distal portion and with respect to the proximal-distal axis of the wing such that an auxiliary bone anchor driven with a caudal trajectory can extend closer to a center of the bony mass (e.g., a vertebra or facet thereof), preventing undesirable interaction with an edge of the bony mass. Further, in an auxiliary bone anchor driven with a cephalad trajectory, the angular trajectory can keep the anchor within the bony mass, for example a thin lateral mass of a vertebra. In some embodiments, the wing can be configured such that each of the auxiliary bone anchors can be inserted and extend wholly within a vertebral level into which a primary bone anchor is inserted. In other words, a bone anchor assembly can include a wing that can enable insertion of a plurality of auxiliary bone anchors at an angled trajectory such that the auxiliary bone anchors conform to the vertebral level of the bone anchor assembly without violating or traversing a facet plane. In other embodiments, a wing of the present disclosure can be configured such that at least one of a plurality of auxiliary bone anchors can be inserted with an angular trajectory to violate a facet plane of the vertebral level into which the primary bone anchor is inserted. In some embodiments, an auxiliary bone anchor can extend through multiple cortical levels and into an adjacent vertebra.

FIGS. 7-17 illustrate exemplary embodiments of a bone anchor assembly 900 that includes a bracket or wing 930 having a distal portion 930d that defines a plurality of auxiliary bone anchor openings 944 that can extend at a biased or angled trajectory with respect to both the distal portion and a proximal-distal axis of the wing. As will be discussed in greater detail below, a wing of the present embodiment can facilitate insertion of a plurality of auxiliary bone anchor screws into a vertebral level of the bone assembly. In some embodiments, each of the auxiliary bone anchors can conform to the vertebral level of the bone anchor assembly. Alternatively, the wing can be configured such that at least one auxiliary bone anchor screw can violate a facet plane of the vertebral level of the bone anchor assembly and can extend into an adjacent vertebral level. Accordingly, a bone anchor assembly including a wing of the present disclosure can increase a pullout strength of the primary bone anchor by providing multiple auxiliary fixation points and distributing stresses in the bone. The wing can facilitate insertion of a plurality of auxiliary bone anchors at a desired trajectory to take into account anatomy of a particular spinal region and a particular surgical application. Accordingly, a wing of the present disclosure can provide a surgeon more flexibility with respect to auxiliary bone anchor placement to achieve optimal fixation strength and greater purchase of the primary bone anchor.

Figure 7:
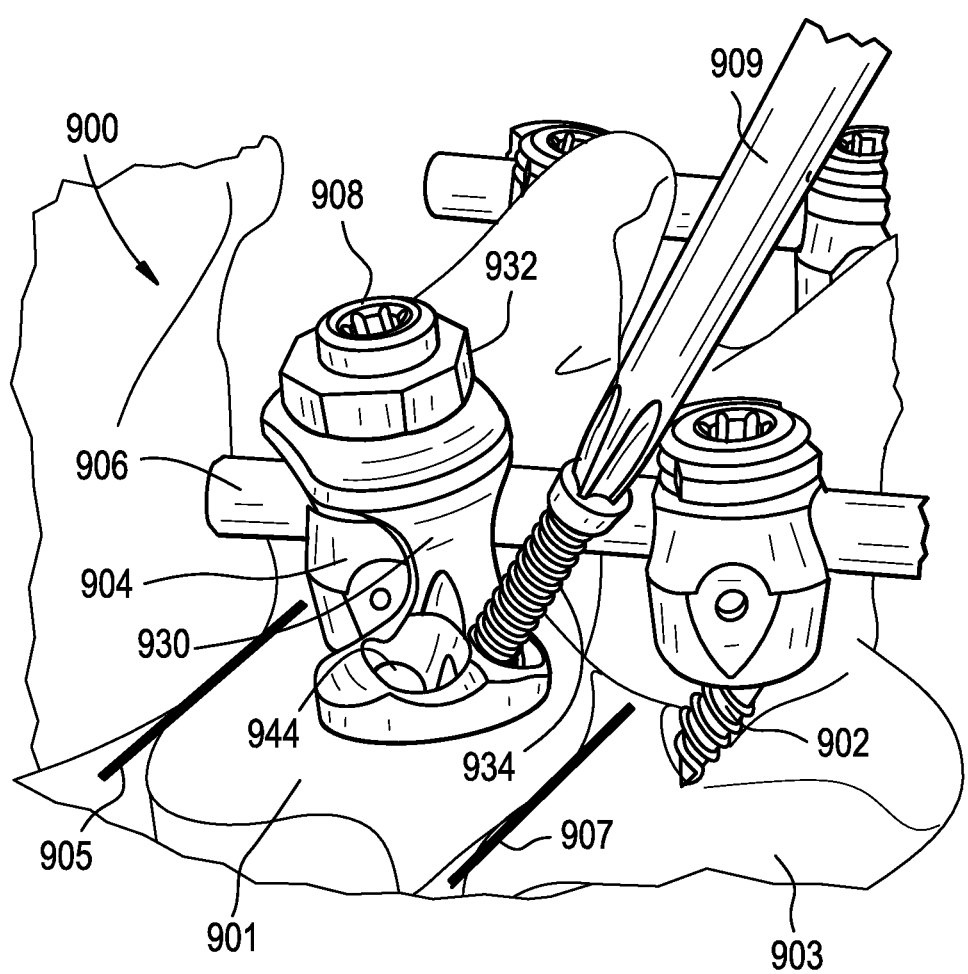
FIG. 7 is perspective view of a bone anchor assembly and a spinal rod attached to a spine.
Figure 8:
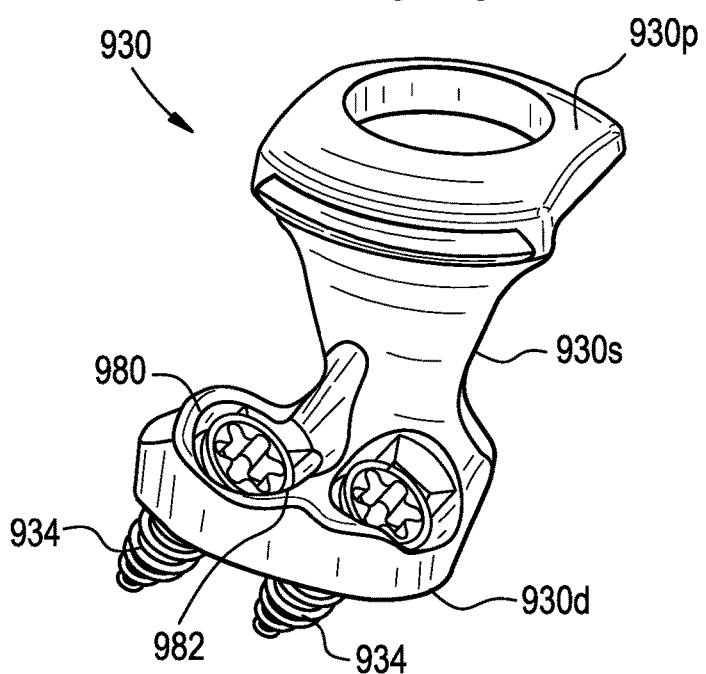
FIG. 8 is a perspective view of one embodiment of a wing of the bone anchor assembly of FIG. 7.

With reference to FIGS. 7 and 8, a bone anchor assembly 900 can be implanted into a vertebral level 901. Vertebral level 901 can have a first facet plane 905 and a second facet plane 907. The bone anchor assembly 900 can include a bone anchor (labeled 902 and visible in a vertebra 903 that is adjacent to the vertebra 901), a receiver member 904, a closure mechanism 908, a bracket or wing 930, a nut 932, and one or more auxiliary bone anchors 934. The wing 930 can be secured to the receiver member 904, e.g., using the closure mechanism 908 and the nut 932. As discussed above, the wing 930 can be rotatable relative to the closure mechanism 908. Prior to securing the wing 930, the wing can be placed in a desired position or configuration with respect to the receiver member. A desired position or configuration of the wing can establish a target insertion trajectory for each of the one or more auxiliary bone anchors 934 to be received with auxiliary bone anchor openings 944. The closure mechanism 908 can be secured to the receiver member 904 to capture a spinal fixation element, e.g., a spinal rod 906, within the receiver member. In some embodiments, tightening or locking the closure mechanism 908 can be effective to fix the spinal rod 906 relative to the receiver member 904, and to fix an angular position of the bone anchor 902 relative to the receiver member 904.

Except as described below or as will be readily appreciated by one having ordinary skill in the art, the bone anchor 902, the receiver member 904, the closure mechanism 908, the nut 932, and the auxiliary bone anchor 934 are substantially similar to the bone anchor 202, the receiver member 204, the closure mechanism 208, the nut 232, and the auxiliary bone anchors 234 described above with respect to FIGS. 2A-2M. A detailed description of the structure and function thereof is thus omitted here for the sake of brevity. The bone anchor assembly 900 can include any one or more of the features of the bone anchor assembly 200, 500, 700, or 800 and/or the bone anchor assembly 100 described above.

Figure 9:
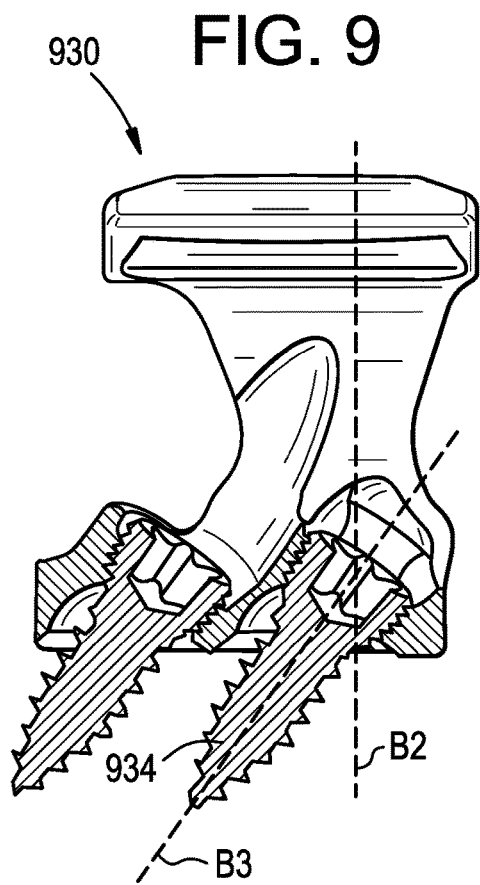
FIG. 9 is a side cross-sectional view of a wing of the bone anchor assembly of FIG. 7.
Figure 10:
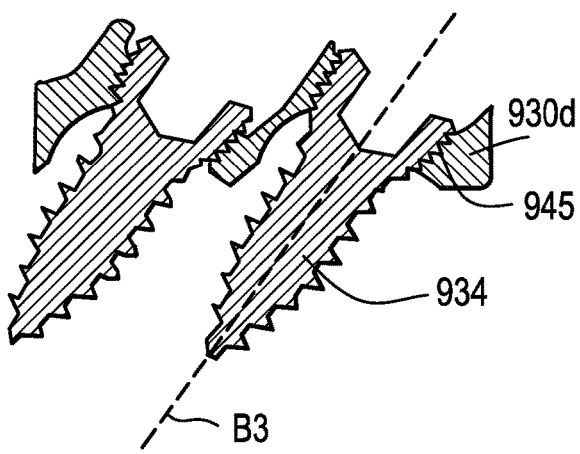
FIG. 10 is a detail cross-sectional view of the wing of FIG. 9.
Figure 11:
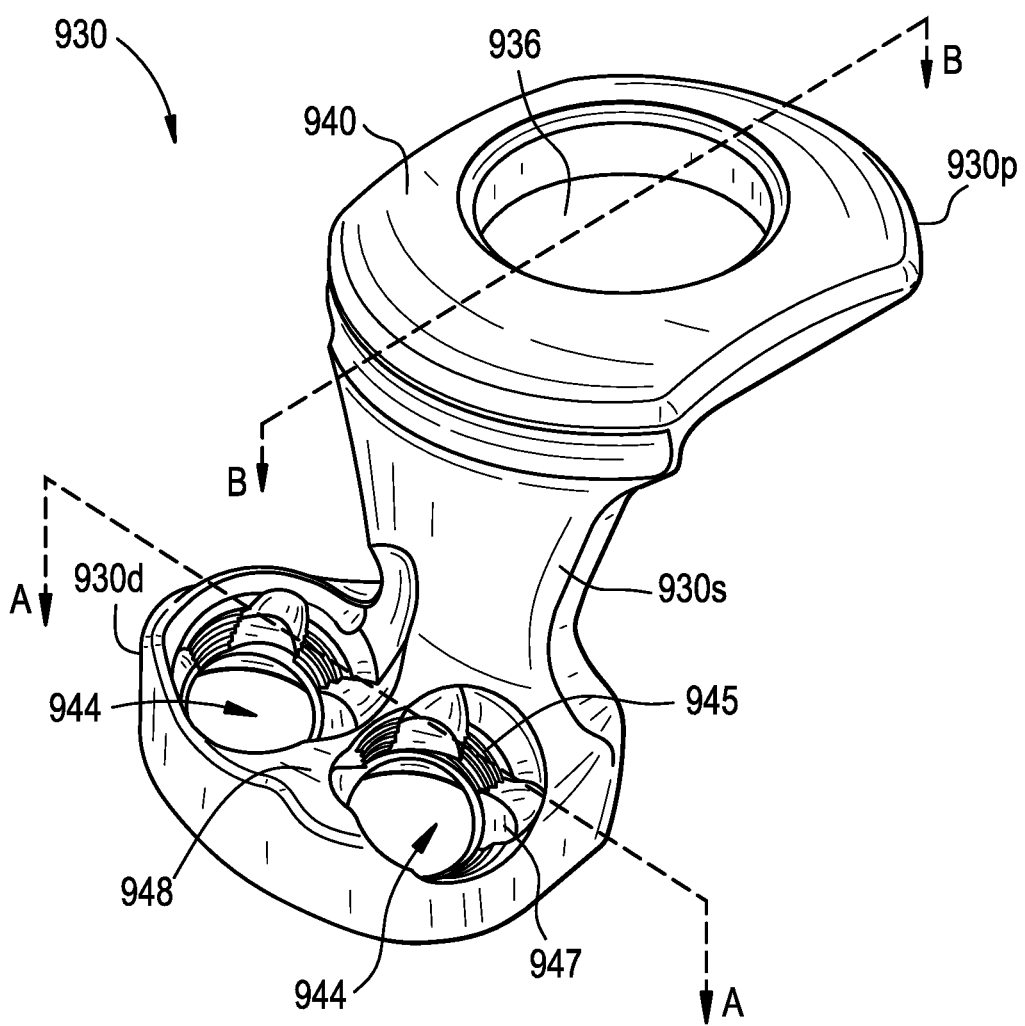
FIG. 11 is a perspective view illustrating a wing of the bone anchor assembly of FIG. 7.
Figure 12:
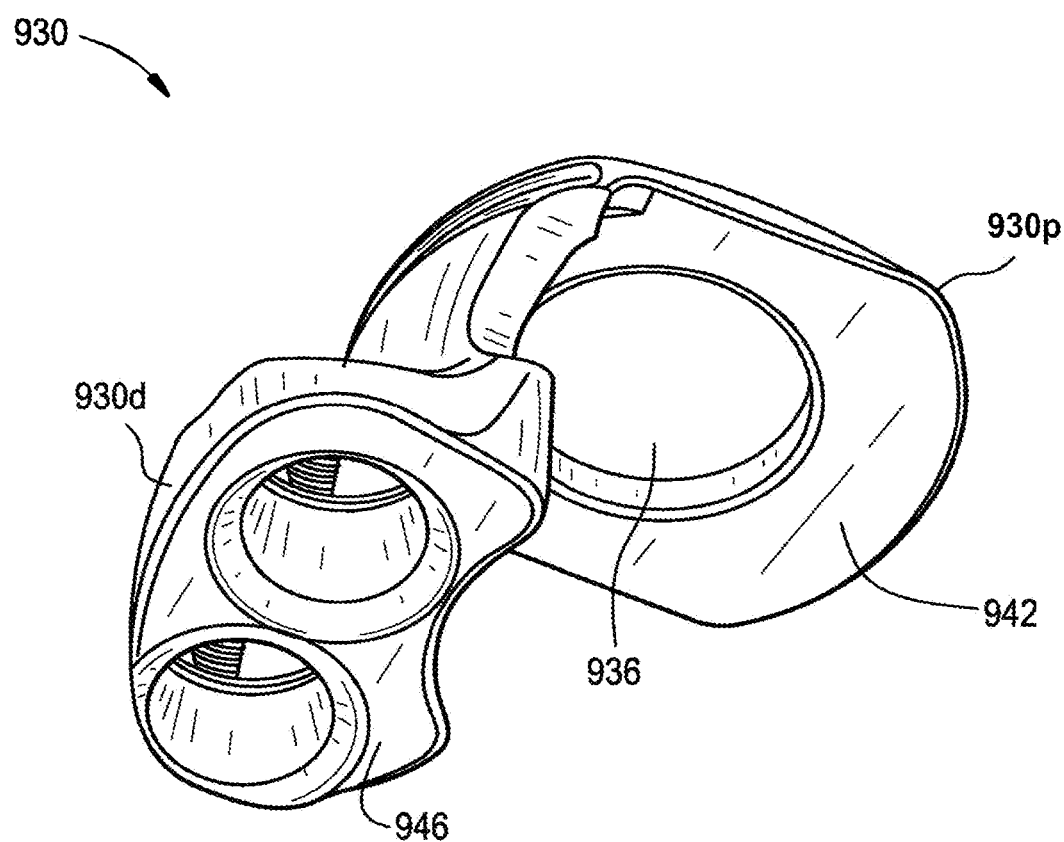
FIG. 12 is another perspective view illustrating a wing of the bone anchor assembly of FIG. 7.
Figure 13:
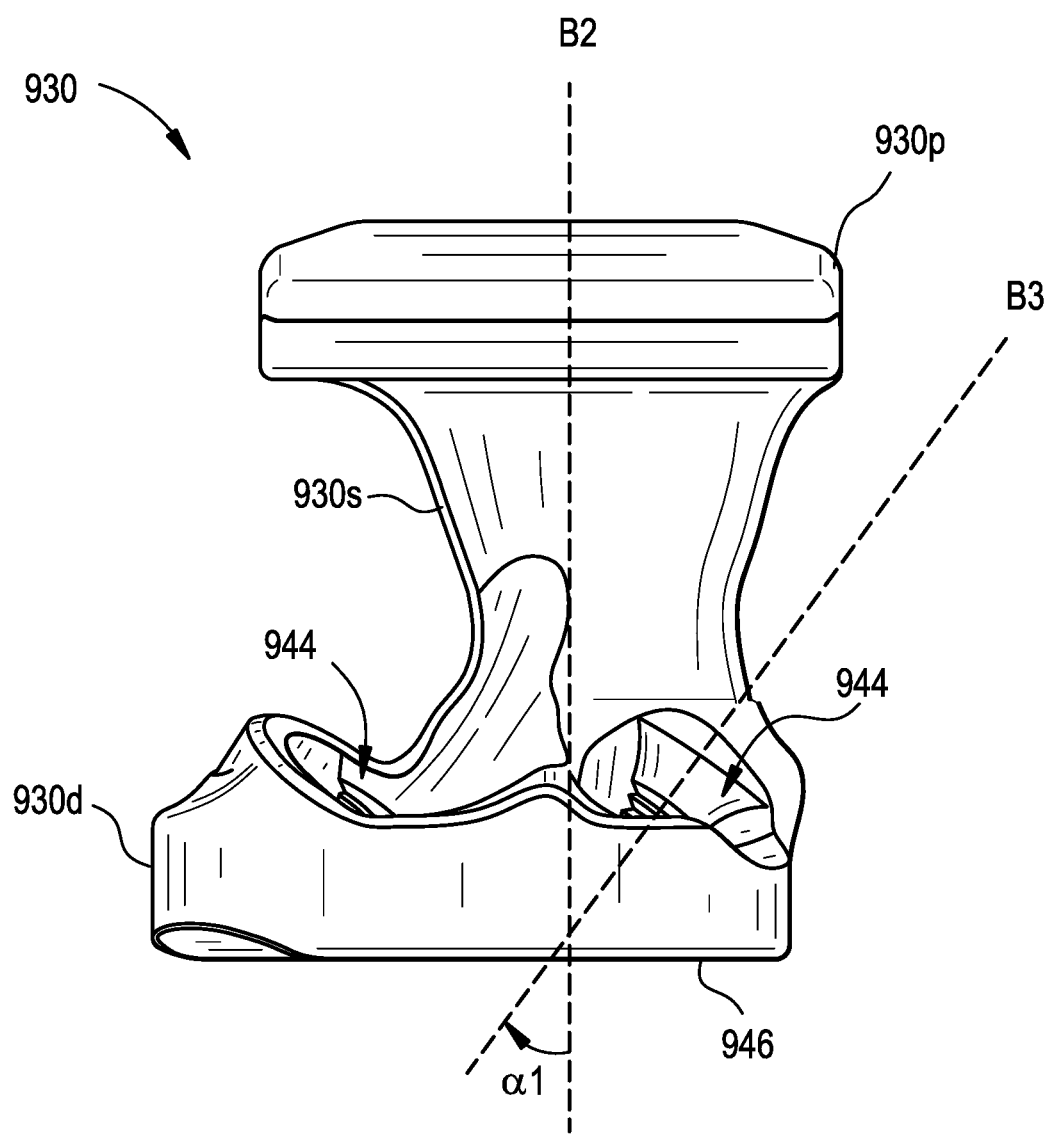
FIG. 13 is a side view of a wing of the bone anchor assembly of FIG. 7.

As will be described in detail below, the wing 930 of this exemplary embodiment can include a plurality of auxiliary bone anchor openings that are biased to the left of the wing, when viewed from the perspective of, for example, FIGS. 8-10. An exemplary embodiment of a wing 930 will now be described with reference to FIGS. 8-17. In the illustrated embodiment, the bracket or wing 930 can include a proximal portion 930p, a distal portion 930d, and a spanning portion 930s that connects the proximal portion to the distal portion of the wing. In one embodiment, the distal portion 930d can extend perpendicular or substantially perpendicular to a proximal-distal axis of the spanning portion 930s. The proximal portion 930p of the wing 930 can extend horizontally from a proximal end of the spanning portion 930s. The wing 930 can be Z-shaped or substantially Z-shaped.

The proximal portion 930p can include a proximal-facing surface 940 and a distal-facing surface 942. The proximal-facing surface 940 can be domed or rounded to provide an atraumatic surface and reduce the risk of tissue irritation post-implantation. The distal-facing surface 942 of the proximal portion 930p can be configured to bear against a proximal terminal end or surface of the receiver member 904. The distal-facing surface 942 can form a negative or a substantial negative of the proximal terminal end or surface of the receiver member 904. For example, the proximal-facing surfaces of the arms of the receiver member 904 can be radially-convex, and the distal-facing surface 942 of the wing 930 can define a radially-concave channel (not shown) that receives the convex ends of the arms.

The proximal portion 930p of the wing can define a central opening 936 that extends through the proximal-facing surface 940 and the distal-facing surface 942. The central opening 936 can be oriented such that a central axis of the opening B1 is perpendicular or substantially perpendicular to the distal-facing surface 942 of the proximal portion 930p. In some embodiments, the central opening 936 can be sized such that the closure mechanism 908 can be inserted through the opening and extend at least partially above the proximal-facing surface 940 of the proximal portion 930p. The central opening 936 can include a smooth, non-threaded interior surface to allow the wing 930 and the closure mechanism 908 to be freely rotatable with respect to one another. The central opening 936 or another feature of the wing 930 can be sized and configured to snap onto or capture a portion of the closure mechanism 908 or a proximal surface of the receiver member 904. In one embodiment, and as described above with reference to FIGS. 4A-4C, a counter bore can be formed about the central opening 936 in the distal-facing surface 942 of the proximal portion 930p to accommodate a radially extending shoulder portion of the closure mechanism 908 that may extend above the proximal terminal end of the receiver member 904. A proximal portion 930*p* of the wing 930 can include any of the features as described herein with reference to wing portions 230, 530, 730, and/or 830.

The spanning portion 930*s* of the wing 930 can extend vertically in a proximal-distal direction to join the proximal portion 930*p* of the wing to the distal portion 930*d* of the wing. The spanning portion 930*s* of the wing 930 can be an elongated arm that extends distally from a side wall of the proximal portion 930*p* in a vertical or a substantially vertical plane. The spanning portion 930*s* can have a lateral surface 950 that engages or faces a sidewall of the receiver member 904. The lateral surface 950 can form a negative of the sidewall of the receiver member 904, such that the spanning portion 930*s* can hug the receiver member with minimal or zero gap there between. For example, the lateral surface 950 can be concave with a radius of curvature equal or substantially equal to a radius of curvature of the exterior sidewall of the receiver member 904.

In some embodiments, the wing 930 can include various features of a unilateral locking interface, including but not limited to one or more grooves and surface projections (not illustrated). As described and illustrated above with respect to a wing 530, for example as shown in FIGS. 3C and 3D, the unilateral locking interface enables a surgical instrument that includes a unilateral locking mechanism to hold onto one side of the wing 930. Exemplary unilateral locking interfaces that can be included in the wing 930 are disclosed in U.S. patent application Ser. No. 15/843,618, filed on Dec. 15, 2017 and entitled "Unilateral Implant Holders and Related Methods," the entire contents of which are hereby incorporated by reference.

The proximal portion 930*p*, distal portion 930*d*, and spanning portion 930*s* can be formed integrally as a monolithic unit as shown. Alternatively, one or more of said components can be separate and selectively attachable to the others. In some embodiments, a kit of modular components can be provided to allow selection of the components most appropriate for a given use. For example, a spanning portion 930*s* of appropriate height can be selected based on the distance between the proximal end of the receiver member 904 and a bone surface in a given application. A length of the spanning portion can vary to accommodate varying lengths of auxiliary bone anchor screws or desired auxiliary bone anchor screw entry points. In some embodiments, the length of the spanning portion can be adjustable, as discussed above. In other embodiments the length of the spanning portion can be fixed.

In one embodiment, the wing 930 can be designed such that an air gap exists between a distal surface 946 of the distal portion 930*d* of the wing 930 and a bone surface of the vertebral level associated with the bone anchor assembly 900. For example, a length of a spanning portion 930*s* can be selected or manufactured such that the distal surface 946 of the distal portion 930*d* is placed within close proximity of the bone surface without contacting the bone surface when the wing is secured onto the receiver of the bone anchor assembly. The length of the spanning portion to achieve this configuration can be dependent upon various circumstantial factors, such as the patient's spinal anatomy, the construction and size of the auxiliary bone anchors, and/or the constraints of a particular surgical application. An air gap between the wing 930 and the bone surface can be advantageous to maintain a tight locking connection between the wing and the receiver member. By preventing the distal portion of the wing from contacting the bone surface, the air gap eliminates an upwards or proximal contact force from the bone which could result in the propping up or loosening of the connection between the wing and the receiver member.

The distal portion 930*d* of the wing 930 can extend outward from a distal end of the spanning portion 930*s* away from the receiver member 904. The degree to which the wing 930 extends outward from the receiver member 904 can vary among different embodiments. In the illustrated embodiment, the ratio of wing extension to rod diameter (or the ratio of wing extension to the width of the rod-receiving recess in the receiver member) is about 2:1. In some embodiments, this ratio can be less than about 10:1, less than about 5:1, less than about 3:1, less than about 2:1, less than about 1:1, and/or less than about 0.5:1. In some embodiments, the ratio can be about 10:1, about 5:1, about 3:1, about 2:1, about 1:1, or about 0.5:1.

Figure 14:
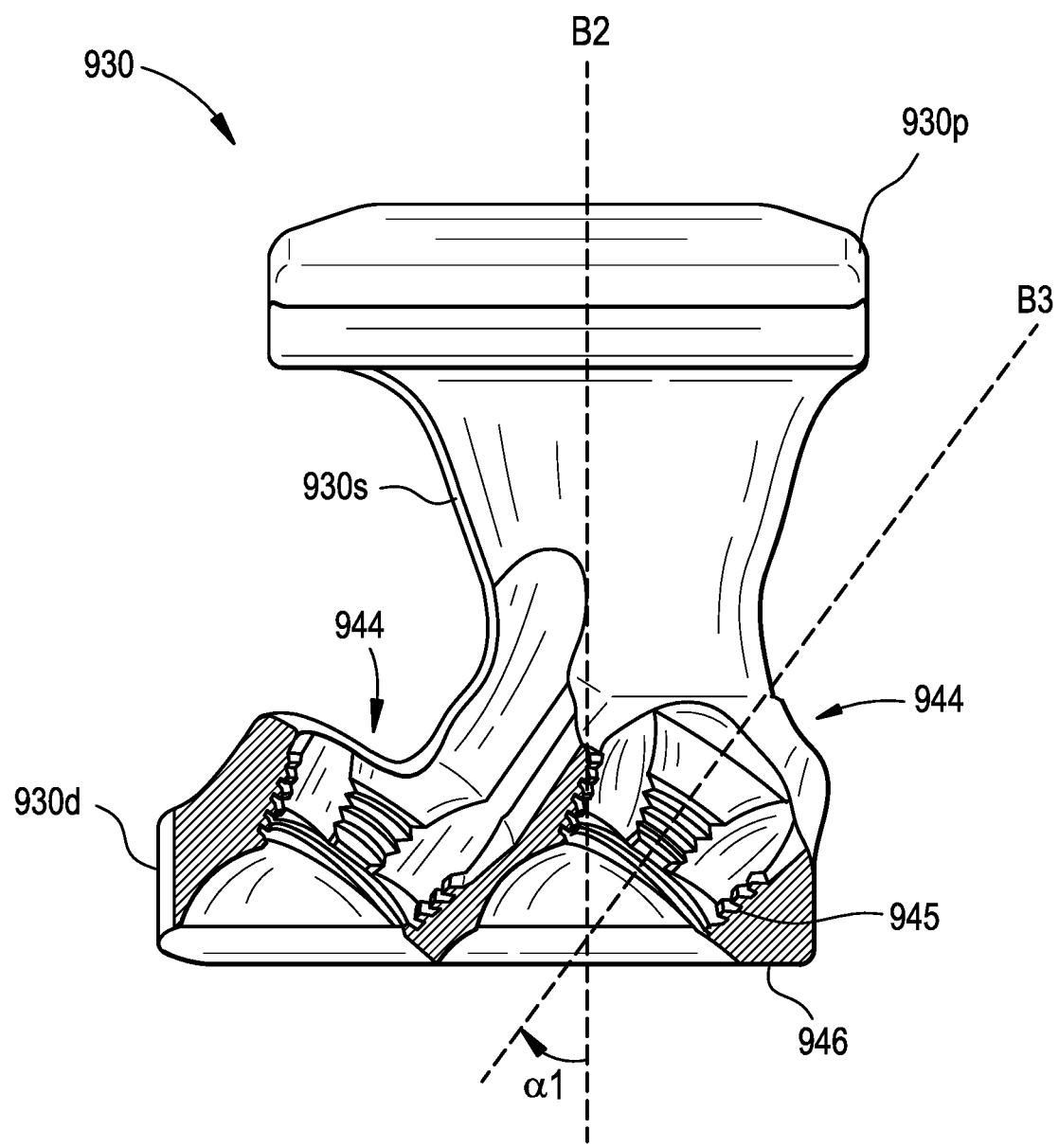
FIG. 14 is a cross-sectional view of the wing of the bone anchor assembly of FIG. 7 taken along the line A-A in FIG. 11.
Figure 15:
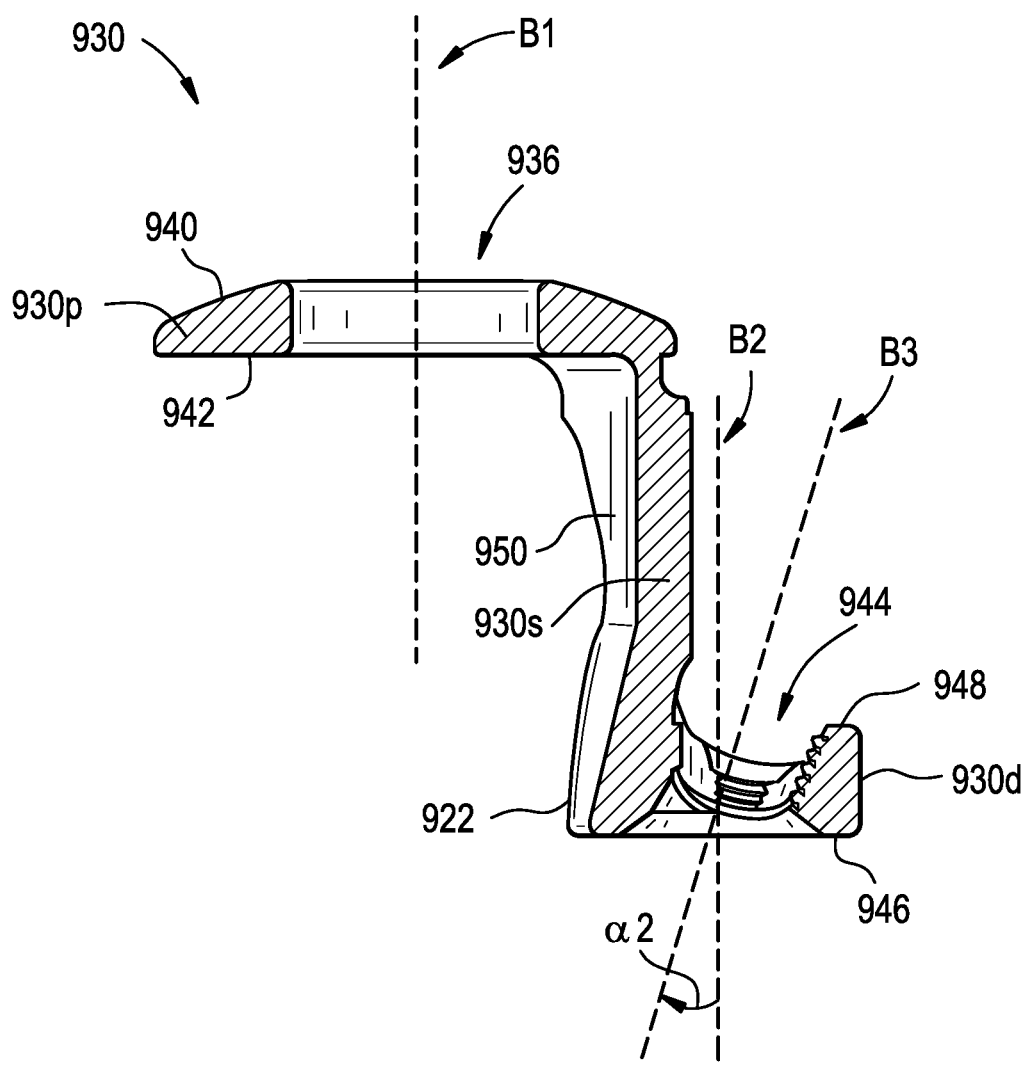
FIG. 15 is a cross-sectional view of a wing of the bone anchor assembly of FIG. 7 taken along the line B-B in FIG. 11.

As can best be seen, for example, in FIGS. 14 and 15, in one embodiment, the distal portion 930*d* can extend outward perpendicular or generally perpendicular to a proximal-distal axis B2 of the spanning portion 930*s*. As shown, the distal portion 930*d* can have a distal surface 946 and a proximal surface 948. The distal surface 946 can be perpendicular or substantially perpendicular to the proximal-distal axis B2 of the spanning portion 930*s*. The distal portion 930*d* of the wing can have a lateral surface 922 that abuts or faces a sidewall of the receiver member 904, such that the distal-portion 930*d* of the wing 930 can hug the receiver member with minimal or zero gap therebetween. For example, the lateral surface 922 can be concave with a radius of curvature equal or substantially equal to a radius of curvature of the exterior sidewall of the receiver member 904.

The distal-facing surface 946 can be configured to contact bone or to be disposed in close proximity to bone. In some embodiments, the distal-facing surface 946 can include teeth, texturing, or other surface features to enhance grip with the adjacent bone. In other embodiments, the wing 930 can be configured such that there is an air gap between the distal-facing surface 946 of the distal portion 930*d* and a proximal-facing surface of a bone into which the primary bone anchor is inserted. As discussed above, such a configuration can maintain the integrity of the connection between the wing 930 and the receiver 904.

The distal portion 930*d* of the wing 930 can define a plurality of auxiliary bone anchor openings 944 that each extend through the proximal-facing surface 948 and the distal-facing surface 946 of the distal portion. Each of the plurality of auxiliary bone anchor openings 944 can be configured to receive an auxiliary bone anchor 934. As can be seen, for example, in FIGS. 8-10, each auxiliary bone anchor opening 944 can be sized to insert a distal shaft of the auxiliary bone anchor 934 through the opening and to abut the proximal head of the auxiliary bone anchor when disposed therein. Each bone anchor opening 944 can extend at an oblique angle relative to the proximal-distal axis B2 of the spanning portion 930*s*. With reference to FIG. 14, a central axis B3 of an auxiliary bone anchor opening 944 can be obliquely angled relative to the proximal-distal axis B2 of the wing, where the proximal-distal axis B3 runs perpendicular or substantially perpendicular to the distal surface 946 of the wing 930. For example, as shown, the bone anchor openings 944 can be angled to extend to the left of the vertically-disposed spanning portion 930*s*. In such embodiments, the central axis B3 of the bone anchor opening 944 can extend at an oblique angle $\alpha 1$, down and to the left, with respect to the proximal-distal axis B2 of the spanning portion 930*s*.

In some embodiments, depending on the requirements of the particular application, the auxiliary bone anchor openings can extend at an oblique angle to the left of the proximal-distal axis B2 of the spanning portion 930s. For example, with reference to FIG. 14, the central axis B3 of an auxiliary bone anchor opening 944 can extend at an oblique angle α1, down and to the left, with respect to the proximal-distal axis B2 of the spanning portion 930s of the wing 930. This arrangement can facilitate various bone anchor placements in which a distal end of an auxiliary bone anchor extends towards the left of the wing 930 when viewed from the perspective of FIGS. 8-10.

For example, the central axis B3 of each opening 944 can extend at an angle α1 of about 35 degrees to the left of the axis B2. In some embodiments, the central axis B3 of each opening 944 can extend at an angle α1 of between about 0 degrees and about 60 degrees from the proximal-distal axis B2 of the spanning portion. Biasing the central axis B3 of an auxiliary bone anchor opening by an angle α1 can establish an insertion trajectory of an auxiliary bone anchor into bone that is angled along a cephalad-caudal axis of a patient. For example, the angle α1 can be selected such that, in instances in which an auxiliary bone anchor is inserted in a caudal direction, the auxiliary bone anchor can be driven closer to a center of a vertebra or a facet to avoid placement too close to an edge of the vertebra or the facet and, in instances in which the auxiliary bone anchor is inserted in a cephalad direction, the auxiliary bone anchor can be kept within a thin lateral mass of the vertebra or the facet. In some embodiments, the angle α1 can be between about 46 degrees and about 60 degrees from the proximal-distal axis B2 of the spanning portion. In some embodiments, angling the openings 944 to this degree can enable the above-described functionality (i.e., keeping a caudally-directed anchor away from an edge of a vertebra or facet or keeping a cephalically-directed anchor within a thin lateral mass of the vertebra or facet). This arrangement can facilitate various bone anchor placements in which the distal end of the auxiliary bone anchor extends to the left of the wing 930 when viewed from the perspective of FIG. 14.

For example, as shown in FIG. 7, such bone anchor placements can include ones in which the wing 930 is disposed laterally to a spinal rod 906 and in which the auxiliary bone anchor 934 is driven through the bone anchor opening 944 with a cephalad trajectory (i.e., towards a patient's head). This orientation can allow the auxiliary bone anchor 934 to remain wholly within the same vertebral level 901 as the primary bone anchor 902 associated with the bone anchor assembly 900, for example within a lateral mass of the vertebra. It will be appreciated that the wing 930 can be flipped around to be positioned on the other side of the illustrated rod 906 (e.g., on a medial side of the rod), or to be positioned laterally to a contralateral spinal rod (not shown). In these cases, the positioning of the wing 930 can facilitate bone anchor placements in which an auxiliary bone anchor 934 can be driven through the bone anchor opening 944 with a caudal trajectory (i.e., towards a patient's feet). In some embodiments, as discussed further below with respect to FIG. 18, a caudal trajectory can allow for fixation of an auxiliary bone screw 934 into multiple cortical bone layers, e.g., at least two, at least three, or more. The angled auxiliary bone anchor opening 944 can allow for the above described bone anchor placements while accommodating a particular spinal anatomy or surgical application.

In some embodiments, each of the bone anchor openings 944 can include any of a number of features for accepting bone anchors 934 at varying angles. For example, as discussed above with respect to FIG. 2A-2M, each of the bone anchor openings 944 can be at least partially threaded to receive a variable-angle locking screw having a threaded proximal head. As shown, the opening 944 can have a plurality of columns of threads 945 spaced apart to define a plurality of non-threaded recesses 947. In this manner, the threads of the opening 944 can form an interlocking interface and mate with threads of an auxiliary bone anchor to lock the auxiliary bone anchor therein. For example, FIGS. 8-10 illustrate an embodiment of a wing 930 with two auxiliary bone anchors 934 engaged within the auxiliary bone anchor receiving recesses 944. In one embodiment, the threads of the opening 944 can be conical threads. The columns of threads can be arranged around the inner surface of the opening 944 for engaging threads on the head of a locking auxiliary bone anchor and/or a variable-angle locking auxiliary bone anchor. An auxiliary bone anchor 934 can thus be locked with the wing 930 coaxially with the central axis B3 of the opening 944 or at a selected angle within a range of selectable angles relative to the central axis B3 of the opening 944. While the illustrated embodiment has four columns of threads within an auxiliary bone anchor opening, it will be appreciated that the auxiliary bone anchor opening can have any number of columns of threads (e.g., two, three, four, five, etc.) to facilitate variable angle locking with an auxiliary bone anchor.

The auxiliary bone anchor 934 can include features to facilitate this variable-angle locking, such as a proximal head that is at least partially spherical having a thread with a profile that follows the arc-shaped radius of curvature of the spherical portion of the head. The variable-angle capability of the interlocking interface (i.e., the screw/opening interface) can allow the user to place a locking auxiliary bone anchor into the bone at any angle defined within angulation limits. A locking interface between an auxiliary bone anchor opening and an auxiliary bone anchor received therein can increase stability and prevent the auxiliary bone anchor from backing out of the opening. Moreover, the interlocking interface can be biased to create angulated trajectories of insertion for an auxiliary bone anchor screw. In other embodiments, the interior surface of the opening 944 can be smooth or spherical, without threads or locking features.

In some embodiments, the proximal-most extent of each auxiliary bone anchor 934 can be distal to the spinal rod 906. In other embodiments, the proximal-most extent of each auxiliary bone anchor 934 can be distal to the distal-most extent of the receiver member 904. These configurations can advantageously reduce the overall profile of the assembly 900. While two bone anchor openings 944 are shown in the illustrated embodiments, it will be appreciated that the wing 930 can include any number of auxiliary bone anchor openings.

In some embodiments, the central axis B3 of each of the plurality of auxiliary bone anchor openings can, additionally or alternatively, be biased along a medial-lateral axis. As can best be seen in FIG. 15, the central axis B3 of the auxiliary bone anchor opening 944 can extend at an angle α2 inward or outward from the proximal-distal axis B2 of the wing. The angle α2 can extend medially, or inward, towards the central axis B1 of the wing. Biasing the trajectory of the central axis B3 of the auxiliary bone anchor opening inward or medially by an angle α2 can account for a lateral extension of the distal portion 930d of the wing and direct an auxiliary bone anchor 934 into the bone towards a center-line of the patient's spine. In some embodiments, α2 can be between about 0 degrees and about 30 degrees. In some embodiments, α2 can be between about 0 degrees and about 25 degrees. In still other embodiments, α2 can be between about 5 degrees and about 10 degrees.

Figure 16:
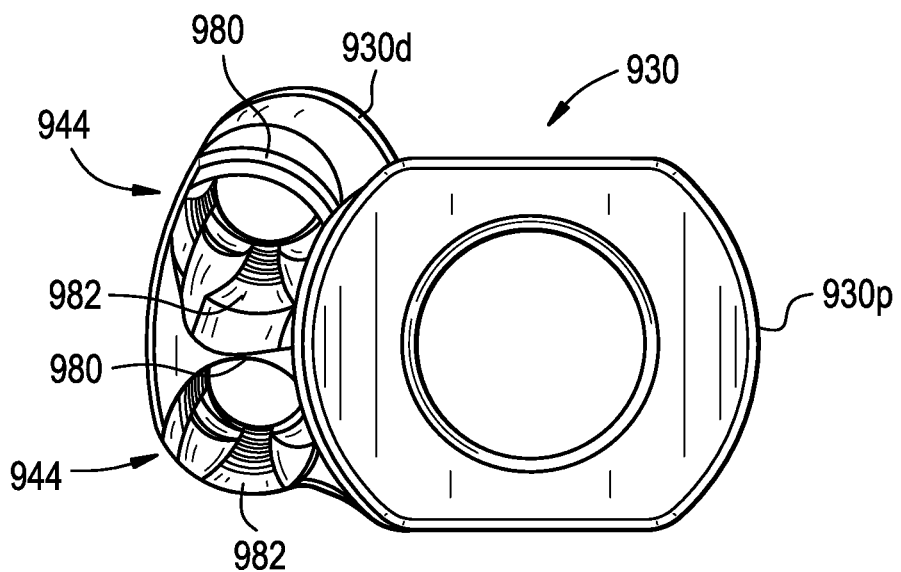
FIG. 16 is a top view of a wing of the bone anchor assembly of FIG. 7 with the auxiliary bone anchor openings extending in a cephalad direction.

FIG. 16 is a top view of the wing 930 of the bone anchor assembly of FIGS. 8-14, i.e., a wing that includes a plurality of auxiliary bone anchor openings 944 extending down and to the left of the wing, with a central axis B3 of the auxiliary bone anchor openings 944 extending to the left of the wing. As shown in FIG. 16, from a posterior viewpoint, the wing 930 can be positioned with the distal portion 930d extending outward from a left side of the bone anchor assembly (i.e., extending laterally from a bone anchor assembly placed to the left of the spinal midline or extending medially from a bone anchor assembly placed to the right of the spinal midline). With such an orientation, the central axis B3 of the auxiliary bone anchor opening can extend in a cephalad direction (or towards a patient's head). In this exemplary cephalad configuration, each angled auxiliary bone anchor opening 944 has a superior surface 980 and an inferior surface 982. With the auxiliary bone anchor openings extending in a cephalad direction, the superior surface 980 is more proximal (or higher) than the inferior surface 982, such that an opening of the auxiliary bone anchor opening 944 faces in the caudal direction, while the central axis B3 of the auxiliary bone anchor opening extends with a cephalad insertion trajectory such that an auxiliary bone anchor received therein extends towards the head of a patient. The distal portion 930 can extend substantially perpendicular to the wing, such that the distal facing surface 946 is perpendicular or substantially perpendicular with respect to the proximal-distal axis B2 of the wing 930. In some embodiments, when the bone anchor opening is also angled medially (e.g., as discussed above in FIG. 15), a surface of the bone anchor opening 944 that is closest to the spanning portion 930s can be more proximal (or higher) than an opposing surface, i.e., a surface that is further away from the spanning portion, of the bone anchor opening. In some embodiments, where the auxiliary bone anchor opening is also angled laterally, the surface of the bone anchor opening 944 that is closest to the spanning portion 930s can be more distal (or lower) than an opposing surface of the bone anchor opening.

Figure 17:
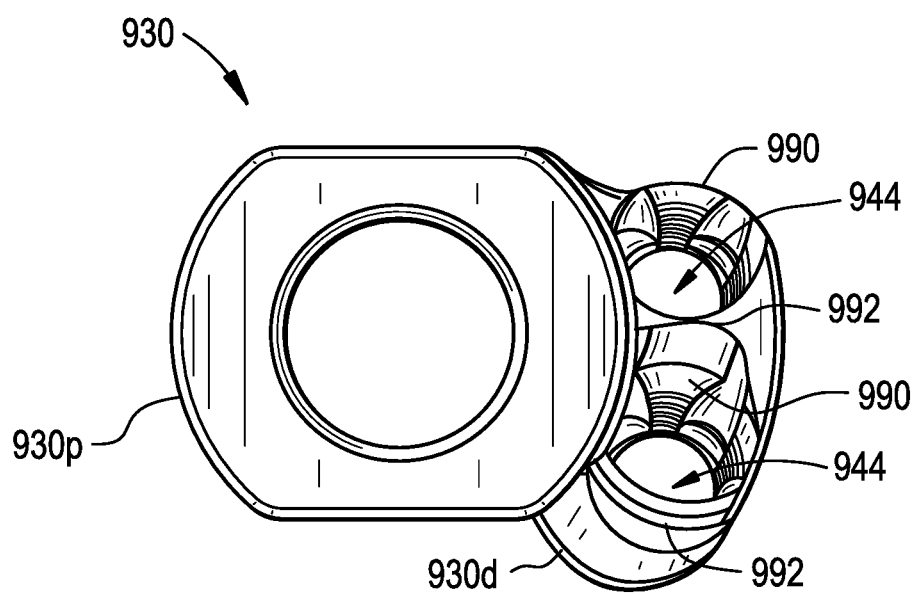
FIG. 17 is a top view of a wing of the bone anchor assembly of FIG. 7 with the auxiliary bone anchor openings extending in a caudal direction.

FIG. 17 is a top view of the wing 930 of the bone anchor assembly of FIGS. 8-14, i.e., a wing that includes a plurality of auxiliary bone anchor openings extending down and to the left of the spanning portion of the wing, with a central axis B3 of each of the auxiliary bone anchor openings 944 extending in a caudal direction. As shown in FIG. 17, from a posterior viewpoint, the wing 930 can be positioned with the distal portion 930d extending outward from a right side of the bone anchor assembly (i.e., extending medially from a bone anchor assembly placed to the left of the spinal midline or extending laterally from a bone anchor assembly placed to the right of the spinal midline) and thus facing in a caudal direction. In this exemplary caudal configuration, each angled auxiliary bone anchor opening 944 has a superior end 990 and an inferior end 992. With the auxiliary bone anchor openings extending in a caudal direction, the superior end 990 is more distal (or lower) than the inferior end 982, such that an opening of the auxiliary bone anchor opening 944 faces in the cephalad direction, while the central axis B3 of the auxiliary bone anchor opening extends with a caudal insertion trajectory such that an auxiliary bone anchor received therein extends towards the feet of a patient. The distal portion 930 can extend substantially perpendicular to the wing, such that the distal facing surface 946 is perpendicular or substantially perpendicular with respect to the proximal-distal axis B2 of the wing 930. In some embodiments, when the bone anchor opening is angled medially (e.g., as discussed above in FIG. 15), a surface of the bone anchor opening 944 that is closest to the spanning portion 930s can be more proximal (or higher) than an opposing surface, i.e., a surface that is further away from the spanning portion, of the bone anchor opening. In some embodiments, when the bone anchor opening is angled laterally, the surface of the bone anchor opening 944 that is closest to the spanning portion 930s can be more distal (or lower) than an opposing surface of the bone anchor opening.

Some embodiments of the bone anchor assembly can include a wing having a distal portion defining a plurality of auxiliary bone anchor openings, where each of the plurality of bone anchor openings are angled to the right of a vertically-disposed spanning portion of the wing. In such embodiments, an auxiliary bone anchor can be disposed through the opening with caudal or cephalad trajectories, similar to those facilitated by the wing 930 of the bone anchor assembly 900 when implanted on the opposite side of the patient's spine (i.e., the left-hand side of the patient).

Figure 18:
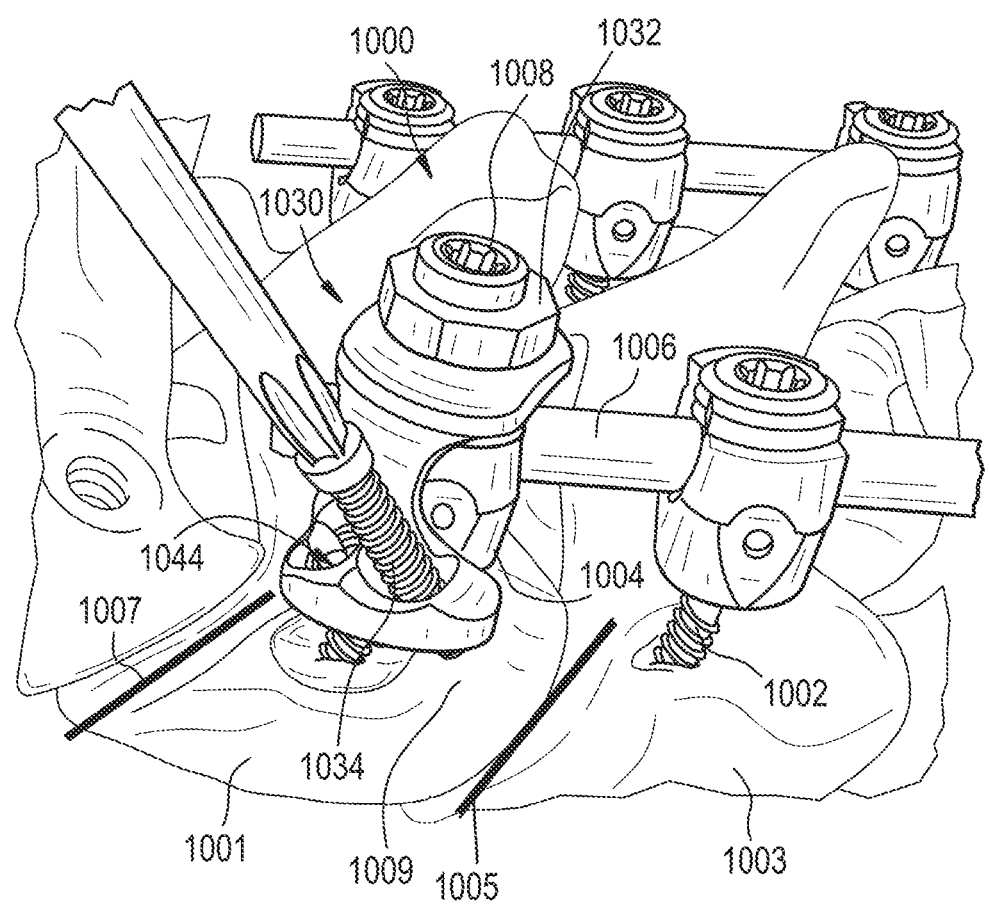
FIG. 18 is a perspective view of a bone anchor assembly and a spinal rod attached to a spine.
Figure 19:
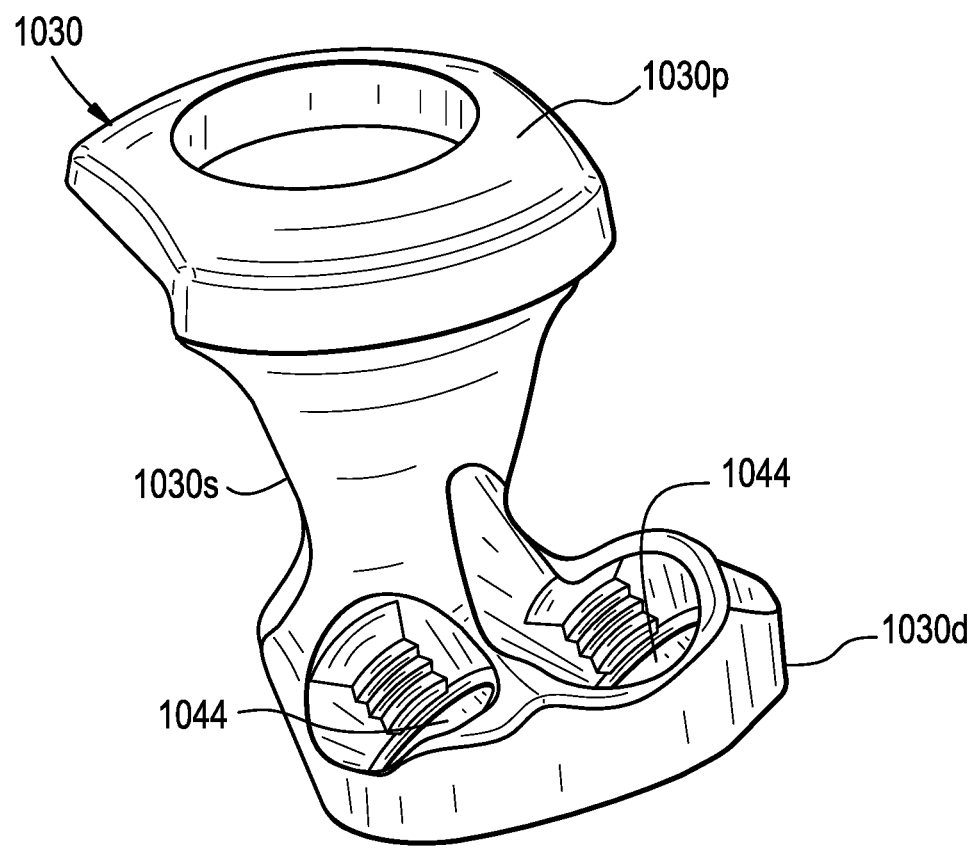
FIG. 19 is a perspective view of a wing of the bone anchor assembly of FIG. 18.
Figure 20:
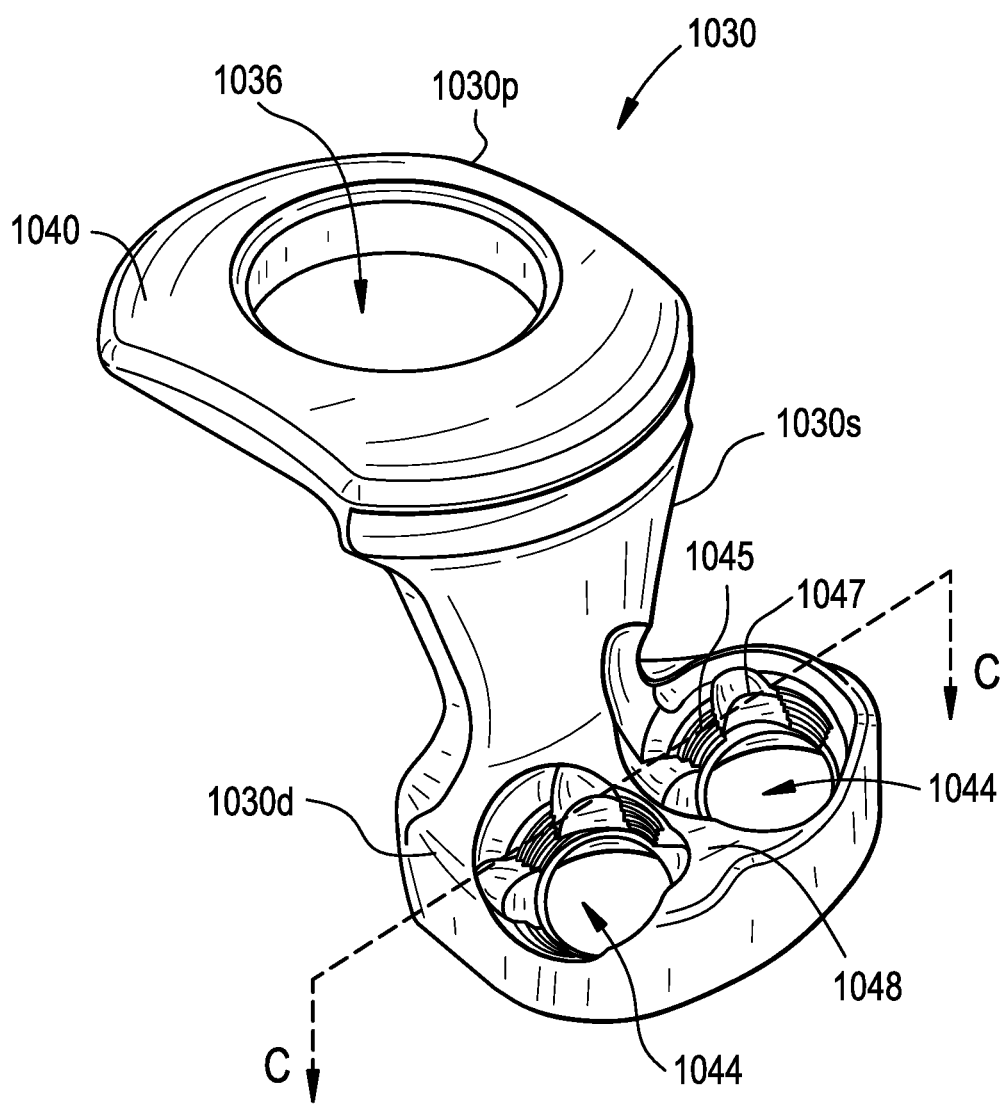
FIG. 20 is a perspective view of a wing of the bone anchor assembly of FIG. 18.

FIGS. 18-23 illustrate an exemplary embodiment of a bone anchor assembly 1000 that includes a bracket or wing 1030 having a distal portion 1030d that defines a plurality of auxiliary bone anchor openings 1044 that can extend at a biased or angled trajectory towards the right of a vertically-disposed spanning portion 1030s of the wing 1030. As shown, the bone anchor assembly 1000 can be implanted into a vertebral level 1001. The bone anchor assembly 1000 can include a bone anchor (labeled 1002 and visible in a vertebra 1003 that is adjacent to the vertebra 1001 associated with the bone anchor assembly 1000), a receiver member 1004, a closure mechanism 1008, a bracket or wing 1030, a nut 1032, and one or more auxiliary bone anchors 1034, which can be seen, for example, in FIG. 18 being inserted into an auxiliary bone anchor opening 1044 and crossing a first layer of cortical bone 1009 of the vertebra 1001. Also shown in FIG. 18 is a first facet plane 1005 and a second facet plane 1007 of the vertebra. As described herein, in some embodiments the auxiliary bone anchor 1034 can be driven across a facet plane (e.g., facet plane 1005) such that the bone anchor extends through multiple vertebrae and/or cortical bone layers of one or more vertebrae. Except as described below or as will be readily appreciated by one having ordinary skill in the art, the bone anchor 1002, the receiver member 1004, the closure mechanism 1008, the nut 1032, and the auxiliary bone anchor 1034 are substantially similar to the bone anchor 202, the receiver member 204, the closure mechanism 208, the nut 232, and the auxiliary bone anchors 234 described above with respect to FIGS. 2A-2M. A detailed description of the structure and function thereof is thus omitted here for the sake of brevity. The bone anchor assembly 1000 can include any one or more of the features of one or more of the bone anchor assemblies described above.

As shown in FIGS. 18-23, the bracket or wing 1030 can include a proximal portion 1030p, a distal portion 1030d, and a spanning portion 1030s that connects the proximal portion to the distal portion of the wing. Except as described below or as will be readily appreciated by one having ordinary skill in the art, the proximal portion 1030p and the spanning portion 1030s of the wing 1030 are substantially similar to the proximal portion 930p and the spanning portion 930s of the wing 930 described above with respect to FIGS. 7-17. A detailed description of the structure and function thereof is thus omitted here for the sake of brevity.

The wing 1030 can include any one or more of the features of the wing 930 described above.

Figure 21:
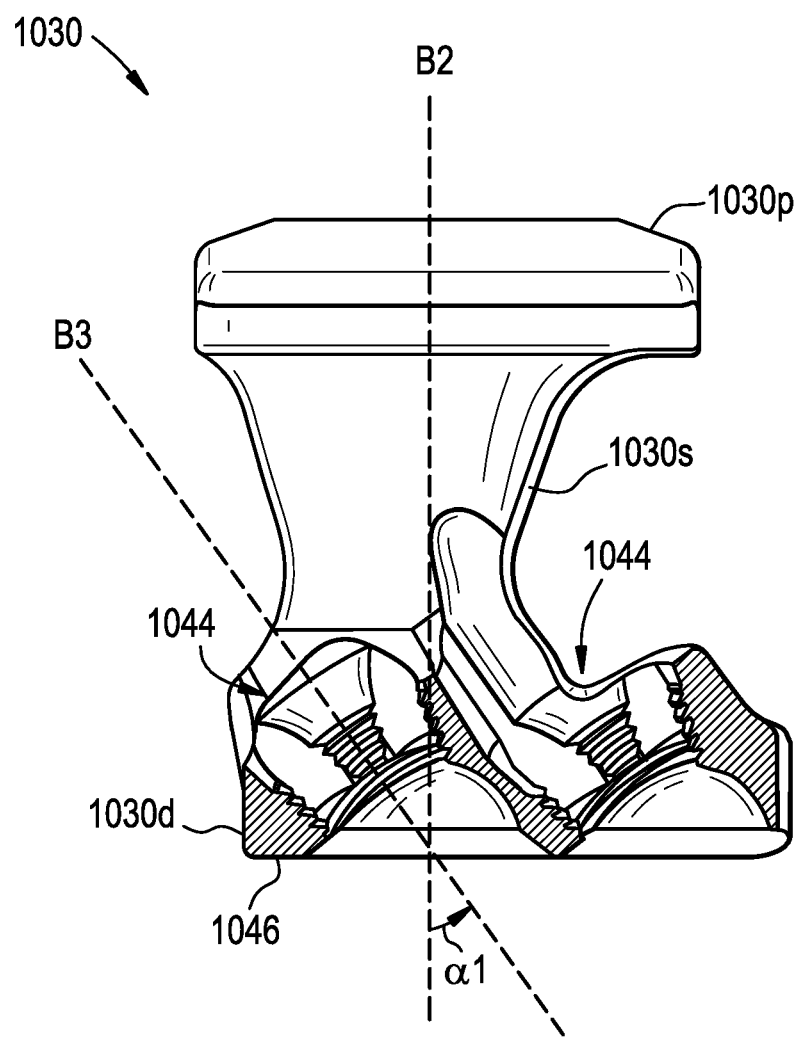
FIG. 21 is a cross-sectional view of a wing of the bone anchor assembly of FIG. 18 taken along the line C-C in FIG. 20.

In the illustrated embodiment, the distal portion 1030*d* of the wing 1030 and the auxiliary bone anchor openings 1044 are substantially similar to the distal portion 930*d* and the auxiliary bone anchor openings 944 of the wing 930, except that each of the auxiliary bone anchor openings 1044 is angled, or extends towards, the right of the vertically-disposed spanning portion 1030*s* (when viewed from the perspective of, for example, FIG. 21). As shown, the distal portion 1030*d* can extend outward from a distal end of the spanning portion 1030*s* perpendicular or generally perpendicular to the proximal-distal axis B2 of the spanning portion. The distal portion 1030*d* can have a distal-facing surface 1046 and a proximal-facing surface 1048. The distal surface 1046 can be perpendicular or substantially perpendicular to the proximal-distal axis B2 of the spanning portion 1030*s*. The distal portion 1030*d* can define a plurality of auxiliary bone anchor openings 1044 that each extend through the proximal-facing surface 1048 and the distal-facing surface 1046 and are each configured to receive an auxiliary bone anchor 1034. As shown in the illustrated embodiment, the bone anchor opening 1044 can be angled or biased to the right of the vertically extending axis B2 of the spanning portion 1030*s*, while the distal surface 1046 and the distal portion 1030*d* remain perpendicular or generally perpendicular to the axis B2. In such embodiments, the central axis B3 of the bone anchor opening 1044 can extend at an oblique angle α1, down and to the right, with respect to the proximal-distal axis B2 of the spanning portion 1030*s* of the wing. This arrangement can facilitate various bone anchor placements in which the distal end of the auxiliary bone anchor extends towards the right of the wing 1030 when viewed from the perspective of FIG. 21. While two bone anchor openings 1044 are shown in the illustrated embodiments, it will be appreciated that the wing 1030 can include any number of bone anchor openings (e.g., one, two, three, four, five, and so on). In some embodiments, multiple auxiliary bone anchor openings can be preferred to provide multiple additional fixation points to increase the pullout strength of a bone anchor.

For example, as shown in FIG. 18, such bone anchor placements can include ones in which the wing 1030 is disposed laterally to a spinal rod 1006 and in which an auxiliary bone anchor 1034 is driven through a bone anchor opening 1044 with a caudal trajectory (i.e., towards a patient's feet). This orientation can allow the auxiliary bone anchor 1034 to extend into one or more adjacent vertebral levels, e.g., across a facet joint or facet plane of one or more adjacent vertebral levels. A caudal trajectory can allow for fixation of at least one auxiliary bone anchor screw 1034 into multiple cortical bone layers, e.g., at least two, at least three, or more. For example, with continued reference to FIG. 18, with the primary bone anchor (not visible) of the bone anchor assembly 1000 positioned in a superior vertebral level 1001, the bone anchor assembly can effect tri-cortical fixation with the auxiliary bone anchor 1034 crossing a facet joint between the superior vertebral level and an adjacent inferior vertebral level 1003. It will be appreciated that the wing 1030 can be flipped around to be positioned on the other side of the illustrated rod 1006 (e.g., on a medial side of the rod), or to be positioned laterally to a contralateral spinal rod (not shown). In these cases, the positioning of the wing 1030 can facilitate bone anchor placements in which the auxiliary bone anchor 1034 can be driven through the bone anchor opening 1044 with a cephalad trajectory (i.e., towards a patient's head). As discussed above with respect to FIG. 7, a cephalad trajectory can allow at least one auxiliary bone anchor 1034 to remain wholly within the same vertebral level as the primary bone anchor 1002 of the bone anchor assembly 1000, for example within a lateral mass of the vertebra. The angled auxiliary bone anchor opening 1044 can allow for the above-described bone anchor placements while accommodating for a particular spinal anatomy or surgical procedure.

Turning back to FIG. 21, in some embodiments, depending on the requirements of the particular application, the central axis B3 of the auxiliary bone anchor opening 1044 can be obliquely angled at any angle α1 to the right of the axis B2 of the spanning portion 1030*s*. The axis B2 can be perpendicular or substantially perpendicular to the distal-facing surface 1046 of the distal portion 1030*d* of the wing. For example, as shown in FIG. 21, the bone anchor opening 1044 can be obliquely angled, such that the central axis B3 of the bone anchor opening 1044 extends at an angle α1 of 35 degrees to the right of the proximal-distal axis B2 of the spanning portion 1030*s*. In some embodiments, the bone anchor opening 1044 can be obliquely angled such that the central axis B3 of the bone anchor opening 1044 can extend at an angle α1 between about 0 degrees and about 60 degrees to the right of the proximal-distal axis B2 of the spanning portion 1030*s*. For example, the angle α1 can be selected such that, in instances in which an auxiliary bone anchor is inserted in a caudal direction, the auxiliary bone anchor can be driven closer to a center of a vertebra or a facet to avoid placement too close to an edge of the vertebra or the facet and, in instances in which the auxiliary bone anchor is inserted in a cephalad direction, the auxiliary bone anchor can be kept within a thin lateral mass of the vertebra or the facet. In some embodiments, the angle α1 can be between about 46 degrees and about 60 degrees from the proximal-distal axis B2 of the spanning portion. In some embodiments, angling the openings 1044 to this degree can enable the above-described functionality (i.e., keeping a caudally-directed anchor away from an edge of a vertebra or facet or keeping a cephalically-directed anchor within a thin lateral mass of the vertebra or facet). As discussed above, an auxiliary bone anchor 1044 can include one or more columns of threads 1045 to establish an interlocking interface with an auxiliary bone anchor received therein. In some embodiments, the interlocking interface can be a variable angle interlocking interface. Thus, an auxiliary bone anchor 1034 can be readily disposed in the bone anchor opening 1044 with the distal shaft of the anchor having an angular trajectory coaxial with, or within a defined cone of angulation with respect to, the central axis B3 of the bone anchor opening 1044.

As discussed above with respect to FIG. 15, in some embodiments, the bone anchor opening 1044 can be further angled to face inward or outward (i.e., medially or laterally) with respect to the vertically-disposed spanning portion 1030*s*. Accordingly, in some embodiments, based on the requirements of the particular application, the bone anchor opening 1044 can be obliquely angled inward or outward to fix the central axis B3 of the bone anchor opening 1044 at any medial or lateral angle α2 between about 0 and about 30 degrees with respect to the proximal-distal axis B2 of the spanning portion 1030*s*. In some embodiments, the bone anchor opening 1044 can be angled such that the central axis B3 extends at an angle α2 of about 5 to about 10 degrees inclusive. Thus, by angling the bone anchor opening 1044 inward or outward, the distal portion 1030*d* can facilitate placement of the auxiliary bone anchor 1034 having a medial or lateral trajectory component in addition to or instead of a cephalad or caudal trajectory component thought the bone anchor opening 1044. In some embodiments, angling the bone anchor opening 1044 inward or outward can facilitate bone anchor placements in which the auxiliary bone anchor 1034 is secured within the lateral mass of a vertebra. In some embodiments, angling the bone anchor opening 1044 inward or outward can provide clearance for a driver instrument to access the bone anchor opening 1044.

Figure 22:
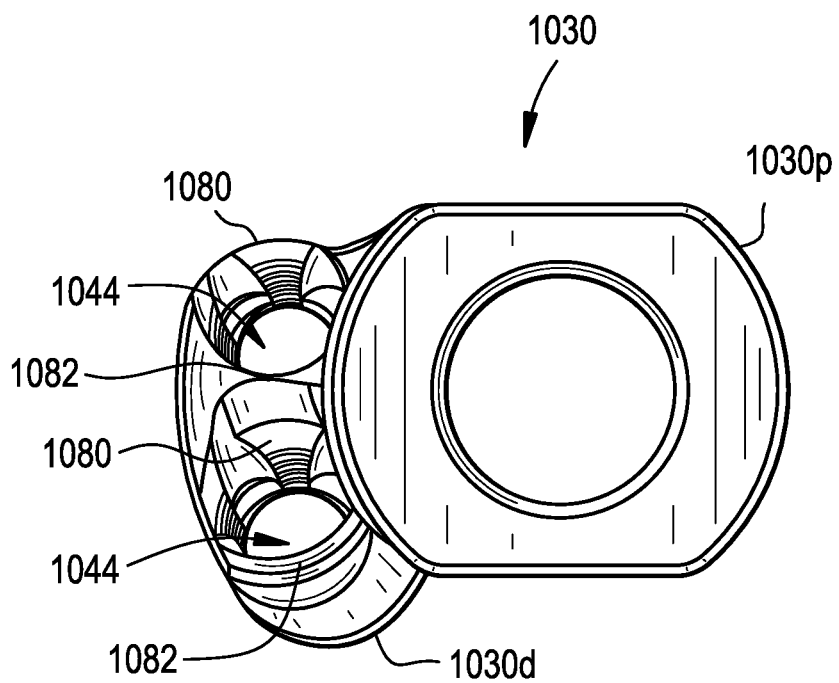
FIG. 22 is a top view of a wing of the bone anchor assembly of FIG. 18 with the auxiliary bone anchor openings extending in a caudal direction.

FIG. 22 is a top view of the wing 1030 of the bone anchor assembly of FIG. 18, i.e., a wing that includes a plurality of auxiliary bone anchor openings 1044 extending down and to the right of the wing, with a central axis B3 of the auxiliary bone anchor openings 944 extending to the right of the wing. As shown in FIG. 22, from a posterior viewpoint, the wing 1030 can be positioned with the distal portion 1030*d* extending outward from a left side of the bone anchor assembly (i.e., extending laterally from a bone anchor assembly placed to the left of the spinal midline or extending medially from a bone anchor assembly placed to the right of the spinal midline). With such an orientation, the central axis B3 of the auxiliary bone anchor opening can extend in a caudal direction (or towards a patient's feet). In this exemplary caudal configuration, each angled auxiliary bone anchor opening has a superior end 1080 and an inferior end 1082. With the auxiliary bone anchor openings extending in a caudal direction, the superior end 1080 is more distal (or lower) than the inferior end 1082, such that an opening of the auxiliary bone anchor opening 1044 faces in the cephalad direction, while the central axis B3 of the auxiliary bone anchor opening extends with a caudal insertion trajectory such that an auxiliary bone anchor received therein extends towards the feet of a patient. The distal portion 1030 can extend substantially perpendicular to the wing, such that the distal facing surface 1046 is perpendicular or substantially perpendicular with respect to the proximal-distal axis B2 of the wing 1030. In some embodiments, when the bone anchor opening is also angled medially (e.g., as discussed above with reference FIG. 15), a surface of the bone anchor opening 1044 that is closest to the spanning portion 1030*s* can be more proximal (or higher) than an opposing surface of the bone anchor opening, i.e., a surface that is further away from the spanning portion. In some embodiments, when the auxiliary bone anchor opening is angled laterally, the surface of the bone anchor opening 1044 that is closest to the spanning portion 1030*s* can be more distal (or lower) than an opposing surface of the bone anchor opening.

Figure 23:
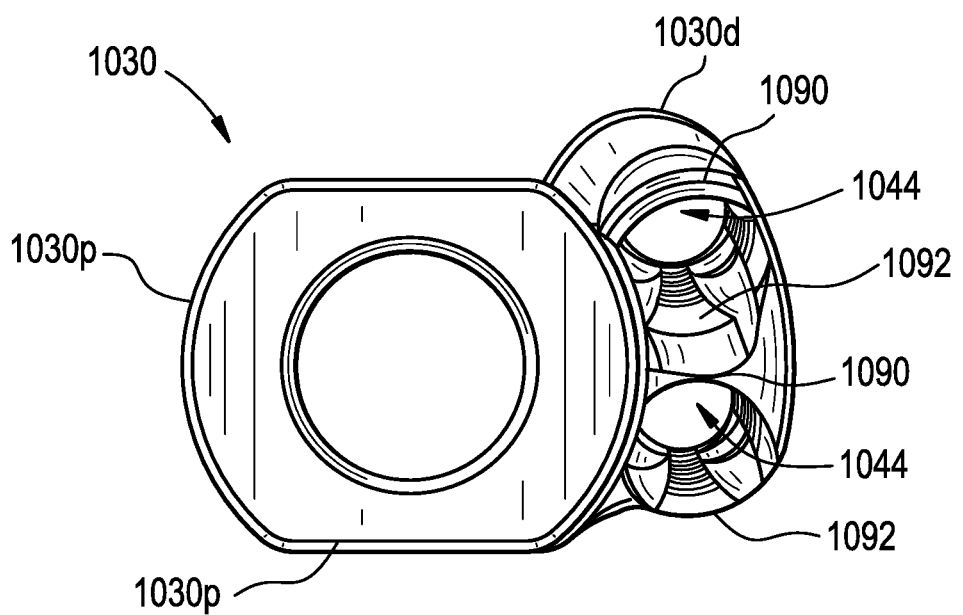
FIG. 23 is a top view of a wing of the bone anchor assembly of FIG. 18 with the auxiliary bone anchor openings extending in a cephalad direction.

FIG. 23 is a top view of the wing 1030 of the bone anchor assembly of FIG. 18, i.e., a wing that includes a plurality of auxiliary bone anchor openings 1044 extending down and to the right of the wing, with a central axis B3 of the auxiliary bone anchor openings 944 extending to the right of the wing. As shown in FIG. 23, from a posterior viewpoint, the wing 1030 can be positioned with the distal portion 1030*d* extending outward from a right side of the bone anchor assembly (i.e., extending medially from a bone anchor assembly placed to the left of the spinal midline or extending laterally from a bone anchor assembly placed to the right of the spinal midline). With the distal portion 1030*d* extending laterally relative to the right of the spinal midline, the central axis B3 of the auxiliary bone anchor opening can extend in a cephalad direction (or towards a patient's head). In this exemplary cephalad configuration, each angled auxiliary bone anchor opening 1044 has a superior end 1090 and an inferior end 1092, where the superior end 1090 is more proximal (or higher) than the inferior end 1092, such that an opening of the auxiliary bone anchor opening 1044 faces in the caudal direction, while the central axis B3 of the auxiliary bone anchor opening extends with a cephalad insertion trajectory such that an auxiliary bone anchor received therein extends towards the head of a patient. The distal portion 1030 can extend substantially perpendicular to the spanning portion, such that the distal facing surface 1046 is perpendicular or substantially perpendicular with respect to the proximal-distal axis B2 of the wing 1030. In some embodiments, when the bone anchor opening is also angled medially (e.g., as discussed with reference to FIG. 15), a surface of the bone anchor opening 1044 that is closest to the spanning portion 1030*s* can be more proximal (or higher) than an opposing surface, i.e., a surface that is further away from the spanning portion, of the bone anchor opening. In some embodiments, when the bone anchor opening is angled laterally, the surface of the bone anchor opening 1044 that is closest to the spanning portion 1030*s* can be more distal (or lower) than an opposing surface of the bone anchor opening.

Figure 24:
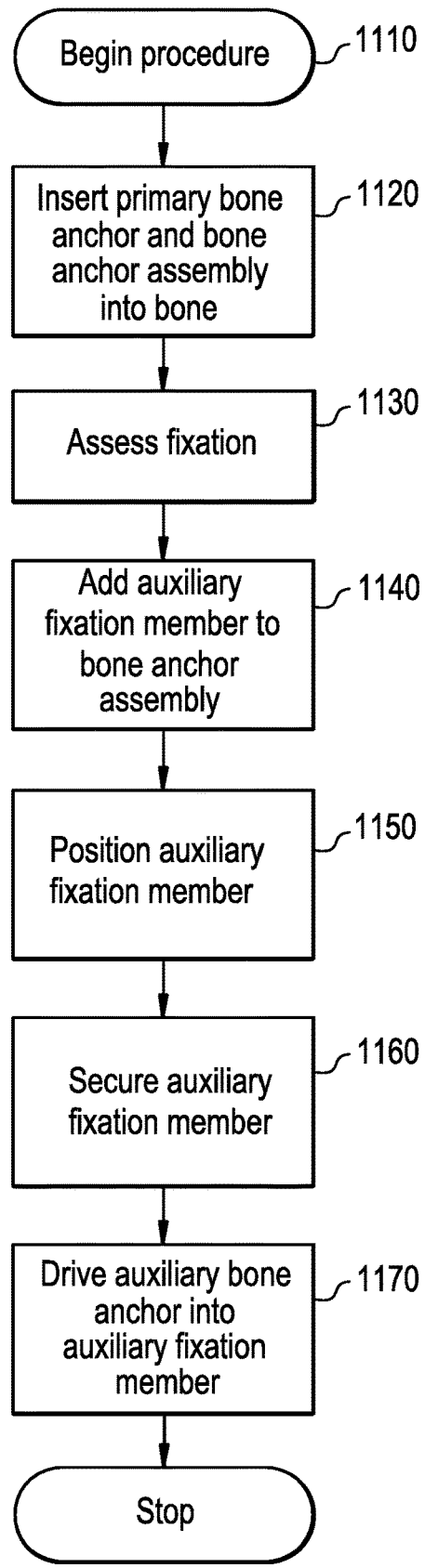
FIG. 24 illustrates an embodiment method of augmenting fixation of a bone anchor assembly using an auxiliary fixation member of the present disclosure.

An exemplary method of using the bone anchor assemblies disclosed herein is described below, with reference to FIG. 24.

A surgical procedure can begin in step 1110. For example, the procedure can begin by forming an open or percutaneous incision in the patient to access a bone in which a bone anchor assembly is to be implanted. The bone can be prepared to receive the bone anchor assembly as known in the art. For example, a pedicle of a vertebra can be prepared using standard awl, probe, and tap steps.

Next, the bone anchor can then be advanced into the bone in step 1120. After the primary bone anchor is advanced into the bone, i.e., a vertebra of a patient, a user can assess the fixation of the bone anchor given the particular circumstances of the patient's anatomy and the surgical application in step 1130. If the user feels that the purchase of the bone anchor is inadequate, or that auxiliary fixation would otherwise be desirable, an auxiliary fixation member can be selected based on the particular application added to the bone anchor assembly in step 1140. The selected fixation member can then be placed in a desired position (1150) and secured (1160) relative to the bone anchor assembly. With the fixation member secured, at least one auxiliary bone anchor screw can be driven into the bone to provide auxiliary fixation for the bone anchor (1170).

For example, referring to the embodiment of FIGS. 2A-2M, a spinal rod 206 can be seated in the receiver member 204 and a closure mechanism 208 can be threaded down onto the rod. A wing 230 can then be positioned over the closure mechanism 208 and secured in place with the nut 232. One or more auxiliary bone anchors 234 can be inserted through the wing 230 to attach the construct to the bone at a second location (or at more than two locations). The method can include bending or flexing the wing 230 to better fit the receiver member 204 or bone surface, for example by squeezing legs 258 of the wing together to increase a height of the wing.

As another example, referring to the embodiment of FIGS. 3A-3I, a spinal rod 506 can be seated in the receiver member 504 and a closure mechanism 508 can be threaded down onto the rod. A wing 530 can be positioned over the closure mechanism 508 and secured in place with the nut 532. As discussed above, the wing 530 can include a distal portion 530*d* that is angled to the right side of the wing 530. Thus, when the wing is positioned lateral to a bone anchor disposed to the left of the spinal midline when viewed from a posterior vantage point, an auxiliary bone anchor 534 can be inserted through the bone anchor opening 544 and driven into bone with a caudal trajectory. When the wing is positioned lateral to a bone anchor disposed to the right of the spinal midline when viewed from a posterior vantage point, an auxiliary bone anchor 534 can be inserted through the bone anchor opening 544 and driven into bone with a cephalad trajectory.

As another example, referring to the embodiment of FIGS. 5A-5F, a spinal rod 506 can be seated in the receiver member 504 and a closure mechanism 508 can be threaded down onto the rod. A wing 730 can be positioned over the closure mechanism 508 and secured in place with the nut 532. As discussed above, the wing 730 can include a distal portion 730*d* that is angled to the left side of the wing 730. Thus, when the wing is positioned lateral to a bone anchor disposed to the left of the spinal midline when viewed from a posterior vantage point, an auxiliary bone anchor 534 can be inserted through the bone anchor opening 744 and driven into bone with a cephalad trajectory. When the wing is positioned lateral to a bone anchor disposed to the right of the spinal midline when viewed from a posterior vantage point, an auxiliary bone anchor 534 can be inserted through the bone anchor opening 744 and driven into bone with a caudal trajectory.

As another example, referring to the embodiment of FIGS. 6A-6D, a spinal rod 506 can be seated in the receiver member 504 and a closure mechanism 508 can be threaded down onto the rod. A wing 830 can be positioned over the closure mechanism 508 and secured in place with the nut 532. As discussed above in some embodiments, the wing 830 can include a distal portion 830*d* that is angled to inward towards the spanning portion 830*s* of the wing 830. Thus, when the wing is positioned lateral to a bone anchor disposed to the left or right of the spinal midline when viewed from a posterior vantage point, an auxiliary bone anchor 534 can be inserted through the bone anchor opening 844 and driven into bone with a medial trajectory. In some embodiments, the wing 830 can include a distal portion 830*d* that is angled to outward away from the spanning portion 830*s* of the wing 830. Thus, when the wing is positioned lateral to a bone anchor disposed to the left or right of the spinal midline when viewed from a posterior vantage point, an auxiliary bone anchor 534 can be inserted through the bone anchor opening 844 and driven into bone with a lateral trajectory.

As yet another example, referring to the embodiments of FIGS. 7-23, a spinal rod can be seated in a receiver member of a bone anchor assembly and a closure mechanism can be threaded down onto the rod. After assessing a need to augment fixation of the bone anchor assembly with an auxiliary fixation member, the user can determine an optimal placement and trajectory of one or more auxiliary bone anchor screws to be received within the auxiliary fixation member. For example, a user may assess the spinal anatomy of the patient, the goals of a particular surgical procedure, and the condition of surrounding vertebrae, to determine whether a desired auxiliary fixation should include one or more auxiliary bone anchor screws violating a facet plane of the bone into which the bone anchor assembly is inserted. This may be appropriate in applications that do not require preservation of movement between adjacent vertebra. For example, in a surgical procedure in which the bone anchor assembly is inserted into a vertebral level that is fused with an adjacent vertebral level, a fixation strength of the bone anchor assembly can be increased by driving at least one auxiliary bone anchor screw through multiple layers of cortical bone. In other embodiments, a desired auxiliary fixation can include one or more auxiliary bone anchor screws that extend wholly within the bone, i.e., a vertebral level into which the bone anchor assembly is inserted, without any auxiliary bone anchor screws extending beyond the bone. For example, such an approach can be optimal in surgical applications where preserving movement between adjacent vertebra is desired. In some embodiments, it can be desirable to use a plurality of auxiliary bone anchor screw to augment fixation of the bone anchor assembly.

The user can then select an appropriate auxiliary fixation member, again taking into account patient anatomy and requirements of a particular surgical application, to achieve the desired auxiliary fixation. By way of non-limiting example, when selecting the appropriate auxiliary fixation member, the user can consider factors such as a location of the bone anchor assembly relative to a spinal midline of the patient, spinal anatomy, and bone quality in the surgical area. For example, in a surgical procedure performed in the cervical spine, a user may want to angulate the auxiliary bone anchor screws such that each conforms to the direction of a facet plane of the vertebra so as not to violate a non-fusion level.

In some embodiments, a wing 930 can be positioned over the closure mechanism 908 of a bone anchor assembly 900 and secured in place with the nut 932. As discussed above, the wing 930 can include a distal portion 930*d* having a plurality of auxiliary bone anchor openings 944 extending with a biased trajectory towards the left side of the wing 930. Thus, when the wing is positioned lateral to a bone anchor disposed to the left of the spinal midline when viewed form a posterior vantage point, an auxiliary bone anchor 934 can be inserted through the bone anchor opening 944 and driven into the bone with a caudal trajectory. When the wing is positioned lateral to a bone anchor disposed to the right of the spinal midline when viewed from a posterior vantage point, an auxiliary bone anchor 934 can be inserted through the bone anchor opening 944 and driven into bone with a cephalad trajectory.

For example, as shown in FIG. 7, a primary bone anchor can be implanted in a vertebra 901 with bone anchor assembly 900. The vertebra 901 can be defined by a superior facet plane 905 and an inferior facet plane 907. A wing 930 can be placed and secured in a desired position using fastener 932, as discussed above, such that a bone anchor 934 can be inserted and driven at a trajectory conforming to the vertebra 901 without violating either facet plane 905, 907. A driver instrument 909 can be used to insert the bone anchor 934 into an auxiliary bone anchor opening 944 in the distal portion 930 of wing. In the embodiment illustrated in FIG. 7, the wing 930 is placed on a lateral side to the left of the receiver 904. The central axis of the bone anchor openings 944 of the wing 930 extend in a cephalad direction such that an auxiliary bone anchor received therein extends towards a patient's head.

In other embodiments, a wing 1030 can be positioned over the closure mechanism 1008 of a bone anchor assembly 1000 and secured in place with the nut 1032. As discussed above, the wing 1030 can include a distal portion 1030*d* having a plurality of auxiliary bone anchor openings 1044 extending with a biased trajectory towards the right side of the wing 1030. Thus, when the wing is positioned lateral to a bone anchor disposed to the left of the spinal midline when viewed form a posterior vantage point, an auxiliary bone anchor 1034 can be inserted through the bone anchor opening 1044 and driven into the bone with a cephalad trajectory. When the wing is positioned lateral to a bone anchor disposed to the right of the spinal midline when viewed from a posterior vantage point, an auxiliary bone anchor 1034 can be inserted through the bone anchor opening 1044 and driven into bone with a caudal trajectory.

As discussed above, some embodiments of a wing can include one or more auxiliary bone anchor openings having an interlocking interface that can facilitate a variable angle locking connection with an auxiliary bone anchor screw. Accordingly, in these embodiments, a user can insert and drive an auxiliary bone anchor through an auxiliary bone anchor opening coaxial with a central axis of the auxiliary bone anchor opening or at an oblique angle with respect to the central axis of the auxiliary bone anchor opening. In this manner, a wing can provide an expanded range of angles or trajectories through which an auxiliary bone anchor can be inserted into a bone to augment fixation of a primary bone anchor.

The above steps can be repeated to install additional bone anchor assemblies at the same or at different vertebral levels, with or without auxiliary fixation members. Final tightening or other adjustment of the construct can be performed and the procedure can be completed using known techniques and the incision closed.

In any of the above embodiments or methods, the primary bone anchor can be omitted and the user can rely solely on the one or more auxiliary fixation features to secure the bone anchor assembly. This can advantageously allow the position of the fixation to be completely offset from the receiver member, for example if an initially placed bone anchor needs to be removed due to improper positioning or inadequate purchase, or when the receiver member needs to be positioned over a location where a bone anchor cannot be inserted.

While the methods illustrated and described herein involve a bone anchor assembly placed in the pedicle or lateral mass of vertebral bone, it will be appreciated that the systems and methods herein can be used in any bone, in non-bone tissue, or in non-living or non-tissue objects.

The auxiliary fixation members disclosed herein can be implanted in the same surgical procedure as the bone anchor, receiver member, and spinal rod, or, in the case of revision surgery, during a subsequent surgical procedure.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

As evident from the foregoing, in at least some embodiments, the systems and methods disclosed herein can provide enhanced fixation for a given surgical site, providing greater bone fixation strength at a given location without necessarily requiring moving the fixation to an additional vertebra or skipping/increasing the involved vertebral levels.

The bone anchor assemblies disclosed herein and the various component parts thereof can be constructed from any of a variety of known materials. Exemplary materials include those which are suitable for use in surgical applications, including metals such as stainless steel, titanium, or alloys thereof, polymers such as PEEK, ceramics, carbon fiber, and so forth. The various components of the devices disclosed herein can be rigid or flexible. One or more components or portions of the device can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

The systems and methods disclosed herein can be used in minimally-invasive surgery and/or open surgery. While the systems and methods disclosed herein are generally described in the context spinal surgery, it will be appreciated that the systems and methods disclosed herein can be used with any human or animal implant, in any of a variety of surgeries performed on humans or animals, and/or in fields unrelated to implants or surgery.

Although specific embodiments are described above, it should be understood that numerous changes may be made within the spirit and scope of the concepts described. Accordingly, it is intended that this disclosure not be limited to the described embodiments, but that it have the full scope defined by the language of the following claims.

The above exemplary embodiments describe a spinal surgical application. While this is one contemplated use, the methods and devices of the present disclosure can be equally adapted for use in other areas of a patient's body. As such, the devices described herein can be formed in a variety of sizes and materials appropriate for use in various areas of a patient's body.

One skilled in the art will appreciate further features and advantages based on the above-described embodiments. Accordingly, the disclosure is not to be limited by what has been particularly shown and described. All publications and references cited herein are expressly incorporated herein by reference in their entirety.

The invention claimed is:

1. A method of securing a primary bone anchor assembly to bone, comprising:
    driving a primary bone anchor into a vertebral level in a spine of a patient, the bone anchor having a receiver member coupled to a proximal end thereof;
    positioning a rod in the receiver member;
    attaching a closure mechanism to the receiver member to retain the rod in the receiver member;
    coupling a proximal portion of a wing to at least one of the closure mechanism and the receiver member, the wing having a distal portion defining a first auxiliary bone anchor opening and a second auxiliary bone anchor opening and a spanning portion connecting the proximal portion and the distal portion, where each of the first and second auxiliary bone anchor openings extends at an oblique angle relative to a proximal-distal axis of the spanning portion;
    positioning the wing relative to the receiver member such that the first auxiliary bone anchor opening and the second auxiliary bone anchor opening are biased in a cephalad direction and such that a first auxiliary bone anchor and a second auxiliary bone anchor received within the wing conform to the vertebral level into which the bone anchor is driven;
    inserting a first auxiliary bone anchor through the first auxiliary bone anchor opening at a first trajectory such that the first auxiliary bone anchor extends wholly within the vertebral level into which the primary bone anchor is driven;
    inserting a second auxiliary bone anchor through the second auxiliary bone anchor opening at a second trajectory such that the second auxiliary bone anchor extends wholly within the vertebral level into which the primary bone anchor is driven; and
    driving the first auxiliary bone anchor at the first trajectory into the vertebral level and the second auxiliary bone anchor at the second trajectory into the vertebral level such that the first auxiliary bone anchor and the second auxiliary bone anchor augment fixation of the primary bone anchor, wherein a central axis of the first auxiliary bone anchor opening and a central axis of the second auxiliary bone anchor opening are each biased between about 46 and about 60 degrees from the proximal-distal axis of the spanning portion.

2. The method of claim 1, wherein the vertebral level into which the primary bone anchor is driven is a vertebral level of a cervical spine.

3. The method of claim 1, wherein coupling the proximal portion of the wing to at least one of the closure mechanism and the proximal surface of the receiver member comprises attaching the wing via an extended set screw and locking the wing in place with a nut.

4. The method of claim 3, further comprising rotating the wing relative to the receiver member about an axis of the extended set screw to achieve a desired first auxiliary bone anchor opening trajectory and a desired second auxiliary bone anchor opening trajectory.

5. The method of claim 1, wherein driving the primary bone anchor into the vertebral level of the spine comprises driving the primary bone anchor into a fused vertebral level of the spine.

6. The method of claim 1, wherein driving the first auxiliary bone anchor at the first trajectory and driving the second auxiliary bone anchor at the second trajectory causes at least one of the first auxiliary bone anchor and the second auxiliary bone anchor to diverge from the primary bone anchor.

7. The method of claim 1, wherein a central axis of the first auxiliary bone anchor opening and a central axis of the second auxiliary bone anchor opening are each biased between about 0 and about 60 degrees from the proximal-distal axis of the spanning portion.

8. The method of claim 1, wherein the first trajectory extends at an oblique angle relative to a central axis of the first auxiliary bone anchor opening.

9. The method of claim 1, wherein inserting the first auxiliary bone anchor and inserting the second auxiliary bone anchor further comprises engaging a threaded surface of the first auxiliary bone anchor with an interlocking interface of the first auxiliary bone anchor opening and engaging a threaded surface of the second auxiliary bone anchor with an interlocking interface of the second auxiliary bone anchor opening.

10. The method of claim 1, further comprising positioning the wing such that there is an air gap between the distal portion of the wing and a proximal facing surface of the vertebral level into which the primary bone anchor is driven.

* * * * *